(12) United States Patent
Gierahn et al.

(10) Patent No.: US 11,207,375 B2
(45) Date of Patent: Dec. 28, 2021

(54) **VACCINES AND COMPOSITIONS AGAINST *STREPTOCOCCUS PNEUMONIAE***

(71) Applicants: Genocea Biosciences, Inc., Cambridge, MA (US); Children's Medical Center Corporation, Boston, MA (US)

(72) Inventors: Todd Gierahn, Brookline, MA (US); Richard Malley, Beverly, MA (US)

(73) Assignees: Genocea Biosciences, Inc., Cambridge, MA (US); Children's Medical Center Corporation, Boston, MA (US)

( * ) Notice: Subject to any disclaimer, the term of this patent is extended or adjusted under 35 U.S.C. 154(b) by 163 days.

(21) Appl. No.: 16/133,590

(22) Filed: Sep. 17, 2018

(65) Prior Publication Data

US 2019/0298795 A1    Oct. 3, 2019

Related U.S. Application Data

(62) Division of application No. 12/826,084, filed on Jun. 29, 2010, now Pat. No. 10,105,412.

(60) Provisional application No. 61/316,267, filed on Mar. 22, 2010, provisional application No. 61/240,616, filed on Sep. 8, 2009, provisional application No. 61/240,598, filed on Sep. 8, 2009, provisional application No. 61/221,541, filed on Jun. 29, 2009.

(51) Int. Cl.
| | |
|---|---|
| *A61K 39/02* | (2006.01) |
| *A61K 38/16* | (2006.01) |
| *A61K 38/02* | (2006.01) |
| *C07K 14/315* | (2006.01) |
| *A61K 39/00* | (2006.01) |

(52) U.S. Cl.
CPC .............. *A61K 38/16* (2013.01); *A61K 38/02* (2013.01); *C07K 14/3156* (2013.01); *A61K 39/00* (2013.01)

(58) Field of Classification Search
None
See application file for complete search history.

(56) References Cited

U.S. PATENT DOCUMENTS

| | | | |
|---|---|---|---|
| 5,371,197 A | 12/1994 | Marburg et al. | |
| 5,623,057 A | 4/1997 | Marburg et al. | |
| 5,643,576 A | 7/1997 | Johnston et al. | |
| 5,882,885 A | 3/1999 | Burnham | |
| 5,994,101 A | 11/1999 | Kallender et al. | |
| 6,235,285 B1 | 5/2001 | Burnham | |
| 6,248,558 B1 | 6/2001 | Lin et al. | |
| 6,432,680 B1 | 8/2002 | Lin et al. | |
| 6,573,082 B1 | 6/2003 | Choi et al. | |
| 6,617,156 B1 | 9/2003 | Doucette-Stamm et al. | |
| 6,699,703 B1 * | 3/2004 | Doucette-Stamm | ... C07H 21/04 435/252.3 |
| 6,783,939 B2 | 8/2004 | Olmsted et al. | |
| 6,887,480 B1 | 5/2005 | Adamou et al. | |
| 6,951,732 B2 | 10/2005 | Clarke et al. | |
| 7,056,510 B1 | 6/2006 | Choi et al. | |
| 7,132,107 B2 | 11/2006 | Adamou et al. | |
| 7,141,418 B2 | 11/2006 | Kunsch et al. | |
| 7,314,974 B2 | 1/2008 | Cao et al. | |
| 7,338,786 B2 | 3/2008 | Doucette-Stamm et al. | |
| 7,378,514 B2 | 5/2008 | Doucette-Stamm et al. | |
| 7,384,775 B2 * | 6/2008 | Zagursky | ............... C12Q 1/689 435/252.3 |
| 7,504,110 B2 | 3/2009 | Mizrachi Nebenzahl | |
| 7,635,487 B2 | 12/2009 | Meinke et al. | |
| 10,105,412 B2 | 10/2018 | Gierahn et al. | |
| 2004/0029118 A1 | 2/2004 | Kunsch et al. | |
| 2004/0029129 A1 | 2/2004 | Wang et al. | |
| 2004/0110181 A1 | 6/2004 | Zagursky et al. | |
| 2005/0020813 A1 | 1/2005 | Masignani et al. | |
| 2005/0136404 A1 | 6/2005 | Doucette-Stamm et al. | |
| 2005/0196415 A1 | 9/2005 | Nebenzahl | |
| 2006/0210579 A1 | 9/2006 | Telford et al. | |
| 2006/0210580 A1 | 9/2006 | Telford et al. | |
| 2006/0263846 A1 | 11/2006 | Meinke et al. | |
| 2007/0053924 A1 | 3/2007 | Tettelin et al. | |
| 2007/0154986 A1 | 7/2007 | Kunsch et al. | |
| 2007/0184443 A1 | 8/2007 | Covacci | |
| 2008/0175854 A1 | 7/2008 | Doucette-Stamm et al. | |
| 2009/0148470 A1 | 6/2009 | Nebenzahl | |
| 2009/0202528 A1 | 8/2009 | Kofoed et al. | |
| 2009/0215149 A1 | 8/2009 | Doucette-Stamm et al. | |
| 2009/0221499 A1 | 9/2009 | Leng et al. | |
| 2009/0252756 A1 | 10/2009 | Mizrachi-Nebenzahl | |

(Continued)

FOREIGN PATENT DOCUMENTS

| | | |
|---|---|---|
| EP | 0942983 A2 | 9/1999 |
| EP | 1 185 297 B1 | 3/2002 |

(Continued)

OTHER PUBLICATIONS

Rudikoff et al (Proc Natl Acad Sci USA 1982 vol. 79 p. 1979). (Year: 1979).*

(Continued)

*Primary Examiner* — Jana A Hines
*Assistant Examiner* — Khatol S Shahnan Shah
(74) *Attorney, Agent, or Firm* — Choate, Hall & Stewart LLP; Rolando Medina; Stephanie L. Schonewald

(57) ABSTRACT

*Streptococcus pneumoniae* is a major health concern, especially in very young, elderly, or immunocompromised patients. The present disclosure provides, inter alia, certain highly effective vaccines and pharmaceutical compositions in *Streptococcus pneumoniae*. The antigens may be used therapeutically or prophylactically.

34 Claims, 8 Drawing Sheets
Specification includes a Sequence Listing.

(56) References Cited

U.S. PATENT DOCUMENTS

| | | |
|---|---|---|
| 2010/0015168 A1 | 1/2010 | Maione et al. |
| 2010/0143399 A1 | 6/2010 | Biemans et al. |
| 2010/0166785 A1 | 7/2010 | Liu et al. |
| 2010/0221287 A1 | 9/2010 | Kunsch et al. |
| 2010/0221288 A1 | 9/2010 | Zagursky et al. |
| 2010/0247547 A1 | 9/2010 | Dong et al. |
| 2010/0260790 A1 | 10/2010 | Meinke et al. |
| 2010/0278819 A1 | 11/2010 | Bossuyt et al. |
| 2010/0303849 A1 | 12/2010 | Chen et al. |
| 2010/0322953 A1 | 12/2010 | Leng et al. |
| 2011/0020386 A1 | 1/2011 | Gierahn et al. |
| 2011/0135686 A1* | 6/2011 | Pugachev ............... A61P 31/12 424/218.1 |
| 2011/0177960 A1 | 7/2011 | Murphy et al. |
| 2011/0246740 A1 | 10/2011 | Yata et al. |
| 2011/0283062 A1 | 11/2011 | Kumagai et al. |
| 2012/0100172 A1 | 4/2012 | Tal et al. |
| 2012/0128707 A1 | 5/2012 | Masignani et al. |
| 2012/0189649 A1 | 7/2012 | Gierahn et al. |

FOREIGN PATENT DOCUMENTS

| | | |
|---|---|---|
| EP | 1328543 A2 | 7/2003 |
| EP | 1 572 868 A2 | 9/2005 |
| EP | 1 630 230 A2 | 3/2006 |
| EP | 1 855 717 A1 | 11/2007 |
| EP | 2 278 008 A2 | 1/2011 |
| EP | 2275128 A2 | 1/2011 |
| EP | 2311987 A1 | 4/2011 |
| JP | 2005-503119 A | 2/2005 |
| JP | 2007-525157 A | 9/2007 |
| WO | WO-97/37026 A1 | 10/1997 |
| WO | WO-98/18930 A2 | 5/1998 |
| WO | WO-98/18931 A2 | 5/1998 |
| WO | WO-98/50554 A2 | 11/1998 |
| WO | WO-98/59071 A1 | 12/1998 |
| WO | WO-00/06738 A2 | 2/2000 |
| WO | WO-02/077021 A2 | 10/2002 |
| WO | WO-02/083855 A2 | 10/2002 |
| WO | WO-03/082183 A2 | 10/2003 |
| WO | WO-2004/018646 A2 | 3/2004 |
| WO | WO-2004/020609 A2 | 3/2004 |
| WO | WO-2004/092209 A2 | 10/2004 |
| WO | WO-2005/014630 A2 | 2/2005 |
| WO | WO-2006069200 A2 | 6/2006 |
| WO | WO-2006/084467 A1 | 8/2006 |
| WO | WO-2007/106407 A2 | 9/2007 |
| WO | WO-2008081014 A2 | 7/2008 |
| WO | WO-2008/119358 A2 | 10/2008 |
| WO | WO-2008/146164 A2 | 12/2008 |
| WO | WO-2009011971 A3 | 1/2009 |
| WO | WO-2009/016515 A2 | 2/2009 |
| WO | WO-2009/033742 A2 | 3/2009 |
| WO | WO-2010064243 A1 | 6/2010 |
| WO | WO-2010150242 A2 | 12/2010 |
| WO | WO-2011/008548 A1 | 1/2011 |
| WO | WO-2011064781 A1 | 6/2011 |
| WO | WO-2011067758 A2 | 6/2011 |
| WO | WO-2011128892 A2 | 10/2011 |
| WO | WO-2011141968 A1 | 11/2011 |

OTHER PUBLICATIONS

Burgess et al. (J of Cell Biology, 1990 vol. 111, pp. 2129-2138) (Year: 1990).*

Briles, D.E et al., Intranasal Immunization of Mice with a Mixture of the Pneumococcal Proteins PSAA and PSPA is highly protective against nasopharyngeal carriage of *Streptococcus pneumoniae*, Infection and Immunity, 68(2): 796-800 (2000).

Briles, D.E. et al., The potential for using protein vaccines to protect against otitis media casued by *Streptococcus pneumoniae*, Vaccine, 19: S87-S95 (2001).

Brown, J.S. et al., Immunization with Components of Two Iron Uptake ABC Transporter Protests Mice against Systemic *Streptococcus pneumoniae* Infection, Infection and Immunity, 69(11): 6702-6706 (2001).

Cao et al., Enhanced protection against pneumococcal infection elicited by immunization with the combination of PspA, PspC, and ClpP, Vaccine, 25(27): 4996-5005 (2007).

Database UniParc, F5MIE7, retrieved from internet May 28, 2013 (Jul. 27, 2011).

Database UniParc, F9HBT0, retrieved from internet May 28, 2013 (Oct. 19, 2011).

Database UniParc, F9PYR1, retrieved from internet May 28, 2013 (Oct. 19, 2011).

Database UniParc, G6J1F1, retrieved from internet May 28, 2013 (Jan. 25, 2012).

Database UniParc, G6KAH8, retrieved from internet May 28, 2013 (Jan. 25, 2012).

Database UniParc, G6U2X1, retrieved from internet May 28, 2013 (Jan. 25, 2012).

Database UniParc, G6VVK1, retrieved from internet May 28, 2013 (Jan. 25, 2012).

Database UniprotKB, Lipidation, retrieved from internet May 28, 2013 (Feb. 17, 2011).

Ding, F. et al., Genome evolution driven by host adaptations results in a more virulent and antimicrobial-resistant *Streptococcus pneumoniae* serotype 14, BMC Genomics,10:158 (2009).

Dopazo, J. et al., Annotated Draft Genomic Sequence from a *Streptococcus pneumoniae* Type 19F Clinical Isolate, Microb. Drug Resist., 7(2):99-125 (2001).

Douce, G. et al. Genetically detoxified mutants of heat-labile toxin from *Escherichia coli* are able to act as oral adjuvants, Infect Immun., 67(9):4400-6 (1999).

Douce, G. et al., Mutants of *Escherichia coli* heat-labile toxin lacking ADP-ribosyltransferase activity act as nontoxic, mucosal adjuvants, PNAS, vol. 92: 1644-1648 (1995).

Evans, J.T. et al., Enhancement of antigen-specific immunity via the TLR4 ligands MPLTM adjuvant and Ribi.529, Expert Rev., Vaccines, 2(2); 219-229 (2003).

Extended European Search Report for EP 10800303.9, 12 pages (dated Mar. 27, 2013).

Giefing et al., Discovery of a novel class of highly conserved vaccine antigens using genomic scale antigenic fingerprinting of pneumococcus with human antibodies, The Journal of Experimental Medicine, 205(1):117-131 (2008).

Giuliani et al. Mucosal adjuvanticity and immunogenicity of L TR72, a novel mutant of *Escherichia coli* heat-labile enterotoxin with partial knockout of ADP-ribosyltransferase activity, J Exp Med., 6:187(7):1123-32 (1998).

Grubaugh, D. et al., Proteins as T Cell Antigens: Methods for High-Throughput Identifications, Vaccine (2013).

Hoskins, J. et al., Genome of the Bacertium *Streptococcus pneumoniae* Strain R6., J Bacteriol, 183(19): 5709-5717 (2001).

Huse et al., Generation of a Large Combinatorial Library of the Immunoglobulin Repertoire in Phage Lambda, Science, 246: 1275-1281 (1989).

International Preliminary Report on Patentability for PCT/US12/22127, dated Jul. 23, 2013, 5 pages.

International Preliminary Report on Patentability for PCT/US12/22128, dated Jul. 23, 2013, 6 pages.

International Search Report for PCT/US12/22127, dated May 15, 2012, 4 pages.

International Search Report for PCT/US12/22128, dated May 21, 2012, 4 pages.

International Search Report for PCT/US13/22309, dated May 24, 2013, 4 pages.

International Search Report of PCT/US13/29907, dated Jun. 20, 2013, 3 pages.

Ishizaka S.T. et al. E6020: a synthetic Toll-like receptor 4 agonist as a vaccine adjuvant, Expert Rev. Vaccines, 6(5):773-84. (2007).

Jedrzejas, M.J., Unveiling molecular mechanisms of bacterial surface proteins: *Streptococcus pneumoniae* as a model organism for structural studies, Cell. Mol. Life Sci., 64(21): 2799-2822 (2007).

(56) References Cited

OTHER PUBLICATIONS

Lanie, J.A et al., Genome Sequence of Avery's Virulent Serotype 2 Strain D39 of *Streptococcus pneumoniae* and Comparison with That of Unencapsulated Laboratory Strain R6, J Bacteriol., 189(1): 38-51 (2007).

Lu et al. Protection against Pneumococcal colonization and fatal pneumonia by a trivalent conjugate of a fusion protein with the cell wall polysaccharide, Infect Immun., 77(5): 2076-83 (2009).

Lu et al., Interleukin-17A mediates acquired immunity to pneumococcal colonization, PLoS Pathogens, 4(9): e1000159 1-11 (2008).

Morsczeck, C. et al., *Streptococcus pneumoniae*: proteomics of surface proteins for vaccine development, European Society of Clinical Microbiology and Infectious Diseases, CMI, 14(1): 74-81 (2007).

Shah, P. et al., Immunization with Polyamine Transport Protein PotD Protects Mice against Systemic Infection with *Streptococcus pneumoniae*, Infection and Immunity 74(10): 5888-5892 (2006).

Singh et al., Advances in Vaccine Adjuvants for Infectious Diseases, Current HIV Research, 1:309-20 (2003).

Tedder et al. Isolation and generation of human dendritic cells, Current Protocols in Immunology, Supp23: 7.32.1-7.32.16 (1997).

Tettelin H et al.: Complete Genome Sequence of a Virulent Isolate of *Streptococcus pneumoniae*, Science, 293(5529): 498-506 (2001).

Wiezmann et al. Use of a Whole Genome Approach to Identify Vaccine Molecules Affording Protection against *Streptococcus pneumoniae* Infection, Infection and Immunity, 69(3): 1593-1598 (2001).

Williams, A.E. et al., Innate Imprinting by the Modified Heat-Labile Toxin of *Escherichia coli* (L TK63) Provides Generic Protection against Lung Infectious Disease, The Journal of Immunology, 173: 7435-7443 (2004).

Written Opinion for PCT/US12/22127, dated May 15, 2012, 7 pages.

Written Opinion for PCT/US12/22128, dated May 21, 2012, 8 pages.

Written Opinion for PCT/US13/22309, dated May 24, 2013, 12 pages.

Written Opinion of PCT/US13/29907, dated Jun. 20, 2013, 4 pages.

Wu, Y. et al., Hsp70-Like Protein 1 Fusion Protein Enhances Induction of Carcinoembryonic Antigen-Specific CD8+ CTL Response by Dendritic Cell Vaccine, Cancer Res., 65(11), 4947-4954 (2005).

Yamamoto, M. et al., Oral Immunization with PSPA Elicits protective humoral immunity against *Streptococcus pneumoniae* infection, Infection and Immunity, 65(2): 640-644 (1997).

\* cited by examiner

SEQUENCE LISTING

<160> NUMBER OF SEQ ID NOS: 264

<210> SEQ ID NO 1
<211> LENGTH: 165
<212> TYPE: PRT
<213> ORGANISM: Streptococcus pneumoniae

<400> SEQUENCE: 1

Met Ser Tyr Phe Glu Gln Phe Met Gln Ala Asn Gln Ala Tyr Val Ala
1               5                   10                  15

```
Leu His Gly Gln Leu Asn Leu Pro Leu Lys Pro Lys Thr Arg Val Ala
                20                  25                  30

Ile Val Thr Cys Met Asp Ser Arg Leu His Val Ala Gln Ala Leu Gly
            35                  40                  45

Leu Ala Leu Gly Asp Ala His Ile Leu Arg Asn Ala Gly Gly Arg Val
        50                  55                  60

Thr Glu Asp Met Ile Arg Ser Leu Val Ile Ser Gln Gln Gln Met Gly
65                  70                  75                  80

Thr Arg Glu Ile Val Val Leu His His Thr Asp Cys Gly Ala Gln Thr
                85                  90                  95

Phe Glu Asn Glu Pro Phe Gln Glu Tyr Leu Lys Glu Glu Leu Gly Val
            100                 105                 110

Asp Val Ser Asp Gln Asp Phe Leu Pro Phe Gln Asp Ile Glu Glu Ser
        115                 120                 125

Val Arg Glu Asp Met Gln Leu Leu Ile Glu Ser Pro Leu Ile Pro Asp
    130                 135                 140

Asp Val Ile Ile Ser Gly Ala Ile Tyr Asn Val Asp Thr Gly Ser Met
145                 150                 155                 160

Thr Val Val Glu Leu
                165

<210> SEQ ID NO 2
<211> LENGTH: 274
<212> TYPE: PRT
<213> ORGANISM: Streptococcus pneumoniae

<400> SEQUENCE: 2

Met Asn Gln Ser Tyr Phe Tyr Leu Lys Met Lys Glu His Lys Leu Lys
1               5                   10                  15

Val Pro Tyr Thr Gly Lys Glu Arg Arg Val Arg Ile Leu Leu Pro Lys
                20                  25                  30

Asp Tyr Glu Lys Asp Thr Asp Arg Ser Tyr Pro Val Val Tyr Phe His
            35                  40                  45

Asp Gly Gln Asn Val Phe Asn Ser Lys Glu Ser Phe Ile Gly His Ser
        50                  55                  60

Trp Lys Ile Ile Pro Ala Ile Lys Arg Asn Pro Asp Ile Ser Arg Met
65                  70                  75                  80

Ile Val Val Ala Ile Asp Asn Asp Gly Met Gly Arg Met Asn Glu Tyr
                85                  90                  95

Ala Ala Trp Lys Phe Gln Glu Ser Pro Ile Pro Gly Gln Gln Phe Gly
            100                 105                 110

Gly Lys Gly Val Glu Tyr Ala Glu Phe Val Met Glu Val Val Lys Pro
        115                 120                 125

Phe Ile Asp Glu Thr Tyr Arg Thr Lys Ala Asp Cys Gln His Thr Ala
    130                 135                 140

Met Ile Gly Ser Ser Leu Gly Gly Asn Ile Thr Gln Phe Ile Gly Leu
145                 150                 155                 160

Glu Tyr Gln Asp Gln Ile Gly Cys Leu Gly Val Phe Ser Ser Ala Asn
                165                 170                 175

Trp Leu His Gln Glu Ala Phe Asn Arg Tyr Phe Glu Cys Gln Lys Leu
            180                 185                 190

Ser Pro Asp Gln Arg Ile Phe Ile Tyr Val Gly Thr Glu Glu Ala Asp
        195                 200                 205

Asp Thr Asp Lys Thr Leu Met Asp Gly Asn Ile Lys Gln Ala Tyr Ile
```

```
                  210                 215                 220
Asp Ser Ser Leu Cys Tyr Tyr His Asp Leu Ile Ala Gly Gly Val His
225                 230                 235                 240

Leu Asp Asn Leu Val Leu Lys Val Gln Ser Gly Ala Ile His Ser Glu
                245                 250                 255

Ile Pro Trp Ser Glu Asn Leu Pro Asp Cys Leu Arg Phe Phe Ala Glu
                260                 265                 270

Lys Trp

<210> SEQ ID NO 3
<211> LENGTH: 130
<212> TYPE: PRT
<213> ORGANISM: Streptococcus pneumoniae

<400> SEQUENCE: 3

Met Asn Gln Ser Tyr Phe Tyr Leu Lys Met Lys Glu His Lys Leu Lys
1               5                   10                  15

Val Pro Tyr Thr Gly Lys Glu Arg Arg Val Arg Ile Leu Leu Pro Lys
                20                  25                  30

Asp Tyr Glu Lys Asp Thr Asp Arg Ser Tyr Pro Val Val Tyr Phe His
            35                  40                  45

Asp Gly Gln Asn Val Phe Asn Ser Lys Glu Ser Phe Ile Gly His Ser
        50                  55                  60

Trp Lys Ile Ile Pro Ala Ile Lys Arg Asn Pro Asp Ile Ser Arg Met
65                  70                  75                  80

Ile Val Val Ala Ile Asp Asn Asp Gly Met Gly Arg Met Asn Glu Tyr
                85                  90                  95

Ala Ala Trp Lys Phe Gln Glu Ser Pro Ile Pro Gly Gln Gln Phe Gly
                100                 105                 110

Gly Lys Gly Val Glu Tyr Ala Glu Phe Val Met Glu Val Val Lys Pro
            115                 120                 125

Phe Ile
    130

<210> SEQ ID NO 4
<211> LENGTH: 299
<212> TYPE: PRT
<213> ORGANISM: Streptococcus pneumoniae

<400> SEQUENCE: 4

Met Ser Ser Lys Phe Met Lys Ser Ala Ala Val Leu Gly Thr Ala Thr
1               5                   10                  15

Leu Ala Ser Leu Leu Leu Val Ala Cys Met Asn Gln Ser Tyr Phe Tyr
                20                  25                  30

Leu Lys Met Lys Glu His Lys Leu Lys Val Pro Tyr Thr Gly Lys Glu
            35                  40                  45

Arg Arg Val Arg Ile Leu Leu Pro Lys Asp Tyr Glu Lys Asp Thr Asp
        50                  55                  60

Arg Ser Tyr Pro Val Val Tyr Phe His Asp Gly Gln Asn Val Phe Asn
65                  70                  75                  80

Ser Lys Glu Ser Phe Ile Gly His Ser Trp Lys Ile Ile Pro Ala Ile
                85                  90                  95

Lys Arg Asn Pro Asp Ile Ser Arg Met Ile Val Val Ala Ile Asp Asn
                100                 105                 110

Asp Gly Met Gly Arg Met Asn Glu Tyr Ala Ala Trp Lys Phe Gln Glu
            115                 120                 125
```

```
Ser Pro Ile Pro Gly Gln Gln Phe Gly Gly Lys Gly Val Glu Tyr Ala
    130                 135                 140

Glu Phe Val Met Glu Val Val Lys Pro Phe Ile Asp Glu Thr Tyr Arg
145                 150                 155                 160

Thr Lys Ala Asp Cys Gln His Thr Ala Met Ile Gly Ser Ser Leu Gly
                165                 170                 175

Gly Asn Ile Thr Gln Phe Ile Gly Leu Glu Tyr Gln Asp Gln Ile Gly
            180                 185                 190

Cys Leu Gly Val Phe Ser Ser Ala Asn Trp Leu His Gln Glu Ala Phe
        195                 200                 205

Asn Arg Tyr Phe Glu Cys Gln Lys Leu Ser Pro Asp Gln Arg Ile Phe
    210                 215                 220

Ile Tyr Val Gly Thr Glu Glu Ala Asp Asp Thr Asp Lys Thr Leu Met
225                 230                 235                 240

Asp Gly Asn Ile Lys Gln Ala Tyr Ile Asp Ser Ser Leu Cys Tyr Tyr
                245                 250                 255

His Asp Leu Ile Ala Gly Gly Val His Leu Asp Asn Leu Val Leu Lys
            260                 265                 270

Val Gln Ser Gly Ala Ile His Ser Glu Ile Pro Trp Ser Glu Asn Leu
        275                 280                 285

Pro Asp Cys Leu Arg Phe Phe Ala Glu Lys Trp
    290                 295

<210> SEQ ID NO 5
<211> LENGTH: 155
<212> TYPE: PRT
<213> ORGANISM: Streptococcus pneumoniae

<400> SEQUENCE: 5

Met Ser Ser Lys Phe Met Lys Ser Ala Ala Val Leu Gly Thr Ala Thr
1               5                   10                  15

Leu Ala Ser Leu Leu Leu Val Ala Cys Met Asn Gln Ser Tyr Phe Tyr
            20                  25                  30

Leu Lys Met Lys Glu His Lys Leu Lys Val Pro Tyr Thr Gly Lys Glu
        35                  40                  45

Arg Arg Val Arg Ile Leu Leu Pro Lys Asp Tyr Glu Lys Asp Thr Asp
    50                  55                  60

Arg Ser Tyr Pro Val Val Tyr Phe His Asp Gly Gln Asn Val Phe Asn
65                  70                  75                  80

Ser Lys Glu Ser Phe Ile Gly His Ser Trp Lys Ile Ile Pro Ala Ile
                85                  90                  95

Lys Arg Asn Pro Asp Ile Ser Arg Met Ile Val Val Ala Ile Asp Asn
            100                 105                 110

Asp Gly Met Gly Arg Met Asn Glu Tyr Ala Ala Trp Lys Phe Gln Glu
        115                 120                 125

Ser Pro Ile Pro Gly Gln Gln Phe Gly Gly Lys Gly Val Glu Tyr Ala
    130                 135                 140

Glu Phe Val Met Glu Val Val Lys Pro Phe Ile
145                 150                 155

<210> SEQ ID NO 6
<211> LENGTH: 254
<212> TYPE: PRT
<213> ORGANISM: Streptococcus pneumoniae

<400> SEQUENCE: 6
```

Met Cys Ser Gly Gly Ala Lys Lys Glu Gly Glu Ala Ala Ser Lys Lys
1               5                   10                  15

Glu Ile Ile Val Ala Thr Asn Gly Ser Pro Lys Pro Phe Ile Tyr Glu
                20                  25                  30

Glu Asn Gly Glu Leu Thr Gly Tyr Glu Ile Glu Val Val Arg Ala Ile
            35                  40                  45

Phe Lys Asp Ser Asp Lys Tyr Asp Val Lys Phe Glu Lys Thr Glu Trp
50                  55                  60

Ser Gly Val Phe Ala Gly Leu Asp Ala Asp Arg Tyr Asn Met Ala Val
65                  70                  75                  80

Asn Asn Leu Ser Tyr Thr Lys Glu Arg Ala Glu Lys Tyr Leu Tyr Ala
                85                  90                  95

Ala Pro Ile Ala Gln Asn Pro Asn Val Leu Val Val Lys Lys Asp Asp
            100                 105                 110

Ser Ser Ile Lys Ser Leu Asp Asp Ile Gly Gly Lys Ser Thr Glu Val
        115                 120                 125

Val Gln Ala Thr Thr Ser Ala Lys Gln Leu Glu Ala Tyr Asn Ala Glu
130                 135                 140

His Thr Asp Asn Pro Thr Ile Leu Asn Tyr Thr Lys Ala Asp Phe Gln
145                 150                 155                 160

Gln Ile Met Val Arg Leu Ser Asp Gly Gln Phe Asp Tyr Lys Ile Phe
                165                 170                 175

Asp Lys Ile Gly Val Glu Thr Val Ile Lys Asn Gln Gly Leu Asp Asn
            180                 185                 190

Leu Lys Val Ile Glu Leu Pro Ser Asp Gln Gln Pro Tyr Val Tyr Pro
        195                 200                 205

Leu Leu Ala Gln Gly Gln Asp Glu Leu Lys Ser Phe Val Asp Lys Arg
210                 215                 220

Ile Lys Glu Leu Tyr Lys Asp Gly Thr Leu Gly Lys Leu Ser Lys Gln
225                 230                 235                 240

Phe Phe Gly Asp Thr Tyr Leu Pro Ala Glu Ala Asp Ile Lys
                245                 250

<210> SEQ ID NO 7
<211> LENGTH: 276
<212> TYPE: PRT
<213> ORGANISM: Streptococcus pneumoniae

<400> SEQUENCE: 7

Met Lys Lys Ile Val Lys Tyr Ser Ser Leu Ala Ala Leu Ala Leu Val
1               5                   10                  15

Ala Ala Gly Val Leu Ala Ala Cys Ser Gly Gly Ala Lys Lys Glu Gly
                20                  25                  30

Glu Ala Ala Ser Lys Lys Glu Ile Ile Val Ala Thr Asn Gly Ser Pro
            35                  40                  45

Lys Pro Phe Ile Tyr Glu Glu Asn Gly Glu Leu Thr Gly Tyr Glu Ile
50                  55                  60

Glu Val Val Arg Ala Ile Phe Lys Asp Ser Asp Lys Tyr Asp Val Lys
65                  70                  75                  80

Phe Glu Lys Thr Glu Trp Ser Gly Val Phe Ala Gly Leu Asp Ala Asp
                85                  90                  95

Arg Tyr Asn Met Ala Val Asn Asn Leu Ser Tyr Thr Lys Glu Arg Ala
            100                 105                 110

Glu Lys Tyr Leu Tyr Ala Ala Pro Ile Ala Gln Asn Pro Asn Val Leu

```
            115                 120                 125
Val Val Lys Lys Asp Asp Ser Ser Ile Lys Ser Leu Asp Asp Ile Gly
    130                 135                 140

Gly Lys Ser Thr Glu Val Val Gln Ala Thr Thr Ser Ala Lys Gln Leu
145                 150                 155                 160

Glu Ala Tyr Asn Ala Glu His Thr Asp Asn Pro Thr Ile Leu Asn Tyr
                165                 170                 175

Thr Lys Ala Asp Phe Gln Gln Ile Met Val Arg Leu Ser Asp Gly Gln
            180                 185                 190

Phe Asp Tyr Lys Ile Phe Asp Lys Ile Gly Val Glu Thr Val Ile Lys
        195                 200                 205

Asn Gln Gly Leu Asp Asn Leu Lys Val Ile Glu Leu Pro Ser Asp Gln
    210                 215                 220

Gln Pro Tyr Val Tyr Pro Leu Leu Ala Gln Gly Gln Asp Glu Leu Lys
225                 230                 235                 240

Ser Phe Val Asp Lys Arg Ile Lys Glu Leu Tyr Lys Asp Gly Thr Leu
                245                 250                 255

Glu Lys Leu Ser Lys Gln Phe Phe Gly Asp Thr Tyr Leu Pro Ala Glu
            260                 265                 270

Ala Asp Ile Lys
        275

<210> SEQ ID NO 8
<211> LENGTH: 586
<212> TYPE: PRT
<213> ORGANISM: Streptococcus pneumoniae

<400> SEQUENCE: 8

Met Val Asp Lys Gln Val Ile Glu Glu Ile Lys Asn Asn Ala Asn Ile
1               5                   10                  15

Val Glu Val Ile Gly Asp Val Ile Ser Leu Gln Lys Ala Gly Arg Asn
                20                  25                  30

Tyr Leu Gly Leu Cys Pro Phe His Gly Glu Lys Thr Pro Ser Phe Asn
            35                  40                  45

Val Val Glu Asp Lys Gln Phe Tyr His Cys Phe Gly Cys Gly Arg Ser
        50                  55                  60

Gly Asp Val Phe Lys Phe Ile Glu Glu Tyr Gln Gly Val Pro Phe Ile
65                  70                  75                  80

Glu Ala Val Gln Ile Leu Gly Gln Arg Val Gly Ile Glu Val Glu Lys
                85                  90                  95

Pro Leu Tyr Ser Glu Gln Lys Ser Ala Ser Pro His Gln Ala Leu Tyr
            100                 105                 110

Asp Met His Glu Asp Ala Ala Lys Phe Tyr His Ala Ile Leu Met Thr
        115                 120                 125

Thr Thr Met Gly Glu Glu Ala Arg Asn Tyr Leu Tyr Gln Arg Gly Leu
    130                 135                 140

Thr Asp Glu Val Leu Lys His Phe Trp Ile Gly Leu Ala Pro Pro Glu
145                 150                 155                 160

Arg Asn Tyr Leu Tyr Gln Arg Leu Ser Asp Gln Tyr Arg Glu Glu Asp
                165                 170                 175

Leu Leu Asp Ser Gly Leu Phe Tyr Leu Ser Asp Ala Asn Gln Phe Val
            180                 185                 190

Asp Thr Phe His Asn Arg Ile Met Phe Pro Leu Thr Asn Asp Gln Gly
        195                 200                 205
```

-continued

```
Lys Val Ile Ala Phe Ser Gly Arg Ile Trp Gln Lys Thr Asp Ser Gln
    210                 215                 220

Thr Ser Lys Tyr Lys Asn Ser Arg Ser Thr Ala Ile Phe Asn Lys Ser
225                 230                 235                 240

Tyr Glu Leu Tyr His Met Asp Arg Ala Lys Arg Ser Ser Gly Lys Ala
                245                 250                 255

Ser Glu Ile Tyr Leu Met Glu Gly Phe Met Asp Val Ile Ala Ala Tyr
            260                 265                 270

Arg Ala Gly Ile Glu Asn Ala Val Ala Ser Met Gly Thr Ala Leu Ser
        275                 280                 285

Arg Glu His Val Glu His Leu Lys Arg Leu Thr Lys Lys Leu Val Leu
    290                 295                 300

Val Tyr Asp Gly Asp Lys Ala Gly Gln Ala Ala Thr Leu Lys Ala Leu
305                 310                 315                 320

Asp Glu Ile Gly Asp Met Pro Val Gln Ile Val Ser Met Pro Asp Asn
                325                 330                 335

Leu Asp Pro Asp Glu Tyr Leu Gln Lys Asn Gly Pro Glu Asp Leu Ala
            340                 345                 350

Tyr Leu Leu Thr Lys Thr Arg Ile Ser Pro Ile Glu Phe Tyr Ile His
        355                 360                 365

Gln Tyr Lys Pro Glu Asn Ser Glu Asn Leu Gln Ala Gln Ile Glu Phe
    370                 375                 380

Leu Glu Lys Ile Ala Pro Leu Ile Val Gln Glu Lys Ser Ile Ala Ala
385                 390                 395                 400

Gln Asn Ser Tyr Ile His Ile Leu Ala Asp Ser Leu Ala Ser Phe Asp
                405                 410                 415

Tyr Thr Gln Ile Glu Gln Ile Val Asn Glu Ser Arg Gln Val Gln Arg
            420                 425                 430

Gln Asn Arg Met Glu Gly Ile Ser Arg Pro Thr Pro Ile Thr Met Pro
        435                 440                 445

Val Thr Lys Gln Leu Ser Ala Ile Met Arg Ala Glu Ala His Leu Leu
    450                 455                 460

Tyr Arg Met Met Glu Ser Pro Leu Val Leu Asn Asp Tyr Arg Leu Arg
465                 470                 475                 480

Glu Asp Phe Ala Phe Ala Thr Pro Glu Phe Gln Val Leu Tyr Asp Leu
                485                 490                 495

Leu Gly Gln Tyr Gly Asn Leu Pro Pro Glu Val Leu Ala Glu Gln Thr
            500                 505                 510

Glu Glu Val Glu Arg Ala Trp Tyr Gln Val Leu Ala Gln Asp Leu Pro
        515                 520                 525

Ala Glu Ile Ser Pro Gln Glu Leu Ser Glu Val Glu Met Thr Arg Asn
    530                 535                 540

Lys Ala Leu Leu Asn Gln Asp Asn Met Arg Ile Lys Lys Val Gln
545                 550                 555                 560

Glu Ala Ser His Val Gly Asp Thr Asp Thr Ala Leu Glu Glu Leu Glu
                565                 570                 575

Arg Leu Ile Ser Gln Lys Arg Arg Met Glu
            580                 585

<210> SEQ ID NO 9
<211> LENGTH: 423
<212> TYPE: PRT
<213> ORGANISM: Streptococcus pneumoniae

<400> SEQUENCE: 9
```

```
Met Ser Ser Lys Phe Met Lys Ser Ala Ala Val Leu Gly Thr Ala Thr
1               5                   10                  15

Leu Ala Ser Leu Leu Val Ala Cys Gly Ser Lys Thr Ala Asp Lys
            20                  25                  30

Pro Ala Asp Ser Gly Ser Ser Glu Val Lys Glu Leu Thr Val Tyr Val
        35                  40                  45

Asp Glu Gly Tyr Lys Ser Tyr Ile Glu Val Ala Lys Ala Tyr Glu
    50                  55                  60

Lys Glu Ala Gly Val Lys Val Thr Leu Lys Thr Gly Asp Ala Leu Gly
65                  70                  75                  80

Gly Leu Asp Lys Leu Ser Leu Asp Asn Gln Ser Gly Asn Val Pro Asp
                85                  90                  95

Val Met Met Ala Pro Tyr Asp Arg Val Gly Ser Leu Gly Ser Asp Gly
                100                 105                 110

Gln Leu Ser Glu Val Lys Leu Ser Asp Gly Ala Lys Thr Asp Asp Thr
        115                 120                 125

Thr Lys Ser Leu Val Thr Ala Ala Asn Gly Lys Val Tyr Gly Ala Pro
    130                 135                 140

Ala Val Ile Glu Ser Leu Val Met Tyr Tyr Asn Lys Asp Leu Val Lys
145                 150                 155                 160

Asp Ala Pro Lys Thr Phe Ala Asp Leu Glu Asn Leu Ala Lys Asp Ser
                165                 170                 175

Lys Tyr Ala Phe Ala Gly Glu Asp Gly Lys Thr Thr Ala Phe Leu Ala
            180                 185                 190

Asp Trp Thr Asn Phe Tyr Tyr Thr Tyr Gly Leu Leu Ala Gly Asn Gly
                195                 200                 205

Ala Tyr Val Phe Gly Gln Asn Gly Lys Asp Ala Lys Asp Ile Gly Leu
    210                 215                 220

Ala Asn Asp Gly Ser Ile Val Gly Ile Asn Tyr Ala Lys Ser Trp Tyr
225                 230                 235                 240

Glu Lys Trp Pro Lys Gly Met Gln Asp Thr Glu Gly Ala Gly Asn Leu
                245                 250                 255

Ile Gln Thr Gln Phe Gln Glu Gly Lys Thr Ala Ala Ile Ile Asp Gly
                260                 265                 270

Pro Trp Lys Ala Gln Ala Phe Lys Asp Ala Lys Val Asn Tyr Gly Val
    275                 280                 285

Ala Thr Ile Pro Thr Leu Pro Asn Gly Lys Glu Tyr Ala Ala Phe Gly
    290                 295                 300

Gly Gly Lys Ala Trp Val Ile Pro Gln Ala Val Lys Asn Leu Glu Ala
305                 310                 315                 320

Ser Gln Lys Phe Val Asp Phe Leu Val Ala Thr Glu Gln Gln Lys Val
                325                 330                 335

Leu Tyr Asp Lys Thr Asn Glu Ile Pro Ala Asn Thr Glu Ala Arg Ser
            340                 345                 350

Tyr Ala Glu Gly Lys Asn Asp Glu Leu Thr Thr Ala Val Ile Lys Gln
            355                 360                 365

Phe Lys Asn Thr Gln Pro Leu Pro Asn Ile Ser Gln Met Ser Ala Val
    370                 375                 380

Trp Asp Pro Ala Lys Asn Met Leu Phe Asp Ala Val Ser Gly Gln Lys
385                 390                 395                 400

Asp Ala Lys Thr Ala Ala Asn Asp Ala Val Thr Leu Ile Lys Glu Thr
                405                 410                 415
```

Ile Lys Gln Lys Phe Gly Glu
            420

<210> SEQ ID NO 10
<211> LENGTH: 400
<212> TYPE: PRT
<213> ORGANISM: Streptococcus pneumoniae

<400> SEQUENCE: 10

Met Cys Gly Ser Lys Thr Ala Asp Lys Pro Ala Asp Ser Gly Ser Ser
1               5                   10                  15

Glu Val Lys Glu Leu Thr Val Tyr Val Asp Glu Gly Tyr Lys Ser Tyr
            20                  25                  30

Ile Glu Glu Val Ala Lys Ala Tyr Glu Lys Glu Ala Gly Val Lys Val
        35                  40                  45

Thr Leu Lys Thr Gly Asp Ala Leu Gly Gly Leu Asp Lys Leu Ser Leu
    50                  55                  60

Asp Asn Gln Ser Gly Asn Val Pro Asp Val Met Met Ala Pro Tyr Asp
65                  70                  75                  80

Arg Val Gly Ser Leu Gly Ser Asp Gly Gln Leu Ser Glu Val Lys Leu
                85                  90                  95

Ser Asp Gly Ala Lys Thr Asp Asp Thr Thr Lys Ser Leu Val Thr Ala
            100                 105                 110

Ala Asn Gly Lys Val Tyr Gly Ala Pro Ala Val Ile Glu Ser Leu Val
        115                 120                 125

Met Tyr Tyr Asn Lys Asp Leu Val Lys Asp Ala Pro Lys Thr Phe Ala
    130                 135                 140

Asp Leu Glu Asn Leu Ala Lys Asp Ser Lys Tyr Ala Phe Ala Gly Glu
145                 150                 155                 160

Asp Gly Lys Thr Thr Ala Phe Leu Ala Asp Trp Thr Asn Phe Tyr Tyr
                165                 170                 175

Thr Tyr Gly Leu Leu Ala Gly Asn Gly Ala Tyr Val Phe Gly Gln Asn
            180                 185                 190

Gly Lys Asp Ala Lys Asp Ile Gly Leu Ala Asn Asp Gly Ser Ile Val
        195                 200                 205

Gly Ile Asn Tyr Ala Lys Ser Trp Tyr Glu Lys Trp Pro Lys Gly Met
    210                 215                 220

Gln Asp Thr Glu Gly Ala Gly Asn Leu Ile Gln Thr Gln Phe Gln Glu
225                 230                 235                 240

Gly Lys Thr Ala Ala Ile Ile Asp Gly Pro Trp Lys Ala Gln Ala Phe
                245                 250                 255

Lys Asp Ala Lys Val Asn Tyr Gly Val Ala Thr Ile Pro Thr Leu Pro
            260                 265                 270

Asn Gly Lys Glu Tyr Ala Ala Phe Gly Gly Lys Ala Trp Val Ile
        275                 280                 285

Pro Gln Ala Val Lys Asn Leu Glu Ala Ser Gln Lys Phe Val Asp Phe
    290                 295                 300

Leu Val Ala Thr Glu Gln Lys Val Leu Tyr Asp Lys Thr Asn Glu
305                 310                 315                 320

Ile Pro Ala Asn Thr Glu Ala Arg Ser Tyr Ala Glu Gly Lys Asn Asp
                325                 330                 335

Glu Leu Thr Thr Ala Val Ile Lys Gln Phe Lys Asn Thr Gln Pro Leu
            340                 345                 350

Pro Asn Ile Ser Gln Met Ser Ala Val Trp Asp Pro Ala Lys Asn Met
        355                 360                 365

```
Leu Phe Asp Ala Val Ser Gly Gln Lys Asp Ala Lys Thr Ala Ala Asn
        370                 375                 380

Asp Ala Val Thr Leu Ile Lys Glu Thr Ile Lys Gln Lys Phe Gly Glu
385                 390                 395                 400

<210> SEQ ID NO 11
<211> LENGTH: 648
<212> TYPE: PRT
<213> ORGANISM: Streptococcus pneumoniae

<400> SEQUENCE: 11

Met Ser Gly Thr Ser Met Ala Thr Pro Ile Val Ala Ala Ser Thr Val
1               5                   10                  15

Leu Ile Arg Pro Lys Leu Lys Glu Met Leu Glu Arg Pro Val Leu Lys
            20                  25                  30

Asn Leu Lys Gly Asp Asp Lys Ile Asp Leu Thr Ser Leu Thr Lys Ile
        35                  40                  45

Ala Leu Gln Asn Thr Ala Arg Pro Met Met Asp Ala Thr Ser Trp Lys
    50                  55                  60

Glu Lys Ser Gln Tyr Phe Ala Ser Pro Arg Gln Gln Gly Ala Gly Leu
65                  70                  75                  80

Ile Asn Val Ala Asn Ala Leu Arg Asn Glu Val Val Ala Thr Phe Lys
                85                  90                  95

Asn Thr Asp Ser Lys Gly Leu Val Asn Ser Tyr Gly Ser Ile Ser Leu
            100                 105                 110

Lys Glu Ile Lys Gly Asp Lys Lys Tyr Phe Thr Ile Lys Leu His Asn
        115                 120                 125

Thr Ser Asn Arg Pro Leu Thr Phe Lys Val Ser Ala Ser Ala Ile Thr
    130                 135                 140

Thr Asp Ser Leu Thr Asp Arg Leu Lys Leu Asp Glu Thr Tyr Lys Asp
145                 150                 155                 160

Glu Lys Ser Pro Asp Gly Lys Gln Ile Val Pro Glu Ile His Pro Glu
                165                 170                 175

Lys Val Lys Gly Ala Asn Ile Thr Phe Glu His Asp Thr Phe Thr Ile
            180                 185                 190

Gly Ala Asn Ser Ser Phe Asp Leu Asn Ala Val Ile Asn Val Gly Glu
        195                 200                 205

Ala Lys Asn Lys Asn Lys Phe Val Glu Ser Phe Ile His Phe Glu Ser
    210                 215                 220

Val Glu Glu Met Glu Ala Leu Asn Ser Asn Gly Lys Lys Ile Asn Phe
225                 230                 235                 240

Gln Pro Ser Leu Ser Met Pro Leu Met Gly Phe Ala Gly Asn Trp Asn
                245                 250                 255

His Glu Pro Ile Leu Asp Lys Trp Ala Trp Glu Glu Gly Ser Arg Ser
            260                 265                 270

Lys Thr Leu Gly Gly Tyr Asp Asp Gly Lys Pro Lys Ile Pro Gly
        275                 280                 285

Thr Leu Asn Lys Gly Ile Gly Gly Glu His Gly Ile Asp Lys Phe Asn
    290                 295                 300

Pro Ala Gly Val Ile Gln Asn Arg Lys Asp Lys Asn Thr Thr Ser Leu
305                 310                 315                 320

Asp Gln Asn Pro Glu Leu Phe Ala Phe Asn Asn Glu Gly Ile Asn Ala
                325                 330                 335

Pro Ser Ser Ser Gly Ser Lys Ile Ala Asn Ile Tyr Pro Leu Asp Ser
```

```
            340                 345                 350
Asn Gly Asn Pro Gln Asp Ala Gln Leu Glu Arg Gly Leu Thr Pro Ser
        355                 360                 365

Pro Leu Val Leu Arg Ser Ala Glu Glu Gly Leu Ile Ser Ile Val Asn
    370                 375                 380

Thr Asn Lys Glu Gly Glu Asn Gln Arg Asp Leu Lys Val Ile Ser Arg
385                 390                 395                 400

Glu His Phe Ile Arg Gly Ile Leu Asn Ser Lys Ser Asn Asp Ala Lys
                405                 410                 415

Gly Ile Lys Ser Ser Lys Leu Lys Val Trp Gly Asp Leu Lys Trp Asp
            420                 425                 430

Gly Leu Ile Tyr Asn Pro Arg Gly Arg Glu Glu Asn Ala Pro Glu Ser
        435                 440                 445

Lys Asp Asn Gln Asp Pro Ala Thr Lys Ile Arg Gly Gln Phe Glu Pro
    450                 455                 460

Ile Ala Glu Gly Gln Tyr Phe Tyr Lys Phe Lys Tyr Arg Leu Thr Lys
465                 470                 475                 480

Asp Tyr Pro Trp Gln Val Ser Tyr Ile Pro Val Lys Ile Asp Asn Thr
                485                 490                 495

Ala Pro Lys Ile Val Ser Val Asp Phe Ser Asn Pro Glu Lys Ile Lys
            500                 505                 510

Leu Ile Thr Lys Asp Thr Tyr His Lys Val Lys Asp Gln Tyr Lys Asn
        515                 520                 525

Glu Thr Leu Phe Ala Arg Asp Gln Lys Glu His Pro Glu Lys Phe Asp
    530                 535                 540

Glu Ile Ala Asn Glu Val Trp Tyr Ala Gly Ala Ala Leu Val Asn Glu
545                 550                 555                 560

Asp Gly Glu Val Glu Lys Asn Leu Glu Val Thr Tyr Ala Gly Glu Gly
                565                 570                 575

Gln Gly Arg Asn Arg Lys Leu Asp Lys Asp Gly Asn Thr Ile Tyr Glu
            580                 585                 590

Ile Lys Gly Ala Gly Asp Leu Arg Gly Lys Ile Ile Glu Val Ile Ala
        595                 600                 605

Leu Asp Gly Ser Ser Asn Phe Thr Lys Ile His Arg Ile Lys Phe Ala
    610                 615                 620

Asn Gln Ala Asp Glu Lys Gly Met Ile Ser Tyr Tyr Leu Val Asp Pro
625                 630                 635                 640

Asp Gln Asp Ser Ser Lys Tyr Gln
                645

<210> SEQ ID NO 12
<211> LENGTH: 2140
<212> TYPE: PRT
<213> ORGANISM: Streptococcus pneumoniae

<400> SEQUENCE: 12

Met Lys Lys Ser Thr Val Leu Ser Leu Thr Thr Ala Ala Val Ile Leu
1               5                   10                  15

Ala Ala Tyr Ala Pro Asn Glu Val Val Leu Ala Asp Thr Ser Ser Ser
                20                  25                  30

Glu Asp Ala Leu Asn Ile Ser Asp Lys Glu Lys Val Ala Glu Asn Lys
            35                  40                  45

Glu Lys His Glu Asn Ile His Ser Ala Met Glu Thr Ser Gln Asp Phe
        50                  55                  60
```

-continued

Lys Glu Lys Lys Thr Ala Val Ile Lys Glu Lys Val Val Ser Lys
65                  70                  75                  80

Asn Pro Val Ile Asp Asn Thr Ser Asn Glu Glu Ala Lys Ile Lys
            85                  90                  95

Glu Glu Asn Ser Asn Lys Ser Gln Gly Asp Tyr Thr Asp Ser Phe Val
            100                 105                 110

Asn Lys Asn Thr Glu Asn Pro Lys Lys Glu Asp Lys Val Val Tyr Ile
            115                 120                 125

Ala Glu Phe Lys Asp Lys Glu Ser Gly Lys Ala Ile Lys Glu Leu
            130                 135                 140

Ser Ser Leu Lys Asn Thr Lys Val Leu Tyr Thr Tyr Asp Arg Ile Phe
145                 150                 155                 160

Asn Gly Ser Ala Ile Glu Thr Thr Pro Asp Asn Leu Asp Lys Ile Lys
                165                 170                 175

Gln Ile Glu Gly Ile Ser Ser Val Glu Arg Ala Gln Lys Val Gln Pro
                180                 185                 190

Met Met Asn His Ala Arg Lys Glu Ile Gly Val Glu Glu Ala Ile Asp
                195                 200                 205

Tyr Leu Lys Ser Ile Asn Ala Pro Phe Gly Lys Asn Phe Asp Gly Arg
    210                 215                 220

Gly Met Val Ile Ser Asn Ile Asp Thr Gly Thr Asp Tyr Arg His Lys
225                 230                 235                 240

Ala Met Arg Ile Asp Asp Ala Lys Ala Ser Met Arg Phe Lys Lys
                245                 250                 255

Glu Asp Leu Lys Gly Thr Asp Lys Asn Tyr Trp Leu Ser Asp Lys Ile
            260                 265                 270

Pro His Ala Phe Asn Tyr Tyr Asn Gly Gly Lys Ile Thr Val Glu Lys
            275                 280                 285

Tyr Asp Asp Gly Arg Asp Tyr Phe Asp Pro His Gly Met His Ile Ala
            290                 295                 300

Gly Ile Leu Ala Gly Asn Asp Thr Glu Gln Asp Ile Lys Asn Phe Asn
305                 310                 315                 320

Gly Ile Asp Gly Ile Ala Pro Asn Ala Gln Ile Phe Ser Tyr Lys Met
                325                 330                 335

Tyr Ser Asp Ala Gly Ser Gly Phe Ala Gly Asp Glu Thr Met Phe His
            340                 345                 350

Ala Ile Glu Asp Ser Ile Lys His Asn Val Asp Val Val Ser Val Ser
            355                 360                 365

Ser Gly Phe Thr Gly Thr Gly Leu Val Gly Glu Lys Tyr Trp Gln Ala
    370                 375                 380

Ile Arg Ala Leu Arg Lys Ala Gly Ile Pro Met Val Val Ala Thr Gly
385                 390                 395                 400

Asn Tyr Ala Thr Ser Ala Ser Ser Ser Trp Asp Leu Val Ala Asn
            405                 410                 415

Asn His Leu Lys Met Thr Asp Thr Gly Asn Val Thr Arg Thr Ala Ala
            420                 425                 430

His Glu Asp Ala Ile Ala Val Ala Ser Ala Lys Asn Gln Thr Val Glu
            435                 440                 445

Phe Asp Lys Val Asn Ile Gly Gly Glu Ser Phe Lys Tyr Arg Asn Ile
            450                 455                 460

Gly Ala Phe Phe Asp Lys Ser Lys Ile Thr Thr Asn Glu Asp Gly Thr
465                 470                 475                 480

Lys Ala Pro Ser Lys Leu Lys Phe Val Tyr Ile Gly Lys Gly Gln Asp

```
            485                 490                 495
Gln Asp Leu Ile Gly Leu Asp Leu Arg Gly Lys Ile Ala Val Met Asp
            500                 505                 510

Arg Ile Tyr Thr Lys Asp Leu Lys Asn Ala Phe Lys Lys Ala Met Asp
            515                 520                 525

Lys Gly Ala Arg Ala Ile Met Val Val Asn Thr Val Asn Tyr Asn
            530                 535                 540

Arg Asp Asn Trp Thr Glu Leu Pro Ala Met Gly Tyr Glu Ala Asp Glu
545                 550                 555                 560

Gly Thr Lys Ser Gln Val Phe Ser Ile Ser Gly Asp Asp Gly Val Lys
                565                 570                 575

Leu Trp Asn Met Ile Asn Pro Asp Lys Lys Thr Glu Val Lys Arg Asn
                580                 585                 590

Asn Lys Glu Asp Phe Lys Asp Lys Leu Glu Gln Tyr Tyr Pro Ile Asp
                595                 600                 605

Met Glu Ser Phe Asn Ser Asn Lys Pro Asn Val Gly Asp Glu Lys Glu
                610                 615                 620

Ile Asp Phe Lys Phe Ala Pro Asp Thr Asp Lys Glu Leu Tyr Lys Glu
625                 630                 635                 640

Asp Ile Ile Val Pro Ala Gly Ser Thr Ser Trp Gly Pro Arg Ile Asp
                645                 650                 655

Leu Leu Leu Lys Pro Asp Val Ser Ala Pro Gly Lys Asn Ile Lys Ser
                660                 665                 670

Thr Leu Asn Val Ile Asn Gly Lys Ser Thr Tyr Gly Tyr Met Ser Gly
                675                 680                 685

Thr Ser Met Ala Thr Pro Ile Val Ala Ala Ser Thr Val Leu Ile Arg
                690                 695                 700

Pro Lys Leu Lys Glu Met Leu Glu Arg Pro Val Leu Lys Asn Leu Lys
705                 710                 715                 720

Gly Asp Asp Lys Ile Asp Leu Thr Ser Leu Thr Lys Ile Ala Leu Gln
                725                 730                 735

Asn Thr Ala Arg Pro Met Met Asp Ala Thr Ser Trp Lys Glu Lys Ser
                740                 745                 750

Gln Tyr Phe Ala Ser Pro Arg Gln Gln Gly Ala Gly Leu Ile Asn Val
                755                 760                 765

Ala Asn Ala Leu Arg Asn Glu Val Val Ala Thr Phe Lys Asn Thr Asp
                770                 775                 780

Ser Lys Gly Leu Val Asn Ser Tyr Gly Ser Ile Ser Leu Lys Glu Ile
785                 790                 795                 800

Lys Gly Asp Lys Lys Tyr Phe Thr Ile Lys Leu His Asn Thr Ser Asn
                805                 810                 815

Arg Pro Leu Thr Phe Lys Val Ser Ala Ser Ala Ile Thr Thr Asp Ser
                820                 825                 830

Leu Thr Asp Arg Leu Lys Leu Asp Glu Thr Tyr Lys Asp Glu Lys Ser
                835                 840                 845

Pro Asp Gly Lys Gln Ile Val Pro Glu Ile His Pro Glu Lys Val Lys
                850                 855                 860

Gly Ala Asn Ile Thr Phe Glu His Asp Thr Phe Thr Ile Gly Ala Asn
865                 870                 875                 880

Ser Ser Phe Asp Leu Asn Ala Val Ile Asn Val Gly Glu Ala Lys Asn
                885                 890                 895

Lys Asn Lys Phe Val Glu Ser Phe Ile His Phe Glu Ser Val Glu Glu
                900                 905                 910
```

```
Met Glu Ala Leu Asn Ser Asn Gly Lys Lys Ile Asn Phe Gln Pro Ser
            915                 920                 925
Leu Ser Met Pro Leu Met Gly Phe Ala Gly Asn Trp Asn His Glu Pro
            930                 935                 940
Ile Leu Asp Lys Trp Ala Trp Glu Gly Ser Arg Ser Lys Thr Leu
945                 950                 955                 960
Gly Gly Tyr Asp Asp Asp Gly Lys Pro Lys Ile Pro Gly Thr Leu Asn
            965                 970                 975
Lys Gly Ile Gly Gly Glu His Gly Ile Asp Lys Phe Asn Pro Ala Gly
            980                 985                 990
Val Ile Gln Asn Arg Lys Asp Lys Asn Thr Thr Ser Leu Asp Gln Asn
            995                 1000                1005
Pro Glu Leu Phe Ala Phe Asn Asn Glu Gly Ile Asn Ala Pro Ser
    1010                1015                1020
Ser Ser Gly Ser Lys Ile Ala Asn Ile Tyr Pro Leu Asp Ser Asn
    1025                1030                1035
Gly Asn Pro Gln Asp Ala Gln Leu Glu Arg Gly Leu Thr Pro Ser
    1040                1045                1050
Pro Leu Val Leu Arg Ser Ala Glu Glu Gly Leu Ile Ser Ile Val
    1055                1060                1065
Asn Thr Asn Lys Glu Gly Glu Asn Gln Arg Asp Leu Lys Val Ile
    1070                1075                1080
Ser Arg Glu His Phe Ile Arg Gly Ile Leu Asn Ser Lys Ser Asn
    1085                1090                1095
Asp Ala Lys Gly Ile Lys Ser Ser Lys Leu Lys Val Trp Gly Asp
    1100                1105                1110
Leu Lys Trp Asp Gly Leu Ile Tyr Asn Pro Arg Gly Arg Glu Glu
    1115                1120                1125
Asn Ala Pro Glu Ser Lys Asp Asn Gln Asp Pro Ala Thr Lys Ile
    1130                1135                1140
Arg Gly Gln Phe Glu Pro Ile Ala Glu Gly Gln Tyr Phe Tyr Lys
    1145                1150                1155
Phe Lys Tyr Arg Leu Thr Lys Asp Tyr Pro Trp Gln Val Ser Tyr
    1160                1165                1170
Ile Pro Val Lys Ile Asp Asn Thr Ala Pro Lys Ile Val Ser Val
    1175                1180                1185
Asp Phe Ser Asn Pro Glu Lys Ile Lys Leu Ile Thr Lys Asp Thr
    1190                1195                1200
Tyr His Lys Val Lys Asp Gln Tyr Lys Asn Glu Thr Leu Phe Ala
    1205                1210                1215
Arg Asp Gln Lys Glu His Pro Glu Lys Phe Asp Glu Ile Ala Asn
    1220                1225                1230
Glu Val Trp Tyr Ala Gly Ala Ala Leu Val Asn Glu Asp Gly Glu
    1235                1240                1245
Val Glu Lys Asn Leu Glu Val Thr Tyr Ala Gly Glu Gly Gln Gly
    1250                1255                1260
Arg Asn Arg Lys Leu Asp Lys Asp Gly Asn Thr Ile Tyr Glu Ile
    1265                1270                1275
Lys Gly Ala Gly Asp Leu Arg Gly Lys Ile Ile Glu Val Ile Ala
    1280                1285                1290
Leu Asp Gly Ser Ser Asn Phe Thr Lys Ile His Arg Ile Lys Phe
    1295                1300                1305
```

```
Ala Asn Gln Ala Asp Glu Lys Gly Met Ile Ser Tyr Tyr Leu Val
1310                1315                1320

Asp Pro Asp Gln Asp Ser Ser Lys Tyr Gln Lys Leu Gly Glu Ile
    1325                1330                1335

Ala Glu Ser Lys Phe Lys Asn Leu Gly Asn Gly Lys Glu Gly Ser
1340                1345                1350

Leu Lys Lys Asp Thr Thr Gly Val Glu His His His Gln Glu Asn
    1355                1360                1365

Glu Glu Ser Ile Lys Glu Lys Ser Ser Phe Thr Ile Asp Arg Asn
1370                1375                1380

Ile Ser Thr Ile Arg Asp Phe Glu Asn Lys Asp Leu Lys Lys Leu
    1385                1390                1395

Ile Lys Lys Lys Phe Arg Glu Val Asp Asp Phe Thr Ser Glu Thr
1400                1405                1410

Gly Lys Arg Met Glu Glu Tyr Asp Tyr Lys Tyr Asp Asp Lys Gly
    1415                1420                1425

Asn Ile Ile Ala Tyr Asp Asp Gly Thr Asp Leu Glu Tyr Glu Thr
1430                1435                1440

Glu Lys Leu Asp Glu Ile Lys Ser Lys Ile Tyr Gly Val Leu Ser
    1445                1450                1455

Pro Ser Lys Asp Gly His Phe Glu Ile Leu Gly Lys Ile Ser Asn
1460                1465                1470

Val Ser Lys Asn Ala Lys Val Tyr Tyr Gly Asn Asn Tyr Lys Ser
    1475                1480                1485

Ile Glu Ile Lys Ala Thr Lys Tyr Asp Phe His Ser Lys Thr Met
1490                1495                1500

Thr Phe Asp Leu Tyr Ala Asn Ile Asn Asp Ile Val Asp Gly Leu
    1505                1510                1515

Ala Phe Ala Gly Asp Met Arg Leu Phe Val Lys Asp Asn Asp Gln
1520                1525                1530

Lys Lys Ala Glu Ile Lys Ile Arg Met Pro Glu Lys Ile Lys Glu
    1535                1540                1545

Thr Lys Ser Glu Tyr Pro Tyr Val Ser Ser Tyr Gly Asn Val Ile
1550                1555                1560

Glu Leu Gly Glu Gly Asp Leu Ser Lys Asn Lys Pro Asp Asn Leu
    1565                1570                1575

Thr Lys Met Glu Ser Gly Lys Ile Tyr Ser Asp Ser Glu Lys Gln
1580                1585                1590

Gln Tyr Leu Leu Lys Asp Asn Ile Ile Leu Arg Lys Gly Tyr Ala
    1595                1600                1605

Leu Lys Val Thr Thr Tyr Asn Pro Gly Lys Thr Asp Met Leu Glu
1610                1615                1620

Gly Asn Gly Val Tyr Ser Lys Glu Asp Ile Ala Lys Ile Gln Lys
    1625                1630                1635

Ala Asn Pro Asn Leu Arg Ala Leu Ser Glu Thr Thr Ile Tyr Ala
1640                1645                1650

Asp Ser Arg Asn Val Glu Asp Gly Arg Ser Thr Gln Ser Val Leu
    1655                1660                1665

Met Ser Ala Leu Asp Gly Phe Asn Ile Ile Arg Tyr Gln Val Phe
1670                1675                1680

Thr Phe Lys Met Asn Asp Lys Gly Glu Ala Ile Asp Lys Asp Gly
    1685                1690                1695

Asn Leu Val Thr Asp Ser Ser Lys Leu Val Leu Phe Gly Lys Asp
```

-continued

```
            1700                1705                1710
Asp Lys Glu Tyr Thr Gly Glu Asp Lys Phe Asn Val Glu Ala Ile
            1715                1720                1725

Lys Glu Asp Gly Ser Met Leu Phe Ile Asp Thr Lys Pro Val Asn
            1730                1735                1740

Leu Ser Met Asp Lys Asn Tyr Phe Asn Pro Ser Lys Ser Asn Lys
            1745                1750                1755

Ile Tyr Val Arg Asn Pro Glu Phe Tyr Leu Arg Gly Lys Ile Ser
            1760                1765                1770

Asp Lys Gly Gly Phe Asn Trp Glu Leu Arg Val Asn Glu Ser Val
            1775                1780                1785

Val Asp Asn Tyr Leu Ile Tyr Gly Asp Leu His Ile Asp Asn Thr
            1790                1795                1800

Arg Asp Phe Asn Ile Lys Leu Asn Val Lys Asp Gly Asp Ile Met
            1805                1810                1815

Asp Trp Gly Met Lys Asp Tyr Lys Ala Asn Gly Phe Pro Asp Lys
            1820                1825                1830

Val Thr Asp Met Asp Gly Asn Val Tyr Leu Gln Thr Gly Tyr Ser
            1835                1840                1845

Asp Leu Asn Ala Lys Ala Val Gly Val His Tyr Gln Phe Leu Tyr
            1850                1855                1860

Asp Asn Val Lys Pro Glu Val Asn Ile Asp Pro Lys Gly Asn Thr
            1865                1870                1875

Ser Ile Glu Tyr Ala Asp Gly Lys Ser Val Val Phe Asn Ile Asn
            1880                1885                1890

Asp Lys Arg Asn Asn Gly Phe Asp Gly Glu Ile Gln Glu Gln His
            1895                1900                1905

Ile Tyr Ile Asn Gly Lys Glu Tyr Thr Ser Phe Asn Asp Ile Lys
            1910                1915                1920

Gln Ile Ile Asp Lys Thr Leu Asn Ile Lys Ile Val Val Lys Asp
            1925                1930                1935

Phe Ala Arg Asn Thr Thr Val Lys Glu Phe Ile Leu Asn Lys Asp
            1940                1945                1950

Thr Gly Glu Val Ser Glu Leu Lys Pro His Arg Val Thr Val Thr
            1955                1960                1965

Ile Gln Asn Gly Lys Glu Met Ser Ser Thr Ile Val Ser Glu Glu
            1970                1975                1980

Asp Phe Ile Leu Pro Val Tyr Lys Gly Glu Leu Glu Lys Gly Tyr
            1985                1990                1995

Gln Phe Asp Gly Trp Glu Ile Ser Gly Phe Glu Gly Lys Lys Asp
            2000                2005                2010

Ala Gly Tyr Val Ile Asn Leu Ser Lys Asp Thr Phe Ile Lys Pro
            2015                2020                2025

Val Phe Lys Lys Ile Glu Glu Lys Lys Glu Glu Asn Lys Pro
            2030                2035                2040

Thr Phe Asp Val Ser Lys Lys Lys Asp Asn Pro Gln Val Asn His
            2045                2050                2055

Ser Gln Leu Asn Glu Ser His Arg Lys Glu Asp Leu Gln Arg Glu
            2060                2065                2070

Glu His Ser Gln Lys Ser Asp Ser Thr Lys Asp Val Thr Ala Thr
            2075                2080                2085

Val Leu Asp Lys Asn Asn Ile Ser Ser Lys Ser Thr Thr Asn Asn
            2090                2095                2100
```

Pro Asn Lys Leu Pro Lys Thr Gly Thr Ala Ser Gly Ala Gln Thr
            2105                2110                2115

Leu Leu Ala Ala Gly Ile Met Phe Ile Val Gly Ile Phe Leu Gly
            2120                2125                2130

Leu Lys Lys Lys Asn Gln Asp
            2135            2140

<210> SEQ ID NO 13
<211> LENGTH: 662
<212> TYPE: PRT
<213> ORGANISM: Streptococcus pneumoniae

<400> SEQUENCE: 13

Met Val Val Leu Ala Asp Thr Ser Ser Glu Asp Ala Leu Asn Ile
1               5                   10                  15

Ser Asp Lys Glu Lys Val Ala Glu Asn Lys Glu Lys His Glu Asn Ile
                20                  25                  30

His Ser Ala Met Glu Thr Ser Gln Asp Phe Lys Glu Lys Lys Thr Ala
            35                  40                  45

Val Ile Lys Glu Lys Glu Val Val Ser Lys Asn Pro Val Ile Asp Asn
    50                  55                  60

Asn Thr Ser Asn Glu Glu Ala Lys Ile Lys Glu Glu Asn Ser Asn Lys
65                  70                  75                  80

Ser Gln Gly Asp Tyr Thr Asp Ser Phe Val Asn Lys Asn Thr Glu Asn
                85                  90                  95

Pro Lys Lys Glu Asp Lys Val Val Tyr Ile Ala Glu Phe Lys Asp Lys
            100                 105                 110

Glu Ser Gly Glu Lys Ala Ile Lys Glu Leu Ser Ser Leu Lys Asn Thr
        115                 120                 125

Lys Val Leu Tyr Thr Tyr Asp Arg Ile Phe Asn Gly Ser Ala Ile Glu
130                 135                 140

Thr Thr Pro Asp Asn Leu Asp Lys Ile Lys Gln Ile Glu Gly Ile Ser
145                 150                 155                 160

Ser Val Glu Arg Ala Gln Lys Val Gln Pro Met Met Asn His Ala Arg
                165                 170                 175

Lys Glu Ile Gly Val Glu Glu Ala Ile Asp Tyr Leu Lys Ser Ile Asn
            180                 185                 190

Ala Pro Phe Gly Lys Asn Phe Asp Gly Arg Gly Met Val Ile Ser Asn
        195                 200                 205

Ile Asp Thr Gly Thr Asp Tyr Arg His Lys Ala Met Arg Ile Asp Asp
210                 215                 220

Asp Ala Lys Ala Ser Met Arg Phe Lys Lys Glu Asp Leu Lys Gly Thr
225                 230                 235                 240

Asp Lys Asn Tyr Trp Leu Ser Asp Lys Ile Pro His Ala Phe Asn Tyr
                245                 250                 255

Tyr Asn Gly Gly Lys Ile Thr Val Glu Lys Tyr Asp Asp Gly Arg Asp
            260                 265                 270

Tyr Phe Asp Pro His Gly Met His Ile Ala Gly Ile Leu Ala Gly Asn
        275                 280                 285

Asp Thr Glu Gln Asp Ile Lys Asn Phe Asn Gly Ile Asp Gly Ile Ala
        290                 295                 300

Pro Asn Ala Gln Ile Phe Ser Tyr Lys Met Tyr Ser Asp Ala Gly Ser
305                 310                 315                 320

Gly Phe Ala Gly Asp Glu Thr Met Phe His Ala Ile Glu Asp Ser Ile

```
                325                 330                 335
Lys His Asn Val Asp Val Val Ser Val Ser Ser Gly Phe Thr Gly Thr
            340                 345                 350

Gly Leu Val Gly Glu Lys Tyr Trp Gln Ala Ile Arg Ala Leu Arg Lys
        355                 360                 365

Ala Gly Ile Pro Met Val Val Ala Thr Gly Asn Tyr Ala Thr Ser Ala
    370                 375                 380

Ser Ser Ser Ser Trp Asp Leu Val Ala Asn Asn His Leu Lys Met Thr
385                 390                 395                 400

Asp Thr Gly Asn Val Thr Arg Thr Ala Ala His Glu Asp Ala Ile Ala
                405                 410                 415

Val Ala Ser Ala Lys Asn Gln Thr Val Glu Phe Asp Lys Val Asn Ile
            420                 425                 430

Gly Gly Glu Ser Phe Lys Tyr Arg Asn Ile Gly Ala Phe Phe Asp Lys
        435                 440                 445

Ser Lys Ile Thr Thr Asn Glu Asp Gly Thr Lys Ala Pro Ser Lys Leu
    450                 455                 460

Lys Phe Val Tyr Ile Gly Lys Gly Gln Asp Gln Asp Leu Ile Gly Leu
465                 470                 475                 480

Asp Leu Arg Gly Lys Ile Ala Val Met Asp Arg Ile Tyr Thr Lys Asp
                485                 490                 495

Leu Lys Asn Ala Phe Lys Lys Ala Met Asp Lys Gly Ala Arg Ala Ile
            500                 505                 510

Met Val Val Asn Thr Val Asn Tyr Tyr Asn Arg Asp Asn Trp Thr Glu
        515                 520                 525

Leu Pro Ala Met Gly Tyr Glu Ala Asp Glu Gly Thr Lys Ser Gln Val
    530                 535                 540

Phe Ser Ile Ser Gly Asp Asp Gly Val Lys Leu Trp Asn Met Ile Asn
545                 550                 555                 560

Pro Asp Lys Lys Thr Glu Val Lys Arg Asn Asn Lys Glu Asp Phe Lys
                565                 570                 575

Asp Lys Leu Glu Gln Tyr Tyr Pro Ile Asp Met Glu Ser Phe Asn Ser
            580                 585                 590

Asn Lys Pro Asn Val Gly Asp Glu Lys Glu Ile Asp Phe Lys Phe Ala
        595                 600                 605

Pro Asp Thr Asp Lys Glu Leu Tyr Lys Glu Asp Ile Ile Val Pro Ala
    610                 615                 620

Gly Ser Thr Ser Trp Gly Pro Arg Ile Asp Leu Leu Leu Lys Pro Asp
625                 630                 635                 640

Val Ser Ala Pro Gly Lys Asn Ile Lys Ser Thr Leu Asn Val Ile Asn
                645                 650                 655

Gly Lys Ser Thr Tyr Gly
            660

<210> SEQ ID NO 14
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or Ile
<220> FEATURE:
<221> NAME/KEY: MOD_RES
```

```
<222> LOCATION: (55)..(55)
<223> OTHER INFORMATION: Asn or Tyr
<220> FEATURE:
<221> NAME/KEY: MOD_RES
<222> LOCATION: (63)..(63)
<223> OTHER INFORMATION: His or Tyr
<220> FEATURE:
<221> NAME/KEY: MOD_RES
<222> LOCATION: (79)..(79)
<223> OTHER INFORMATION: Arg or His
<220> FEATURE:
<221> NAME/KEY: MOD_RES
<222> LOCATION: (97)..(97)
<223> OTHER INFORMATION: Ala or Glu
<220> FEATURE:
<221> NAME/KEY: MOD_RES
<222> LOCATION: (108)..(108)
<223> OTHER INFORMATION: Gly or Glu
<220> FEATURE:
<221> NAME/KEY: MOD_RES
<222> LOCATION: (164)..(164)
<223> OTHER INFORMATION: Asp or Glu
<220> FEATURE:
<221> NAME/KEY: MOD_RES
<222> LOCATION: (165)..(165)
<223> OTHER INFORMATION: Gln or Lys
<220> FEATURE:
<221> NAME/KEY: MOD_RES
<222> LOCATION: (187)..(187)
<223> OTHER INFORMATION: Phe or Ile
<220> FEATURE:
<221> NAME/KEY: MOD_RES
<222> LOCATION: (197)..(197)
<223> OTHER INFORMATION: Arg or His
<220> FEATURE:
<221> NAME/KEY: MOD_RES
<222> LOCATION: (238)..(238)
<223> OTHER INFORMATION: Gly or Arg

<400> SEQUENCE: 14

Xaa Asn Gln Ser Tyr Phe Tyr Leu Lys Met Lys Glu His Lys Leu Lys
1               5                   10                  15

Val Pro Tyr Thr Gly Lys Glu Arg Arg Val Arg Ile Leu Leu Pro Lys
            20                  25                  30

Asp Tyr Glu Lys Asp Thr Asp Arg Ser Tyr Pro Val Val Tyr Phe His
        35                  40                  45

Asp Gly Gln Asn Val Phe Xaa Ser Lys Glu Ser Phe Ile Gly Xaa Ser
    50                  55                  60

Trp Lys Ile Ile Pro Ala Ile Lys Arg Asn Pro Asp Ile Ser Xaa Met
65                  70                  75                  80

Ile Val Val Ala Ile Asp Asn Asp Gly Met Gly Arg Met Asn Glu Tyr
                85                  90                  95

Xaa Ala Trp Lys Phe Gln Glu Ser Pro Ile Pro Xaa Gln Gln Phe Gly
            100                 105                 110

Gly Lys Gly Val Glu Tyr Ala Glu Phe Val Met Glu Val Lys Pro
        115                 120                 125

Phe Ile Asp Glu Thr Tyr Arg Thr Lys Ala Asp Cys Gln His Thr Ala
    130                 135                 140

Met Ile Gly Ser Ser Leu Gly Gly Asn Ile Thr Gln Phe Ile Gly Leu
145                 150                 155                 160

Glu Tyr Gln Xaa Xaa Ile Gly Cys Leu Gly Val Phe Ser Ala Asn
            165                 170                 175

Trp Leu His Gln Glu Ala Phe Asn Arg Tyr Xaa Glu Cys Gln Lys Leu
        180                 185                 190

Ser Pro Asp Gln Xaa Ile Phe Ile Tyr Val Gly Thr Glu Glu Ala Asp
    195                 200                 205
```

```
Asp Thr Asp Lys Thr Leu Met Asp Gly Asn Ile Lys Gln Ala Tyr Ile
        210                 215                 220
Asp Ser Ser Leu Cys Tyr Tyr His Asp Leu Ile Ala Gly Xaa Val His
225                 230                 235                 240
Leu Asp Asn Leu Val Leu Lys Val Gln Ser Gly Ala Ile His Ser Glu
                245                 250                 255
Ile Pro Trp Ser Glu Asn Leu Pro Asp Cys Leu Arg Phe Phe Ala Glu
            260                 265                 270
Lys Trp

<210> SEQ ID NO 15
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or Ile
<220> FEATURE:
<221> NAME/KEY: MOD_RES
<222> LOCATION: (55)..(55)
<223> OTHER INFORMATION: Asn or Tyr
<220> FEATURE:
<221> NAME/KEY: MOD_RES
<222> LOCATION: (63)..(63)
<223> OTHER INFORMATION: His or Tyr
<220> FEATURE:
<221> NAME/KEY: MOD_RES
<222> LOCATION: (79)..(79)
<223> OTHER INFORMATION: Arg or His
<220> FEATURE:
<221> NAME/KEY: MOD_RES
<222> LOCATION: (97)..(97)
<223> OTHER INFORMATION: Ala or Glu
<220> FEATURE:
<221> NAME/KEY: MOD_RES
<222> LOCATION: (108)..(108)
<223> OTHER INFORMATION: Gly or Glu

<400> SEQUENCE: 15

Xaa Asn Gln Ser Tyr Phe Tyr Leu Lys Met Lys Glu His Lys Leu Lys
1               5                   10                  15
Val Pro Tyr Thr Gly Lys Glu Arg Arg Val Arg Ile Leu Leu Pro Lys
            20                  25                  30
Asp Tyr Glu Lys Asp Thr Asp Arg Ser Tyr Pro Val Val Tyr Phe His
        35                  40                  45
Asp Gly Gln Asn Val Phe Xaa Ser Lys Glu Ser Phe Ile Gly Xaa Ser
    50                  55                  60
Trp Lys Ile Ile Pro Ala Ile Lys Arg Asn Pro Asp Ile Ser Xaa Met
65                  70                  75                  80
Ile Val Val Ala Ile Asp Asn Asp Gly Met Gly Arg Met Asn Glu Tyr
                85                  90                  95
Xaa Ala Trp Lys Phe Gln Glu Ser Pro Ile Pro Xaa Gln Gln Phe Gly
            100                 105                 110
Gly Lys Gly Val Glu Tyr Ala Glu Phe Val Met Glu Val Val Lys Pro
        115                 120                 125
Phe Ile
    130

<210> SEQ ID NO 16
```

```
<211> LENGTH: 299
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Met or Thr
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (15)..(15)
<223> OTHER INFORMATION: Ala or Val
<220> FEATURE:
<221> NAME/KEY: MOD_RES
<222> LOCATION: (26)..(26)
<223> OTHER INFORMATION: Met or Ile
<220> FEATURE:
<221> NAME/KEY: MOD_RES
<222> LOCATION: (80)..(80)
<223> OTHER INFORMATION: Asn or Tyr
<220> FEATURE:
<221> NAME/KEY: MOD_RES
<222> LOCATION: (88)..(88)
<223> OTHER INFORMATION: His or Tyr
<220> FEATURE:
<221> NAME/KEY: MOD_RES
<222> LOCATION: (104)..(104)
<223> OTHER INFORMATION: Arg or His
<220> FEATURE:
<221> NAME/KEY: MOD_RES
<222> LOCATION: (122)..(122)
<223> OTHER INFORMATION: Ala or Glu
<220> FEATURE:
<221> NAME/KEY: MOD_RES
<222> LOCATION: (133)..(133)
<223> OTHER INFORMATION: Gly or Glu
<220> FEATURE:
<221> NAME/KEY: MOD_RES
<222> LOCATION: (189)..(189)
<223> OTHER INFORMATION: Asp or Glu
<220> FEATURE:
<221> NAME/KEY: MOD_RES
<222> LOCATION: (190)..(190)
<223> OTHER INFORMATION: Gln or Lys
<220> FEATURE:
<221> NAME/KEY: MOD_RES
<222> LOCATION: (212)..(212)
<223> OTHER INFORMATION: Phe or Ile
<220> FEATURE:
<221> NAME/KEY: MOD_RES
<222> LOCATION: (222)..(222)
<223> OTHER INFORMATION: Arg or His
<220> FEATURE:
<221> NAME/KEY: MOD_RES
<222> LOCATION: (263)..(263)
<223> OTHER INFORMATION: Arg or His

<400> SEQUENCE: 16

Met Ser Ser Lys Phe Xaa Lys Ser Xaa Ala Val Leu Gly Thr Xaa Thr
1               5                   10                  15

Leu Ala Ser Leu Leu Leu Val Ala Cys Xaa Asn Gln Ser Tyr Phe Tyr
                20                  25                  30

Leu Lys Met Lys Glu His Lys Leu Lys Val Pro Tyr Thr Gly Lys Glu
            35                  40                  45

Arg Arg Val Arg Ile Leu Leu Pro Lys Asp Tyr Glu Lys Asp Thr Asp
    50                  55                  60

Arg Ser Tyr Pro Val Val Tyr Phe His Asp Gly Gln Asn Val Phe Xaa
65                  70                  75                  80
```

```
Ser Lys Glu Ser Phe Ile Gly Xaa Ser Trp Lys Ile Ile Pro Ala Ile
                85                  90                  95

Lys Arg Asn Pro Asp Ile Ser Xaa Met Ile Val Val Ala Ile Asp Asn
            100                 105                 110

Asp Gly Met Gly Arg Met Asn Glu Tyr Xaa Ala Trp Lys Phe Gln Glu
        115                 120                 125

Ser Pro Ile Pro Xaa Gln Gln Phe Gly Gly Lys Gly Val Glu Tyr Ala
130                 135                 140

Glu Phe Val Met Glu Val Val Lys Pro Phe Ile Asp Glu Thr Tyr Arg
145                 150                 155                 160

Thr Lys Ala Asp Cys Gln His Thr Ala Met Ile Gly Ser Ser Leu Gly
                165                 170                 175

Gly Asn Ile Thr Gln Phe Ile Gly Leu Glu Tyr Gln Xaa Xaa Ile Gly
            180                 185                 190

Cys Leu Gly Val Phe Ser Ser Ala Asn Trp Leu His Gln Glu Ala Phe
        195                 200                 205

Asn Arg Tyr Xaa Glu Cys Gln Lys Leu Ser Pro Asp Gln Xaa Ile Phe
    210                 215                 220

Ile Tyr Val Gly Thr Glu Glu Ala Asp Thr Asp Lys Thr Leu Met
225                 230                 235                 240

Asp Gly Asn Ile Lys Gln Ala Tyr Ile Asp Ser Ser Leu Cys Tyr Tyr
                245                 250                 255

His Asp Leu Ile Ala Gly Xaa Val His Leu Asp Asn Leu Val Leu Lys
            260                 265                 270

Val Gln Ser Gly Ala Ile His Ser Glu Ile Pro Trp Ser Glu Asn Leu
        275                 280                 285

Pro Asp Cys Leu Arg Phe Phe Ala Glu Lys Trp
    290                 295

<210> SEQ ID NO 17
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Met or Thr
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (15)..(15)
<223> OTHER INFORMATION: Ala or Val
<220> FEATURE:
<221> NAME/KEY: MOD_RES
<222> LOCATION: (26)..(26)
<223> OTHER INFORMATION: Met or Ile
<220> FEATURE:
<221> NAME/KEY: MOD_RES
<222> LOCATION: (80)..(80)
<223> OTHER INFORMATION: Asn or Tyr
<220> FEATURE:
<221> NAME/KEY: MOD_RES
<222> LOCATION: (88)..(88)
<223> OTHER INFORMATION: His or Tyr
<220> FEATURE:
<221> NAME/KEY: MOD_RES
<222> LOCATION: (104)..(104)
<223> OTHER INFORMATION: Arg or His
```

<220> FEATURE:
<221> NAME/KEY: MOD_RES
<222> LOCATION: (122)..(122)
<223> OTHER INFORMATION: Ala or Glu
<220> FEATURE:
<221> NAME/KEY: MOD_RES
<222> LOCATION: (133)..(133)
<223> OTHER INFORMATION: Gly or Glu

<400> SEQUENCE: 17

Met Ser Ser Lys Phe Xaa Lys Ser Xaa Ala Val Leu Gly Thr Xaa Thr
1               5                   10                  15

Leu Ala Ser Leu Leu Val Ala Cys Xaa Asn Gln Ser Tyr Phe Tyr
            20                  25                  30

Leu Lys Met Lys Glu His Lys Leu Lys Val Pro Tyr Thr Gly Lys Glu
            35                  40                  45

Arg Arg Val Arg Ile Leu Leu Pro Lys Asp Tyr Glu Lys Asp Thr Asp
            50                  55                  60

Arg Ser Tyr Pro Val Val Tyr Phe His Asp Gly Gln Asn Val Phe Xaa
65                  70                  75                  80

Ser Lys Glu Ser Phe Ile Gly Xaa Ser Trp Lys Ile Ile Pro Ala Ile
                85                  90                  95

Lys Arg Asn Pro Asp Ile Ser Xaa Met Ile Val Ala Ile Asp Asn
            100                 105                 110

Asp Gly Met Gly Arg Met Asn Glu Tyr Xaa Ala Trp Lys Phe Gln Glu
            115                 120                 125

Ser Pro Ile Pro Xaa Gln Gln Phe Gly Gly Lys Gly Val Glu Tyr Ala
            130                 135                 140

Glu Phe Val Met Glu Val Val Lys Pro Phe Ile
145                 150                 155

<210> SEQ ID NO 18
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Gly or Glu
<220> FEATURE:
<221> NAME/KEY: MOD_RES
<222> LOCATION: (24)..(24)
<223> OTHER INFORMATION: Gly or Ser
<220> FEATURE:
<221> NAME/KEY: MOD_RES
<222> LOCATION: (27)..(27)
<223> OTHER INFORMATION: Lys or Arg
<220> FEATURE:
<221> NAME/KEY: MOD_RES
<222> LOCATION: (30)..(30)
<223> OTHER INFORMATION: Ile or Asn
<220> FEATURE:
<221> NAME/KEY: MOD_RES
<222> LOCATION: (56)..(56)
<223> OTHER INFORMATION: Asp or Asn
<220> FEATURE:
<221> NAME/KEY: MOD_RES
<222> LOCATION: (58)..(58)
<223> OTHER INFORMATION: Any amino acid
<220> FEATURE:
<221> NAME/KEY: MOD_RES
<222> LOCATION: (83)..(83)
<223> OTHER INFORMATION: Leu or Ile
<220> FEATURE:
<221> NAME/KEY: MOD_RES

```
<222> LOCATION: (111)..(111)
<223> OTHER INFORMATION: Asp or Glu
<220> FEATURE:
<221> NAME/KEY: MOD_RES
<222> LOCATION: (159)..(159)
<223> OTHER INFORMATION: Leu or Phe
<220> FEATURE:
<221> NAME/KEY: MOD_RES
<222> LOCATION: (192)..(192)
<223> OTHER INFORMATION: Asn or Tyr
<220> FEATURE:
<221> NAME/KEY: MOD_RES
<222> LOCATION: (199)..(199)
<223> OTHER INFORMATION: Pro or Ser

<400> SEQUENCE: 18
```

| Met | Cys | Ser | Gly | Gly | Ala | Lys | Lys | Glu | Gly | Xaa | Ala | Ala | Ser | Lys | Lys |
|---|---|---|---|---|---|---|---|---|---|---|---|---|---|---|---|
| 1 | | | | 5 | | | | | 10 | | | | | 15 | |

Glu Ile Ile Val Ala Thr Asn Xaa Ser Pro Xaa Pro Phe Xaa Tyr Glu
            20                  25                  30

Glu Asn Gly Glu Leu Thr Gly Tyr Glu Ile Glu Val Val Arg Ala Ile
        35                  40                  45

Phe Lys Asp Ser Asp Lys Tyr Xaa Val Xaa Phe Glu Lys Thr Glu Trp
 50                  55                  60

Ser Gly Val Phe Ala Gly Leu Asp Ala Asp Arg Tyr Asn Met Ala Val
 65                  70                  75                  80

Asn Asn Xaa Ser Tyr Thr Lys Glu Arg Ala Gly Lys Tyr Leu Tyr Ala
             85                  90                  95

Ala Pro Ile Ala Gln Asn Pro Asn Val Leu Val Val Lys Lys Xaa Asp
            100                 105                 110

Ser Ser Ile Lys Ser Leu Asp Asp Ile Gly Gly Lys Ser Thr Glu Val
            115                 120                 125

Val Gln Ala Thr Thr Ser Ala Lys Gln Leu Glu Ala Tyr Asn Ala Glu
        130                 135                 140

His Thr Asp Asn Pro Thr Ile Leu Asn Tyr Thr Lys Ala Asp Xaa Gln
145                 150                 155                 160

Gln Ile Met Val Arg Leu Ser Asp Gly Gln Phe Asp Tyr Lys Ile Phe
                165                 170                 175

Asp Lys Ile Gly Val Glu Thr Val Ile Lys Asn Gln Gly Leu Asp Xaa
            180                 185                 190

Leu Lys Val Ile Glu Leu Xaa Ser Asp Gln Gln Pro Tyr Val Tyr Pro
        195                 200                 205

Leu Leu Ala Gln Gly Gln Asp Glu Leu Lys Ser Phe Val Asp Lys Arg
210                 215                 220

Ile Lys Glu Leu Tyr Lys Asp Gly Thr Leu Glu Lys Leu Ser Lys Gln
225                 230                 235                 240

Phe Phe Gly Asp Thr Tyr Leu Pro Ala Glu Ala Asp Ile Lys
                245                 250

```
<210> SEQ ID NO 19
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (14)..(14)
<223> OTHER INFORMATION: Ala or Gly
<220> FEATURE:
<221> NAME/KEY: MOD_RES
```

```
<222> LOCATION: (20)..(20)
<223> OTHER INFORMATION: Val or Leu
<220> FEATURE:
<221> NAME/KEY: MOD_RES
<222> LOCATION: (33)..(33)
<223> OTHER INFORMATION: Glu or Gln
<220> FEATURE:
<221> NAME/KEY: MOD_RES
<222> LOCATION: (46)..(46)
<223> OTHER INFORMATION: Gly or Ser
<220> FEATURE:
<221> NAME/KEY: MOD_RES
<222> LOCATION: (49)..(49)
<223> OTHER INFORMATION: Lys or Arg
<220> FEATURE:
<221> NAME/KEY: MOD_RES
<222> LOCATION: (52)..(52)
<223> OTHER INFORMATION: Ile or Asn
<220> FEATURE:
<221> NAME/KEY: MOD_RES
<222> LOCATION: (78)..(78)
<223> OTHER INFORMATION: Asp or Asn
<220> FEATURE:
<221> NAME/KEY: MOD_RES
<222> LOCATION: (80)..(80)
<223> OTHER INFORMATION: Any amino acid
<220> FEATURE:
<221> NAME/KEY: MOD_RES
<222> LOCATION: (105)..(105)
<223> OTHER INFORMATION: Leu or Ile
<220> FEATURE:
<221> NAME/KEY: MOD_RES
<222> LOCATION: (133)..(133)
<223> OTHER INFORMATION: Asp or Glu
<220> FEATURE:
<221> NAME/KEY: MOD_RES
<222> LOCATION: (181)..(181)
<223> OTHER INFORMATION: Asp or Glu
<220> FEATURE:
<221> NAME/KEY: MOD_RES
<222> LOCATION: (214)..(214)
<223> OTHER INFORMATION: Asn or Tyr
<220> FEATURE:
<221> NAME/KEY: MOD_RES
<222> LOCATION: (221)..(221)
<223> OTHER INFORMATION: Pro or Ser

<400> SEQUENCE: 19

Met Lys Lys Ile Val Lys Tyr Ser Ser Leu Ala Ala Leu Xaa Leu Val
 1               5                  10                  15

Ala Ala Gly Xaa Leu Ala Ala Cys Ser Gly Gly Ala Lys Lys Glu Gly
            20                  25                  30

Xaa Ala Ala Ser Lys Lys Glu Ile Ile Val Ala Thr Asn Xaa Ser Pro
        35                  40                  45

Xaa Pro Phe Xaa Tyr Glu Glu Asn Gly Glu Leu Thr Gly Tyr Glu Ile
    50                  55                  60

Glu Val Val Arg Ala Ile Phe Lys Asp Ser Asp Lys Tyr Xaa Val Xaa
65                  70                  75                  80

Phe Glu Lys Thr Glu Trp Ser Gly Val Phe Ala Gly Leu Asp Ala Asp
                85                  90                  95

Arg Tyr Asn Met Ala Val Asn Asn Xaa Ser Tyr Thr Lys Glu Arg Ala
                100                 105                 110

Glu Lys Tyr Leu Tyr Ala Ala Pro Ile Ala Gln Asn Pro Asn Val Leu
            115                 120                 125

Val Val Lys Lys Xaa Asp Ser Ser Ile Lys Ser Leu Asp Asp Ile Gly
        130                 135                 140

Gly Lys Ser Thr Glu Val Val Gln Ala Thr Thr Ser Ala Lys Gln Leu
145                 150                 155                 160
```

-continued

```
Glu Ala Tyr Asn Ala Glu His Thr Asp Asn Pro Thr Ile Leu Asn Tyr
                165                 170                 175

Thr Lys Ala Asp Xaa Gln Gln Ile Met Val Arg Leu Ser Asp Gly Gln
        180                 185                 190

Phe Asp Tyr Lys Ile Phe Asp Lys Ile Gly Val Glu Thr Val Ile Lys
            195                 200                 205

Asn Gln Gly Leu Asp Xaa Leu Lys Val Ile Glu Leu Xaa Ser Asp Gln
210                 215                 220

Gln Pro Tyr Val Tyr Pro Leu Leu Ala Gln Gly Gln Asp Glu Leu Lys
225                 230                 235                 240

Ser Phe Val Asp Lys Arg Ile Lys Glu Leu Tyr Lys Asp Gly Thr Leu
                245                 250                 255

Glu Lys Leu Ser Lys Gln Phe Phe Gly Asp Thr Tyr Leu Pro Ala Glu
            260                 265                 270

Ala Asp Ile Lys
        275

<210> SEQ ID NO 20
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Val or Ala
<220> FEATURE:
<221> NAME/KEY: MOD_RES
<222> LOCATION: (48)..(48)
<223> OTHER INFORMATION: Val or Ile
<220> FEATURE:
<221> NAME/KEY: MOD_RES
<222> LOCATION: (74)..(74)
<223> OTHER INFORMATION: Val or Ile
<220> FEATURE:
<221> NAME/KEY: MOD_RES
<222> LOCATION: (83)..(83)
<223> OTHER INFORMATION: Any amino acid
<220> FEATURE:
<221> NAME/KEY: MOD_RES
<222> LOCATION: (100)..(100)
<223> OTHER INFORMATION: Ala or Thr
<220> FEATURE:
<221> NAME/KEY: MOD_RES
<222> LOCATION: (177)..(177)
<223> OTHER INFORMATION: Thr or Ala
<220> FEATURE:
<221> NAME/KEY: MOD_RES
<222> LOCATION: (186)..(186)
<223> OTHER INFORMATION: Ala or Gly
<220> FEATURE:
<221> NAME/KEY: MOD_RES
<222> LOCATION: (196)..(196)
<223> OTHER INFORMATION: Ala or Pro
<220> FEATURE:
<221> NAME/KEY: MOD_RES
<222> LOCATION: (208)..(208)
<223> OTHER INFORMATION: Val or Ala
<220> FEATURE:
<221> NAME/KEY: MOD_RES
<222> LOCATION: (214)..(214)
<223> OTHER INFORMATION: Any amino acid
<220> FEATURE:
<221> NAME/KEY: MOD_RES
<222> LOCATION: (237)..(237)
<223> OTHER INFORMATION: Gln or His
<220> FEATURE:
<221> NAME/KEY: MOD_RES
<222> LOCATION: (298)..(298)
```

<223> OTHER INFORMATION: Ser or Ala
<220> FEATURE:
<221> NAME/KEY: MOD_RES
<222> LOCATION: (307)..(307)
<223> OTHER INFORMATION: Ala or Ser
<220> FEATURE:
<221> NAME/KEY: MOD_RES
<222> LOCATION: (313)..(313)
<223> OTHER INFORMATION: Val or Ala
<220> FEATURE:
<221> NAME/KEY: MOD_RES
<222> LOCATION: (348)..(348)
<223> OTHER INFORMATION: Asn or Ser

<400> SEQUENCE: 20

```
Met Cys Gly Ser Lys Thr Ala Asp Lys Pro Ala Asp Ser Gly Ser Ser
1               5                   10                  15

Glu Xaa Lys Glu Leu Thr Val Tyr Val Asp Glu Gly Tyr Lys Ser Tyr
                20                  25                  30

Ile Glu Glu Val Ala Lys Ala Tyr Glu Lys Glu Ala Gly Val Lys Xaa
            35                  40                  45

Thr Leu Lys Thr Gly Asp Ala Leu Gly Gly Leu Asp Lys Leu Ser Leu
    50                  55                  60

Asp Asn Gln Ser Gly Asn Val Pro Asp Xaa Met Met Ala Pro Tyr Asp
65                  70                  75                  80

Arg Val Xaa Ser Leu Gly Ser Asp Gly Gln Leu Ser Glu Val Lys Leu
                85                  90                  95

Ser Asp Gly Xaa Lys Thr Asp Asp Thr Thr Lys Ser Leu Val Thr Ala
                100                 105                 110

Ala Asn Gly Lys Val Tyr Gly Ala Pro Ala Val Ile Glu Ser Leu Val
            115                 120                 125

Met Tyr Tyr Asn Lys Asp Leu Val Lys Asp Ala Pro Lys Thr Phe Ala
    130                 135                 140

Asp Leu Glu Asn Leu Ala Lys Asp Ser Lys Tyr Ala Phe Ala Gly Glu
145                 150                 155                 160

Asp Gly Lys Thr Thr Ala Phe Leu Ala Asp Trp Thr Asn Phe Tyr Tyr
                165                 170                 175

Xaa Tyr Gly Leu Leu Ala Gly Asn Gly Xaa Tyr Val Phe Gly Gln Asn
            180                 185                 190

Gly Lys Asp Xaa Lys Asp Ile Gly Leu Ala Asn Asp Gly Ser Ile Xaa
    195                 200                 205

Gly Ile Asn Tyr Ala Xaa Ser Trp Tyr Glu Lys Trp Pro Lys Gly Met
    210                 215                 220

Gln Asp Thr Glu Gly Ala Gly Asn Leu Ile Gln Thr Xaa Phe Gln Glu
225                 230                 235                 240

Gly Lys Thr Ala Ala Ile Ile Asp Gly Pro Trp Lys Ala Gln Ala Phe
                245                 250                 255

Lys Asp Ala Lys Val Asn Tyr Gly Val Ala Thr Ile Pro Thr Leu Pro
            260                 265                 270

Asn Gly Lys Glu Tyr Ala Ala Phe Gly Gly Lys Ala Trp Val Ile
    275                 280                 285

Pro Gln Ala Val Lys Asn Leu Glu Ala Xaa Gln Lys Phe Val Asp Phe
    290                 295                 300

Leu Val Xaa Thr Glu Gln Gln Lys Xaa Leu Tyr Asp Lys Thr Asn Glu
305                 310                 315                 320

Ile Pro Ala Asn Thr Glu Ala Arg Ser Tyr Ala Glu Gly Lys Asn Asp
                325                 330                 335
```

Glu Leu Thr Thr Ala Val Ile Lys Gln Phe Lys Xaa Thr Gln Pro Leu
            340                 345                 350

Pro Asn Ile Ser Gln Met Ser Ala Val Trp Asp Pro Ala Lys Asn Met
        355                 360                 365

Leu Phe Asp Ala Val Ser Gly Gln Lys Asp Ala Lys Thr Ala Ala Asn
    370                 375                 380

Asp Ala Val Thr Leu Ile Lys Glu Thr Ile Lys Gln Lys Phe Gly Glu
385                 390                 395                 400

```
<210> SEQ ID NO 21
<211> LENGTH: 423
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Met or Thr
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (15)..(15)
<223> OTHER INFORMATION: Ala or Val
<220> FEATURE:
<221> NAME/KEY: MOD_RES
<222> LOCATION: (41)..(41)
<223> OTHER INFORMATION: Val or Ala
<220> FEATURE:
<221> NAME/KEY: MOD_RES
<222> LOCATION: (71)..(71)
<223> OTHER INFORMATION: Val or Ile
<220> FEATURE:
<221> NAME/KEY: MOD_RES
<222> LOCATION: (97)..(97)
<223> OTHER INFORMATION: Val or Ile
<220> FEATURE:
<221> NAME/KEY: MOD_RES
<222> LOCATION: (106)..(106)
<223> OTHER INFORMATION: Any amino acid
<220> FEATURE:
<221> NAME/KEY: MOD_RES
<222> LOCATION: (123)..(123)
<223> OTHER INFORMATION: Ala or Thr
<220> FEATURE:
<221> NAME/KEY: MOD_RES
<222> LOCATION: (200)..(200)
<223> OTHER INFORMATION: Thr or Ala
<220> FEATURE:
<221> NAME/KEY: MOD_RES
<222> LOCATION: (209)..(209)
<223> OTHER INFORMATION: Ala or Gly
<220> FEATURE:
<221> NAME/KEY: MOD_RES
<222> LOCATION: (219)..(219)
<223> OTHER INFORMATION: Ala or Pro
<220> FEATURE:
<221> NAME/KEY: MOD_RES
<222> LOCATION: (231)..(231)
<223> OTHER INFORMATION: Val or Ala
<220> FEATURE:
<221> NAME/KEY: MOD_RES
<222> LOCATION: (237)..(237)
<223> OTHER INFORMATION: Any amino acid
<220> FEATURE:
<221> NAME/KEY: MOD_RES
<222> LOCATION: (260)..(260)
<223> OTHER INFORMATION: Gln or His
<220> FEATURE:
<221> NAME/KEY: MOD_RES
<222> LOCATION: (321)..(321)
```

```
<223> OTHER INFORMATION: Ser or Ala
<220> FEATURE:
<221> NAME/KEY: MOD_RES
<222> LOCATION: (330)..(330)
<223> OTHER INFORMATION: Ala or Ser
<220> FEATURE:
<221> NAME/KEY: MOD_RES
<222> LOCATION: (336)..(336)
<223> OTHER INFORMATION: Val or Ala
<220> FEATURE:
<221> NAME/KEY: MOD_RES
<222> LOCATION: (371)..(371)
<223> OTHER INFORMATION: Asn or Ser

<400> SEQUENCE: 21

Met Ser Ser Lys Phe Xaa Lys Ser Xaa Ala Val Leu Gly Thr Xaa Thr
1               5                   10                  15

Leu Ala Ser Leu Leu Val Ala Cys Gly Ser Lys Thr Ala Asp Lys
            20                  25                  30

Pro Ala Asp Ser Gly Ser Ser Glu Xaa Lys Glu Leu Thr Val Tyr Val
            35                  40                  45

Asp Glu Gly Tyr Lys Ser Tyr Ile Glu Val Ala Lys Ala Tyr Glu
        50                  55                  60

Lys Glu Ala Gly Val Lys Xaa Thr Leu Lys Thr Gly Asp Ala Leu Gly
65                  70                  75                  80

Gly Leu Asp Lys Leu Ser Leu Asp Asn Gln Ser Gly Asn Val Pro Asp
                85                  90                  95

Xaa Met Met Ala Pro Tyr Asp Arg Val Xaa Ser Leu Gly Ser Asp Gly
            100                 105                 110

Gln Leu Ser Glu Val Lys Leu Ser Asp Gly Xaa Lys Thr Asp Asp Thr
        115                 120                 125

Thr Lys Ser Leu Val Thr Ala Ala Asn Gly Lys Val Tyr Gly Ala Pro
130                 135                 140

Ala Val Ile Glu Ser Leu Val Met Tyr Tyr Asn Lys Asp Leu Val Lys
145                 150                 155                 160

Asp Ala Pro Lys Thr Phe Ala Asp Leu Glu Asn Leu Ala Lys Asp Ser
                165                 170                 175

Lys Tyr Ala Phe Ala Gly Glu Asp Gly Lys Thr Thr Ala Phe Leu Ala
            180                 185                 190

Asp Trp Thr Asn Phe Tyr Tyr Xaa Tyr Gly Leu Leu Ala Gly Asn Gly
        195                 200                 205

Xaa Tyr Val Phe Gly Gln Asn Gly Lys Asp Xaa Lys Asp Ile Gly Leu
210                 215                 220

Ala Asn Asp Gly Ser Ile Xaa Gly Ile Asn Tyr Ala Xaa Ser Trp Tyr
225                 230                 235                 240

Glu Lys Trp Pro Lys Gly Met Gln Asp Thr Glu Gly Ala Gly Asn Leu
                245                 250                 255

Ile Gln Thr Xaa Phe Gln Glu Gly Lys Thr Ala Ala Ile Ile Asp Gly
            260                 265                 270

Pro Trp Lys Ala Gln Ala Phe Lys Asp Ala Lys Val Asn Tyr Gly Val
        275                 280                 285

Ala Thr Ile Pro Thr Leu Pro Asn Gly Lys Glu Tyr Ala Ala Phe Gly
290                 295                 300

Gly Gly Lys Ala Trp Val Ile Pro Gln Ala Val Lys Asn Leu Glu Ala
305                 310                 315                 320

Xaa Gln Lys Phe Val Asp Phe Leu Val Xaa Thr Glu Gln Gln Lys Xaa
                325                 330                 335
```

Leu Tyr Asp Lys Thr Asn Glu Ile Pro Ala Asn Thr Glu Ala Arg Ser
            340                 345                 350

Tyr Ala Glu Gly Lys Asn Asp Glu Leu Thr Thr Ala Val Ile Lys Gln
        355                 360                 365

Phe Lys Xaa Thr Gln Pro Leu Pro Asn Ile Ser Gln Met Ser Ala Val
    370                 375                 380

Trp Asp Pro Ala Lys Asn Met Leu Phe Asp Ala Val Ser Gly Gln Lys
385                 390                 395                 400

Asp Ala Lys Thr Ala Ala Asn Asp Ala Val Thr Leu Ile Lys Glu Thr
                405                 410                 415

Ile Lys Gln Lys Phe Gly Glu
            420

<210> SEQ ID NO 22
<211> LENGTH: 357
<212> TYPE: PRT
<213> ORGANISM: Streptococcus pneumoniae

<400> SEQUENCE: 22

Met Ala Asn Ile Phe Asp Tyr Leu Lys Asp Val Ala Tyr Asp Ser Tyr
1               5                   10                  15

Tyr Asp Leu Pro Leu Asn Glu Leu Asp Ile Leu Thr Leu Ile Glu Ile
            20                  25                  30

Thr Tyr Leu Ser Phe Asp Asn Leu Val Ser Thr Leu Pro Gln Arg Leu
        35                  40                  45

Leu Asp Leu Ala Pro Gln Val Pro Arg Asp Pro Thr Met Leu Thr Ser
    50                  55                  60

Lys Asn Arg Leu Gln Leu Leu Asp Glu Leu Ala Gln His Lys Arg Phe
65                  70                  75                  80

Lys Asn Cys Lys Leu Ser His Phe Ile Asn Asp Ile Asp Pro Glu Leu
            85                  90                  95

Gln Lys Gln Phe Ala Ala Met Thr Tyr Arg Val Ser Leu Asp Thr Tyr
            100                 105                 110

Leu Ile Val Phe Arg Gly Thr Asp Asp Ser Ile Ile Gly Trp Lys Glu
        115                 120                 125

Asp Phe His Leu Thr Tyr Met Lys Glu Ile Pro Ala Gln Lys His Ala
    130                 135                 140

Leu Arg Tyr Leu Lys Asn Phe Phe Ala His His Pro Lys Gln Lys Val
145                 150                 155                 160

Ile Leu Ala Gly His Ser Lys Gly Gly Asn Leu Ala Ile Tyr Ala Ala
            165                 170                 175

Ser Gln Ile Glu Gln Ser Leu Gln Asn Gln Ile Thr Ala Val Tyr Thr
            180                 185                 190

Phe Asp Ala Pro Gly Leu His Gln Glu Leu Thr Gln Thr Ala Gly Tyr
        195                 200                 205

Gln Arg Ile Met Asp Arg Ser Lys Ile Phe Ile Pro Gln Gly Ser Ile
    210                 215                 220

Ile Gly Met Met Leu Glu Ile Pro Ala His Gln Ile Ile Val Gln Ser
225                 230                 235                 240

Thr Ala Leu Gly Gly Ile Ala Gln His Asp Thr Phe Ser Trp Gln Ile
            245                 250                 255

Glu Asp Lys His Phe Val Gln Leu Asp Lys Thr Asn Ser Asp Ser Gln
            260                 265                 270

Gln Val Asp Thr Thr Phe Lys Glu Trp Val Ala Thr Val Pro Asp Glu
        275                 280                 285

Glu Leu Gln Leu Tyr Phe Asp Leu Phe Phe Gly Thr Ile Leu Asp Ala
            290                 295                 300

Gly Ile Ser Ser Ile Asn Asp Leu Ala Ser Leu Lys Ala Leu Glu Tyr
305                 310                 315                 320

Ile His His Leu Phe Val Gln Ala Gln Ser Leu Thr Pro Glu Glu Arg
                325                 330                 335

Glu Thr Leu Gly Arg Leu Thr Gln Leu Leu Ile Asp Thr Arg Tyr Gln
            340                 345                 350

Ala Trp Lys Asn Arg
            355

<210> SEQ ID NO 23
<211> LENGTH: 1066
<212> TYPE: PRT
<213> ORGANISM: Streptococcus pneumoniae

<400> SEQUENCE: 23

Met Gln Thr Lys Thr Lys Lys Leu Ile Val Ser Leu Ser Ser Leu Val
1               5                   10                  15

Leu Ser Gly Phe Leu Leu Asn His Tyr Met Thr Ile Gly Ala Glu Glu
            20                  25                  30

Thr Thr Thr Asn Thr Ile Gln Gln Ser Gln Lys Glu Val Gln Tyr Gln
        35                  40                  45

Gln Arg Asp Thr Lys Asn Leu Val Glu Asn Gly Asp Phe Gly Gln Thr
    50                  55                  60

Glu Asp Gly Ser Ser Pro Trp Thr Gly Ser Lys Ala Gln Gly Trp Ser
65                  70                  75                  80

Ala Trp Val Asp Gln Lys Asn Ser Ala Asp Ala Ser Thr Arg Val Ile
                85                  90                  95

Glu Ala Lys Asp Gly Ala Ile Thr Ile Ser Ser His Glu Lys Leu Arg
            100                 105                 110

Ala Ala Leu His Arg Met Val Pro Ile Glu Ala Lys Lys Lys Tyr Lys
        115                 120                 125

Leu Arg Phe Lys Ile Lys Thr Asp Asn Lys Ile Gly Ile Ala Lys Val
    130                 135                 140

Arg Ile Ile Glu Glu Ser Gly Lys Asp Lys Arg Leu Trp Asn Ser Ala
145                 150                 155                 160

Thr Thr Ser Gly Thr Lys Asp Trp Gln Thr Ile Glu Ala Asp Tyr Ser
                165                 170                 175

Pro Thr Leu Asp Val Asp Lys Ile Lys Leu Glu Leu Phe Tyr Glu Thr
            180                 185                 190

Gly Thr Gly Thr Val Ser Phe Lys Asp Ile Glu Leu Val Glu Val Ala
        195                 200                 205

Asp Gln Leu Ser Glu Asp Ser Gln Thr Asp Lys Gln Leu Glu Glu Lys
    210                 215                 220

Ile Asp Leu Pro Ile Gly Lys Lys His Val Phe Ser Leu Ala Asp Tyr
225                 230                 235                 240

Thr Tyr Lys Val Glu Asn Pro Asp Val Ala Ser Val Lys Asn Gly Ile
                245                 250                 255

Leu Glu Pro Leu Lys Glu Gly Thr Thr Asn Val Ile Val Ser Lys Asp
            260                 265                 270

Gly Lys Glu Val Lys Lys Ile Pro Leu Lys Ile Leu Ala Ser Val Lys
        275                 280                 285

Asp Ala Tyr Thr Asp Arg Leu Asp Asp Trp Asn Gly Ile Ile Ala Gly

```
                290                 295                 300
Asn Gln Tyr Tyr Asp Ser Lys Asn Glu Gln Met Ala Lys Leu Asn Gln
305                 310                 315                 320

Glu Leu Glu Gly Lys Val Ala Asp Ser Leu Ser Ile Ser Ser Gln
                325                 330                 335

Ala Asp Arg Thr Tyr Leu Trp Glu Lys Phe Ser Asn Tyr Lys Thr Ser
                340                 345                 350

Ala Asn Leu Thr Ala Thr Tyr Arg Lys Leu Glu Glu Met Ala Lys Gln
            355                 360                 365

Val Thr Asn Pro Ser Ser Arg Tyr Tyr Gln Asp Glu Thr Val Val Arg
370                 375                 380

Thr Val Arg Asp Ser Met Glu Trp Met His Lys His Val Tyr Asn Ser
385                 390                 395                 400

Glu Lys Ser Ile Val Gly Asn Trp Trp Asp Tyr Glu Ile Gly Thr Pro
                405                 410                 415

Arg Ala Ile Asn Asn Thr Leu Ser Leu Met Lys Glu Tyr Phe Ser Asp
                420                 425                 430

Glu Glu Ile Lys Lys Tyr Thr Asp Val Ile Glu Lys Phe Val Pro Asp
            435                 440                 445

Pro Glu His Phe Arg Lys Thr Thr Asp Asn Pro Phe Lys Ala Leu Gly
        450                 455                 460

Gly Asn Leu Val Asp Met Gly Arg Val Lys Val Ile Ala Gly Leu Leu
465                 470                 475                 480

Arg Lys Asp Asp Gln Glu Ile Ser Ser Thr Ile Arg Ser Ile Glu Gln
                485                 490                 495

Val Phe Lys Leu Val Asp Gln Gly Glu Gly Phe Tyr Gln Asp Gly Ser
                500                 505                 510

Tyr Ile Asp His Thr Asn Val Ala Tyr Thr Gly Ala Tyr Gly Asn Val
            515                 520                 525

Leu Ile Asp Gly Leu Ser Gln Leu Leu Pro Val Ile Gln Lys Thr Lys
        530                 535                 540

Asn Pro Ile Asp Lys Asp Lys Met Gln Thr Met Tyr His Trp Ile Asp
545                 550                 555                 560

Lys Ser Phe Ala Pro Leu Leu Val Asn Gly Glu Leu Met Asp Met Ser
                565                 570                 575

Arg Gly Arg Ser Ile Ser Arg Ala Asn Ser Glu Gly His Val Ala Ala
                580                 585                 590

Val Glu Val Leu Arg Gly Ile His Arg Ile Ala Asp Met Ser Glu Gly
            595                 600                 605

Glu Thr Lys Gln Cys Leu Gln Ser Leu Val Lys Thr Ile Val Gln Ser
610                 615                 620

Asp Ser Tyr Tyr Asp Val Phe Lys Asn Leu Lys Thr Tyr Lys Asp Ile
625                 630                 635                 640

Ser Leu Met Gln Ser Leu Leu Ser Asp Ala Gly Val Ala Ser Val Pro
                645                 650                 655

Arg Pro Ser Tyr Leu Ser Ala Phe Asn Lys Met Asp Lys Thr Ala Met
                660                 665                 670

Tyr Asn Ala Glu Lys Gly Phe Gly Phe Gly Leu Ser Leu Phe Ser Ser
            675                 680                 685

Arg Thr Leu Asn Tyr Glu His Met Asn Lys Glu Asn Lys Arg Gly Trp
        690                 695                 700

Tyr Thr Ser Asp Gly Met Phe Tyr Leu Tyr Asn Gly Asp Leu Ser His
705                 710                 715                 720
```

Tyr Ser Asp Gly Tyr Trp Pro Thr Val Asn Pro Tyr Lys Met Pro Gly
            725                 730                 735

Thr Thr Glu Thr Asp Ala Lys Arg Ala Asp Ser Asp Thr Gly Lys Val
        740                 745                 750

Leu Pro Ser Ala Phe Val Gly Thr Ser Lys Leu Asp Asp Ala Asn Ala
    755                 760                 765

Thr Ala Thr Met Asp Phe Thr Asn Trp Asn Gln Thr Leu Thr Ala His
770                 775                 780

Lys Ser Trp Phe Met Leu Lys Asp Lys Ile Ala Phe Leu Gly Ser Asn
785                 790                 795                 800

Ile Gln Asn Thr Ser Thr Asp Thr Ala Ala Thr Thr Ile Asp Gln Arg
                805                 810                 815

Lys Leu Glu Ser Gly Asn Pro Tyr Lys Val Tyr Val Asn Asp Lys Glu
            820                 825                 830

Ala Ser Leu Thr Glu Gln Glu Lys Asp Tyr Pro Glu Thr Gln Ser Val
        835                 840                 845

Phe Leu Glu Ser Phe Asp Ser Lys Asn Ile Gly Tyr Phe Phe
    850                 855                 860

Lys Lys Ser Ser Ile Ser Met Ser Lys Ala Leu Gln Lys Gly Ala Trp
865                 870                 875                 880

Lys Asp Ile Asn Glu Gly Gln Ser Asp Lys Glu Val Glu Asn Glu Phe
                885                 890                 895

Leu Thr Ile Ser Gln Ala His Lys Gln Asn Arg Asp Ser Tyr Gly Tyr
            900                 905                 910

Met Leu Ile Pro Asn Val Asp Arg Ala Thr Phe Asn Gln Met Ile Lys
        915                 920                 925

Glu Leu Glu Ser Ser Leu Ile Glu Asn Asn Glu Thr Leu Gln Ser Val
    930                 935                 940

Tyr Asp Ala Lys Gln Gly Val Trp Gly Ile Val Lys Tyr Asp Asp Ser
945                 950                 955                 960

Val Ser Thr Ile Ser Asn Gln Phe Gln Val Leu Lys Arg Gly Val Tyr
                965                 970                 975

Thr Ile Arg Lys Glu Gly Asp Glu Tyr Lys Ile Ala Tyr Tyr Asn Pro
            980                 985                 990

Glu Thr Gln Glu Ser Ala Pro Asp Gln Glu Val Phe Lys Lys Leu Glu
        995                 1000                1005

Gln Ala Ala Gln Pro Gln Val Gln Asn Ser Lys Glu Lys Glu Lys
    1010                1015                1020

Ser Glu Glu Lys Asn His Ser Asp Gln Lys Asn Leu Pro Gln
    1025                1030                1035

Thr Gly Glu Gly Gln Ser Ile Leu Ala Ser Leu Gly Phe Leu Leu
    1040                1045                1050

Leu Gly Ala Phe Tyr Leu Phe Arg Arg Gly Lys Asn Asn
    1055                1060                1065

<210> SEQ ID NO 24
<211> LENGTH: 390
<212> TYPE: DNA
<213> ORGANISM: Streptococcus pneumoniae

<400> SEQUENCE: 24
atgaatcaat cctactttta tctaaaaatg aaagaacaca aactcaaggt tccttataca      60
ggtaaggagc gccgtgtacg tattcttctt cctaaagatt atgagaaaga tacagaccgt     120

```
tcctatcctg ttgtatactt tcatgacggg caaaatgttt ttaatagcaa agagtctttc      180
attggacatt catggaagat tatcccagct atcaaacgaa atccggatat cagtcgcatg      240
attgtcgttg ctattgacaa tgatggtatg gggcggatga atgagtatgc ggcttggaag      300
ttccaagaat ctcctatccc agggcagcag tttggtggta agggtgtgga gtatgctgag      360
tttgtcatgg aggtggtcaa gccttttatc                                       390
```

<210> SEQ ID NO 25
<211> LENGTH: 900
<212> TYPE: DNA
<213> ORGANISM: Streptococcus pneumoniae

<400> SEQUENCE: 25

```
atgtcatcta aatttatgaa gagcgctgcg gtgcttggaa ctgctacact tgctagcttg       60
cttttggtag cttgcatgaa tcaatcctac ttttatctaa aaatgaaaga acacaaactc      120
aaggttcctt atacaggtaa ggagcgccgt gtacgtattc ttcttcctaa agattatgag      180
aaagatacag accgttccta tcctgttgta tactttcatg acgggcaaaa tgtttttaat      240
agcaaagagt ctttcattgg acattcatgg aagattatcc cagctatcaa acgaaatccg      300
gatatcagtc gcatgattgt cgttgctatt gacaatgatg gtatggggcg gatgaatgag      360
tatgcggctt ggaagttcca gaatctcct atcccagggc agcagtttgg tggtaagggt      420
gtggagtatg ctgagtttgt catggaggtg gtcaagcctt ttatcgatga gcctatcgt      480 acaaaagcag actgccagca tacggctatg attggttcct cactaggagg caatattacc      540
cagtttatcg gtttggaata ccaagaccaa attggttgct gggcgttttt ttcatctgca      600
aactggctcc accaagaagc ctttaaccgc tatttcgagt gccagaaact atcgcctgac      660
cagcgcatct tcatctatgt aggaacgaaa gaagcagatg atacagacaa gaccttgatg      720
gatggcaata tcaaacaagc ctatatcgac tcgtcgcttt gctattacca tgatttgata      780 gcaggggag tacatctgga taatcttgtg ctaaaagttc agtctggtgc catccatagt      840
gaaatccctt ggtcagaaaa tctaccagat tgtctgagat tttttgcaga aaaatggtaa      900
```

<210> SEQ ID NO 26
<211> LENGTH: 465
<212> TYPE: DNA
<213> ORGANISM: Streptococcus pneumoniae

<400> SEQUENCE: 26

```
atgtcatcta aatttatgaa gagcgctgcg gtgcttggaa ctgctacact tgctagcttg       60
cttttggtag cttgcatgaa tcaatcctac ttttatctaa aaatgaaaga acacaaactc      120
aaggttcctt atacaggtaa ggagcgccgt gtacgtattc ttcttcctaa agattatgag      180
aaagatacag accgttccta tcctgttgta tactttcatg acgggcaaaa tgtttttaat      240
agcaaagagt ctttcattgg acattcatgg aagattatcc cagctatcaa acgaaatccg      300
gatatcagtc gcatgattgt cgttgctatt gacaatgatg gtatggggcg gatgaatgag      360
tatgcggctt ggaagttcca gaatctcct atcccagggc agcagtttgg tggtaagggt      420
gtggagtatg ctgagtttgt catggaggtg gtcaagcctt ttatc                      465
```

<210> SEQ ID NO 27
<211> LENGTH: 765
<212> TYPE: DNA
<213> ORGANISM: Streptococcus pneumoniae

<400> SEQUENCE: 27

```
atgtgctcag ggggtgctaa gaaagaagga gaagcagcta gcaagaaaga aatcatcgtt      60
gcaaccaatg gatcaccaaa gccatttatc tatgaagaaa atggcgaatt gactggttac     120
gagattgaag tcgttcgcgc tatctttaaa gattctgaca atatgatgt  caagtttgaa     180 aagacagaat ggtcaggtgt ctttgctggt cttgacgctg atcgttacaa tatggctgtc     240
aacaatctta gctacactaa agaacgtgcg gagaaatacc tctatgccgc accaattgcc     300
caaaatccta atgtccttgt cgtgaagaaa gatgactcta gtatcaagtc tctcgatgat     360
atcggtggaa atcgacgga  agtcgttcaa gccactacat cagctaagca gttagaagca     420
tacaatgctg aacacacgga caacccaact atccttaact atactaaggc agacttccaa     480
caaatcatgg tacgtttgag cgatggacaa tttgactata gattttttga taaaatcggt     540
gttgaaacag tgatcaagaa ccaaggtttg acaacttga  agttatcga  acttccaagc     600 gaccaacaac cgtacgttta cccacttctt gctcagggtc aagatgagtt gaaatcgttt     660
gtagacaaac gcatcaaaga actttataaa gatggaactc ttgaaaaatt gtctaaacaa     720
ttcttcggag acacttatct accggcagaa gctgatatta ataa                      765
```

`<210> SEQ ID NO 28`
`<211> LENGTH: 831`
`<212> TYPE: DNA`
`<213> ORGANISM: Streptococcus pneumoniae`

`<400> SEQUENCE: 28`

```
atgaaaaaaa tcgttaaata ctcatctctt gcagcccttg ctcttgttgc tgcaggtgtg      60
cttgcggctt gctcagggg  tgctaagaaa gaaggagaag cagctagcaa gaaagaaatc     120
atcgttgcaa ccaatggatc accaaagcca tttatctatg aagaaatgg  cgaattgact     180 ggttacgaga ttgaagtcgt tcgcgctatc tttaaagatt ctgacaaata tgatgtcaag     240
tttgaaaaga cagaatggtc aggtgtcttt gctggtcttg acgctgatcg ttacaatatg     300
gctgtcaaca atcttagcta cactaaagaa cgtgcggaga aataccctcta tgccgcacca     360 attgcccaaa atcctaatgt ccttgtcgtg aagaaagatg actctagtat caagtctctc     420
gatgatatcg gtggaaaatc gacggaagtc gttcaagcca ctcatcagc  taagcagtta     480 gaagcataca atgctgaaca cacggacaac ccaactatcc ttaactatac taaggcagac     540
ttccaacaaa tcatggtacg tttgagcgat ggacaatttg actataagat ttttgataaa     600
atcggtgttg aaacagtgat caagaaccaa ggtttggaca acttgaaagt tatcgaactt     660
ccaagcgacc aacaaccgta cgtttaccca cttcttgctc agggtcaaga tgagttgaaa     720
tcgtttgtag acaaacgcat caagaaactt tataagatg  gaactcttga aaaattgtct     780
aaacaattct tcggagacac ttatctaccg gcagaagctg atattaaata a              831
```

`<210> SEQ ID NO 29`
`<211> LENGTH: 1203`
`<212> TYPE: DNA`
`<213> ORGANISM: Streptococcus pneumoniae`

`<400> SEQUENCE: 29`

```
atgtgcggaa gcaaaactgc tgataagcct gctgattctg gttcatctga agtcaaagaa      60
ctcactgtat atgtagacga gggatataag agctatattg aagaggttgc taaagcttat     120
gaaaaagaag ctggagtaaa agtcactctt aaaactggtg atgctctagg aggtcttgat     180
aaactttctc ttgacaacca atctggtaat gtccctgatg ttatgatggc tccatacgac     240
```

```
cgtgtaggta gccttggttc tgacggacaa ctttcagaag tgaaattgag cgatggtgct      300
aaaacagacg acacaactaa atctcttgta acagctgcta atggtaaagt ttacggtgct      360
cctgccgtta tcgagtcact tgttatgtac tacaacaaag acttggtgaa agatgctcca      420
aaaacatttg ctgacttgga aaaccttgct aaagatagca atacgcatt cgctggtgaa       480 gatggtaaaa ctactgcctt cctagctgac tggacaaact tctactatac atatggactt     540
cttgccggta acggtgctta cgtctttggc caaaacggta agacgctaa agacatcggt       600 cttgcaaacg acggttctat cgtaggtatc aactacgcta atcttggta cgaaaaatgg       660 cctaaaggta tgcaagatac agaaggtgct ggaaacttaa tccaaactca attccaagaa     720
ggtaaaacag ctgctatcat cgacggacct tggaaagctc aagccttta agatgctaaa      780 gtaaactacg gagttgcaac tatcccaact cttccaaatg aaaagaata tgctgcattc       840 ggtggtggta agcttgggt cattcctcaa gccgttaaga accttgaagc ttctcaaaaa      900
tttgtagact tccttgttgc aactgaacaa caaaaagtat tatatgataa gactaacgaa     960
atcccagcta atactgaggc tcgttcatac gctgaaggta aaaacgatga gttgacaaca     1020
gctgttatca aacagttcaa gaacactcaa ccactgccaa acatctctca aatgtctgca     1080
gtttgggatc cagcgaaaaa tatgctcttt gatgctgtaa gtggtcaaaa agatgctaaa     1140
acagctgcta acgatgctgt aacattgatc aaagaaacaa tcaaacaaaa atttggtgaa     1200
taa                                                                   1203

<210> SEQ ID NO 30
<211> LENGTH: 1944
<212> TYPE: DNA
<213> ORGANISM: Streptococcus pneumoniae

<400> SEQUENCE: 30
atgtcaggaa ctagtatggc gactccaatc gtggcagctt ctactgtttt gattagaccg     60
aaattaaagg aaatgcttga agacctgta ttgaaaaatc ttaagggaga tgacaaaata      120
gatcttacaa gtcttacaaa aattgcccta caaaatactg cgcgacctat gatggatgca     180
acttcttgga aagaaaaaag tcaatacttt gcatcaccta acaacaggg agcaggccta      240 attaatgtgg ccaatgcttt gagaaatgaa gttgtagcaa ctttcaaaaa cactgattct    300 aaaggttttgg taaactcata tggttccatt tctcttaaag aaataaaagg tgataaaaaa    360
tactttacaa tcaagcttca caatacatca aacagacctt tgacttttaa agtttcagca    420
tcagcgataa ctacagattc tctaactgac agattaaaac ttgatgaaac atataaagat    480
gaaaaatctc cagatggtaa gcaaattgtt ccagaaattc acccagaaaa agtcaaagga    540
gcaaatatca catttgagca tgatactttc actataggcg caaattctag ctttgatttg    600
aatgcggtta taaatgttgg agaggccaaa acaaaaata atttgtaga atcatttatt      660 cattttgagt cagtggaaga aatggaagct ctaaactcca acgggaagaa aataaacttc    720
caaccttctt tgtcgatgcc tctaatggga tttgctggga attggaacca cgaaccaatc    780
cttgataaat gggcttggga agaagggtca agatcaaaaa cactgggagg ttatgatgat    840
gatggtaaac cgaaaattcc aggaacctta aataagggaa ttggtggaga acatggtata    900
gataaattta atccagcagg agttatacaa aatagaaag ataaaaatac aacatccctg     960
gatcaaaatc cagaattatt tgctttcaat aacgaaggga tcaacgctcc atcatcaagt     1020
ggttctaaga ttgctaacat ttatccttta gattcaaatg aaatcctca agatgctcaa     1080 cttgaaagag gattaacacc ttctccactt gtattaagaa gtgcagaaga aggattgatt    1140
```

-continued

| | |
|---|---|
| tcaatagtaa atacaaataa agagggagaa aatcaaagag acttaaaagt catttcgaga | 1200 |
| gaacaccttta ttagaggaat tttaaattct aaaagcaatg atgcaaggg aatcaaatca | 1260 |
| tctaaactaa aagtttgggg tgacttgaag tgggatggac tcatctataa tcctagaggt | 1320 |
| agagaagaaa atgcaccaga aagtaaggat aatcaagatc ctgctactaa gataagaggt | 1380 |
| caatttgaac cgattgcgga aggtcaatat ttctataaat ttaaatatag attaactaaa | 1440 |
| gattacccat ggcaggtttc ctatattcct gtaaaaattg ataacaccgc ccctaagatt | 1500 |
| gtttcggttg attttttcaaa tcctgaaaaa attaagttga ttacaaagga tacttatcat | 1560 |
| aaggtaaaag atcagtataa gaatgaaacg ctatttgcga gagatcaaaa agaacatcct | 1620 |
| gaaaaatttg acgagattgc gaacgaagtt tggtatgctg gcgccgctct tgttaatgaa | 1680 |
| gatggagagg ttgaaaaaaa tcttgaagta acttacgcag gtgagggtca aggaagaaat | 1740 |
| agaaaacttg ataaagacgg aaataccatt tatgaaatta aaggtgcggg agatttaagg | 1800 |
| ggaaaaatca ttgaagtcat tgcattagat ggttctagca atttcacaaa gattcataga | 1860 |
| attaaatttg ctaatcaggc tgatgaaaag gggatgattt cctattatct agtagatcct | 1920 |
| gatcaagatt catctaaata tcaa | 1944 |

<210> SEQ ID NO 31
<211> LENGTH: 1986
<212> TYPE: DNA
<213> ORGANISM: Streptococcus pneumoniae

<400> SEQUENCE: 31

| | |
|---|---|
| atggtagtct tagcagacac atctagctct gaagatgctt taaacatctc tgataaagaa | 60 |
| aaagtagcag aaaataaaga gaaacatgaa aatatccata gtgctatgga aacttcacag | 120 |
| gatttaaag agaagaaaac agcagtcatt aaggaaaaag aagttgttag taaaaatcct | 180 |
| gtgatagaca ataacactag caatgaagaa gcaaaaatca agaagaaaa ttccaataaa | 240 |
| tcccaaggag attatacgga ctcatttgtg aataaaaaca cagaaaatcc caaaaaagaa | 300 |
| gataaagttg tctatattgc tgaatttaaa gataaagaat ctggagaaaa agcaatcaag | 360 |
| gaactatcca gtcttaagaa tacaaaagtt ttatatactt atgatagaat ttttaacggt | 420 |
| agtgccatag aaacaactcc agataacttg gacaaaatta acaaatagaa ggtatttca | 480 |
| tcggttgaaa gggcacaaaa agtccaaccc atgatgaatc atgccagaaa ggaaattgga | 540 |
| gttgaggaag ctattgatta cctaaagtct atcaatgctc cgtttgggaa aaattttgat | 600 |
| ggtagaggta tggtcatttc aaatatcgat actggaacag attatagaca taaggctatg | 660 |
| agaatcgatg atgatgccaa agcctcaatg agatttaaaa agaagacctt aaaaggcact | 720 |
| gataaaaatt attggttgag tgataaaatc cctcatgcgt tcaattatta taatggtggc | 780 |
| aaaatcactg tagaaaaata tgatgatgga agggattatt ttgacccaca tgggatgcat | 840 |
| attgcaggga ttcttgctgg aaatgatact gaacaagaca tcaaaaactt aacggcata | 900 |
| gatggaattg cacctaatgc acaaattttc tcttacaaaa tgtattctga cgcaggatct | 960 |
| gggtttgcgg tgatgaaac aatgtttcat gctattgaag attctatcaa acacaacgtt | 1020 |
| gatgttgttt cggtatcatc tggttttaca ggaacaggtc ttgtaggtga aaatattgg | 1080 |
| caagctattc gggcattaag aaaagcaggc attccaatgg ttgtcgctac gggtaactat | 1140 |
| gcgacttctg cttcaagttc ttcatgggat ttagtagcaa ataatcatct gaaaatgacc | 1200 |
| gacactggaa atgtaacacg aactgcagca catgaagatg cgatagcggt cgcttctgct | 1260 |

```
aaaaatcaaa cagttgagtt tgataaagtt aacataggtg gagaaagttt taaatacaga   1320 aatataggg ccttttcga taagagtaaa atcacaacaa atgaagatgg aacaaaagct   1380
cctagtaaat taaaatttgt atatataggc aaggggcaag accaagattt gataggtttg   1440
gatcttaggg gcaaaattgc agtaatggat agaatttata caaggatttt aaaaaatgct   1500
tttaaaaaag ctatggataa gggtgcacgc gccattatgg ttgtaaatac tgtaaattac   1560
tacaatagag ataattggac agagcttcca gctatgggat atgaagcgga tgaaggtact   1620
aaaagtcaag tgttttcaat ttcaggagat gatggtgtaa agctatggaa catgattaat   1680
cctgataaaa aaactgaagt caaaagaaat aataaagaag attttaaaga taaattggag   1740
caatactatc caattgatat ggaaagtttt aattccaaca aaccgaatgt aggtgacgaa   1800
aaagagattg actttaagtt tgcacctgac acagacaaag aactctataa agaagatatc   1860
atcgttccag caggatctac atcttggggg ccaagaatag atttacttt aaaacccgat   1920 gtttcagcac ctggtaaaaa tattaaatcc acgcttaatg ttattaatgg caaatcaact   1980
tatggc                                                             1986
```

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 32

His His His His His His
1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Ser Tyr Tyr His His His His His His
1               5                   10

<210> SEQ ID NO 34
<211> LENGTH: 9
<212> TYPE: PRT
<213> ORGANISM: Streptococcus pneumoniae

<400> SEQUENCE: 34

Ala Ile Ile Asp Gly Pro Trp Lys Ala
1               5

<210> SEQ ID NO 35
<211> LENGTH: 9
<212> TYPE: PRT
<213> ORGANISM: Streptococcus pneumoniae

<400> SEQUENCE: 35

Val Met Met Ala Pro Tyr Asp Arg Val
1               5

<210> SEQ ID NO 36
<211> LENGTH: 9

```
<212> TYPE: PRT
<213> ORGANISM: Streptococcus pneumoniae

<400> SEQUENCE: 36

Ser Ile Ala Gly Ile Asn Tyr Ala Lys
1               5

<210> SEQ ID NO 37
<211> LENGTH: 9
<212> TYPE: PRT
<213> ORGANISM: Streptococcus pneumoniae

<400> SEQUENCE: 37

Val Trp Asp Pro Ala Lys Asn Met Leu
1               5

<210> SEQ ID NO 38
<211> LENGTH: 9
<212> TYPE: PRT
<213> ORGANISM: Streptococcus pneumoniae

<400> SEQUENCE: 38

Gln Pro Leu Pro Asn Ile Ser Gln Met
1               5

<210> SEQ ID NO 39
<211> LENGTH: 9
<212> TYPE: PRT
<213> ORGANISM: Streptococcus pneumoniae

<400> SEQUENCE: 39

Ala Pro Tyr Asp Arg Val Gly Ser Leu
1               5

<210> SEQ ID NO 40
<211> LENGTH: 9
<212> TYPE: PRT
<213> ORGANISM: Streptococcus pneumoniae

<400> SEQUENCE: 40

Ala Pro Ala Val Ile Glu Ser Leu Val
1               5

<210> SEQ ID NO 41
<211> LENGTH: 9
<212> TYPE: PRT
<213> ORGANISM: Streptococcus pneumoniae

<400> SEQUENCE: 41

Phe Tyr Tyr Thr Tyr Gly Leu Leu Ala
1               5

<210> SEQ ID NO 42
<211> LENGTH: 8
<212> TYPE: PRT
<213> ORGANISM: Streptococcus pneumoniae

<400> SEQUENCE: 42

Ser Lys Tyr Ala Phe Ala Gly Glu
1               5

<210> SEQ ID NO 43
<211> LENGTH: 8
<212> TYPE: PRT
<213> ORGANISM: Streptococcus pneumoniae
```

<400> SEQUENCE: 43

Thr Glu Gly Ala Gly Asn Leu Ile
1               5

<210> SEQ ID NO 44
<211> LENGTH: 9
<212> TYPE: PRT
<213> ORGANISM: Streptococcus pneumoniae

<400> SEQUENCE: 44

Leu Ala Asp Trp Thr Asn Phe Tyr Tyr
1               5

<210> SEQ ID NO 45
<211> LENGTH: 9
<212> TYPE: PRT
<213> ORGANISM: Streptococcus pneumoniae

<400> SEQUENCE: 45

Ser Leu Val Met Tyr Tyr Asn Lys Asp
1               5

<210> SEQ ID NO 46
<211> LENGTH: 9
<212> TYPE: PRT
<213> ORGANISM: Streptococcus pneumoniae

<400> SEQUENCE: 46

Lys Glu Ala Gly Val Lys Val Thr Leu
1               5

<210> SEQ ID NO 47
<211> LENGTH: 9
<212> TYPE: PRT
<213> ORGANISM: Streptococcus pneumoniae

<400> SEQUENCE: 47

Lys Ser Thr Ala Val Leu Gly Thr Val
1               5

<210> SEQ ID NO 48
<211> LENGTH: 9
<212> TYPE: PRT
<213> ORGANISM: Streptococcus pneumoniae

<400> SEQUENCE: 48

Gly Ala Lys Thr Asp Asp Thr Thr Lys
1               5

<210> SEQ ID NO 49
<211> LENGTH: 9
<212> TYPE: PRT
<213> ORGANISM: Streptococcus pneumoniae

<400> SEQUENCE: 49

Ser Gln Lys Phe Val Asp Phe Leu Val
1               5

<210> SEQ ID NO 50
<211> LENGTH: 9
<212> TYPE: PRT
<213> ORGANISM: Streptococcus pneumoniae

<400> SEQUENCE: 50

Gln Ala Phe Lys Asp Ala Lys Val Asn
1               5

<210> SEQ ID NO 51
<211> LENGTH: 9
<212> TYPE: PRT
<213> ORGANISM: Streptococcus pneumoniae

<400> SEQUENCE: 51

Ala Val Ile Glu Ser Leu Val Met Tyr
1               5

<210> SEQ ID NO 52
<211> LENGTH: 9
<212> TYPE: PRT
<213> ORGANISM: Streptococcus pneumoniae

<400> SEQUENCE: 52

Asp Ala Lys Thr Ala Ala Asn Asp Ala
1               5

<210> SEQ ID NO 53
<211> LENGTH: 9
<212> TYPE: PRT
<213> ORGANISM: Streptococcus pneumoniae

<400> SEQUENCE: 53

Tyr Gly Val Ala Thr Ile Pro Thr Leu
1               5

<210> SEQ ID NO 54
<211> LENGTH: 9
<212> TYPE: PRT
<213> ORGANISM: Streptococcus pneumoniae

<400> SEQUENCE: 54

Lys Thr Ala Ala Ile Ile Asp Gly Pro
1               5

<210> SEQ ID NO 55
<211> LENGTH: 9
<212> TYPE: PRT
<213> ORGANISM: Streptococcus pneumoniae

<400> SEQUENCE: 55

Lys Ala Tyr Glu Lys Glu Ala Gly Val
1               5

<210> SEQ ID NO 56
<211> LENGTH: 9
<212> TYPE: PRT
<213> ORGANISM: Streptococcus pneumoniae

<400> SEQUENCE: 56

Ala Gly Asn Gly Ala Tyr Val Phe Gly
1               5

<210> SEQ ID NO 57
<211> LENGTH: 9
<212> TYPE: PRT
<213> ORGANISM: Streptococcus pneumoniae

<400> SEQUENCE: 57

Ala Trp Val Ile Pro Gln Ala Val Lys

```
<210> SEQ ID NO 58
<211> LENGTH: 9
<212> TYPE: PRT
<213> ORGANISM: Streptococcus pneumoniae

<400> SEQUENCE: 58

Ala Leu Gly Leu Val Ala Ala Gly Val
1               5

<210> SEQ ID NO 59
<211> LENGTH: 9
<212> TYPE: PRT
<213> ORGANISM: Streptococcus pneumoniae

<400> SEQUENCE: 59

Glu Leu Thr Gly Tyr Glu Ile Glu Val
1               5

<210> SEQ ID NO 60
<211> LENGTH: 9
<212> TYPE: PRT
<213> ORGANISM: Streptococcus pneumoniae

<400> SEQUENCE: 60

Ala Val Asn Asn Leu Ser Tyr Thr Lys
1               5

<210> SEQ ID NO 61
<211> LENGTH: 9
<212> TYPE: PRT
<213> ORGANISM: Streptococcus pneumoniae

<400> SEQUENCE: 61

Thr Tyr Leu Pro Ala Glu Ala Asp Ile
1               5

<210> SEQ ID NO 62
<211> LENGTH: 9
<212> TYPE: PRT
<213> ORGANISM: Streptococcus pneumoniae

<400> SEQUENCE: 62

Arg Tyr Asn Met Ala Val Asn Asn Leu
1               5

<210> SEQ ID NO 63
<211> LENGTH: 9
<212> TYPE: PRT
<213> ORGANISM: Streptococcus pneumoniae

<400> SEQUENCE: 63

Asp Phe Gln Gln Ile Met Val Arg Leu
1               5

<210> SEQ ID NO 64
<211> LENGTH: 9
<212> TYPE: PRT
<213> ORGANISM: Streptococcus pneumoniae

<400> SEQUENCE: 64

Glu His Thr Asp Asn Pro Thr Ile Leu
1               5
```

```
<210> SEQ ID NO 65
<211> LENGTH: 9
<212> TYPE: PRT
<213> ORGANISM: Streptococcus pneumoniae

<400> SEQUENCE: 65

Ala Pro Ile Ala Gln Asn Pro Asn Val
1               5

<210> SEQ ID NO 66
<211> LENGTH: 9
<212> TYPE: PRT
<213> ORGANISM: Streptococcus pneumoniae

<400> SEQUENCE: 66

Leu Pro Ser Asp Gln Gln Pro Tyr Val
1               5

<210> SEQ ID NO 67
<211> LENGTH: 9
<212> TYPE: PRT
<213> ORGANISM: Streptococcus pneumoniae

<400> SEQUENCE: 67

Tyr Val Tyr Pro Leu Leu Ala Gln Gly
1               5

<210> SEQ ID NO 68
<211> LENGTH: 9
<212> TYPE: PRT
<213> ORGANISM: Streptococcus pneumoniae

<400> SEQUENCE: 68

Gln Gly Leu Asp Asn Leu Lys Val Ile
1               5

<210> SEQ ID NO 69
<211> LENGTH: 8
<212> TYPE: PRT
<213> ORGANISM: Streptococcus pneumoniae

<400> SEQUENCE: 69

Lys Tyr Leu Tyr Ala Ala Pro Ile
1               5

<210> SEQ ID NO 70
<211> LENGTH: 8
<212> TYPE: PRT
<213> ORGANISM: Streptococcus pneumoniae

<400> SEQUENCE: 70

Gly Glu Leu Thr Gly Tyr Glu Ile
1               5

<210> SEQ ID NO 71
<211> LENGTH: 9
<212> TYPE: PRT
<213> ORGANISM: Streptococcus pneumoniae

<400> SEQUENCE: 71

Asn Pro Asn Val Leu Val Val Lys Lys
1               5

<210> SEQ ID NO 72
```

```
<211> LENGTH: 9
<212> TYPE: PRT
<213> ORGANISM: Streptococcus pneumoniae

<400> SEQUENCE: 72

Lys Leu Ser Lys Gln Phe Phe Gly Asp
1               5

<210> SEQ ID NO 73
<211> LENGTH: 9
<212> TYPE: PRT
<213> ORGANISM: Streptococcus pneumoniae

<400> SEQUENCE: 73

Gly Ser Pro Arg Pro Phe Ile Tyr Glu
1               5

<210> SEQ ID NO 74
<211> LENGTH: 9
<212> TYPE: PRT
<213> ORGANISM: Streptococcus pneumoniae

<400> SEQUENCE: 74

Ala Val Asn Asn Leu Ser Tyr Thr Lys
1               5

<210> SEQ ID NO 75
<211> LENGTH: 9
<212> TYPE: PRT
<213> ORGANISM: Streptococcus pneumoniae

<400> SEQUENCE: 75

Lys Ile Phe Asp Lys Ile Gly Val Glu
1               5

<210> SEQ ID NO 76
<211> LENGTH: 9
<212> TYPE: PRT
<213> ORGANISM: Streptococcus pneumoniae

<400> SEQUENCE: 76

Met Val Arg Leu Ser Asp Gly Gln Phe
1               5

<210> SEQ ID NO 77
<211> LENGTH: 9
<212> TYPE: PRT
<213> ORGANISM: Streptococcus pneumoniae

<400> SEQUENCE: 77

Tyr Val Tyr Pro Leu Leu Ala Gln Gly
1               5

<210> SEQ ID NO 78
<211> LENGTH: 9
<212> TYPE: PRT
<213> ORGANISM: Streptococcus pneumoniae

<400> SEQUENCE: 78

Val Val Gln Ala Thr Thr Ser Ala Lys
1               5

<210> SEQ ID NO 79
<211> LENGTH: 9
<212> TYPE: PRT
```

<213> ORGANISM: Streptococcus pneumoniae

<400> SEQUENCE: 79

Thr Leu Glu Lys Leu Ser Lys Gln Phe
1               5

<210> SEQ ID NO 80
<211> LENGTH: 9
<212> TYPE: PRT
<213> ORGANISM: Streptococcus pneumoniae

<400> SEQUENCE: 80

Val Ala Ala Gly Val Leu Ala Ala Cys
1               5

<210> SEQ ID NO 81
<211> LENGTH: 9
<212> TYPE: PRT
<213> ORGANISM: Streptococcus pneumoniae

<400> SEQUENCE: 81

Leu Asp Asn Leu Lys Val Ile Glu Leu
1               5

<210> SEQ ID NO 82
<211> LENGTH: 9
<212> TYPE: PRT
<213> ORGANISM: Streptococcus pneumoniae

<400> SEQUENCE: 82

Asn Met Ala Val Asn Asn Leu Ser Tyr
1               5

<210> SEQ ID NO 83
<211> LENGTH: 9
<212> TYPE: PRT
<213> ORGANISM: Streptococcus pneumoniae

<400> SEQUENCE: 83

Arg Leu Leu Asp Leu Ala Pro Gln Val
1               5

<210> SEQ ID NO 84
<211> LENGTH: 9
<212> TYPE: PRT
<213> ORGANISM: Streptococcus pneumoniae

<400> SEQUENCE: 84

Met Leu Glu Ile Pro Ala His Gln Ile
1               5

<210> SEQ ID NO 85
<211> LENGTH: 9
<212> TYPE: PRT
<213> ORGANISM: Streptococcus pneumoniae

<400> SEQUENCE: 85

Lys Asn Phe Phe Ala His His Pro Lys
1               5

<210> SEQ ID NO 86
<211> LENGTH: 9
<212> TYPE: PRT
<213> ORGANISM: Streptococcus pneumoniae

<400> SEQUENCE: 86

Lys Val Ile Leu Ala Gly His Ser Lys
1               5

<210> SEQ ID NO 87
<211> LENGTH: 9
<212> TYPE: PRT
<213> ORGANISM: Streptococcus pneumoniae

<400> SEQUENCE: 87

Ser Phe Asp Asn Leu Val Ser Thr Leu
1               5

<210> SEQ ID NO 88
<211> LENGTH: 9
<212> TYPE: PRT
<213> ORGANISM: Streptococcus pneumoniae

<400> SEQUENCE: 88

Tyr Tyr Asp Leu Pro Leu Asn Glu Leu
1               5

<210> SEQ ID NO 89
<211> LENGTH: 9
<212> TYPE: PRT
<213> ORGANISM: Streptococcus pneumoniae

<400> SEQUENCE: 89

Tyr Phe Asp Leu Phe Phe Gly Thr Ile
1               5

<210> SEQ ID NO 90
<211> LENGTH: 9
<212> TYPE: PRT
<213> ORGANISM: Streptococcus pneumoniae

<400> SEQUENCE: 90

Ala Leu Glu Tyr Ile His His Leu Phe
1               5

<210> SEQ ID NO 91
<211> LENGTH: 9
<212> TYPE: PRT
<213> ORGANISM: Streptococcus pneumoniae

<400> SEQUENCE: 91

Leu Pro Leu Asn Glu Leu Asp Ile Leu
1               5

<210> SEQ ID NO 92
<211> LENGTH: 9
<212> TYPE: PRT
<213> ORGANISM: Streptococcus pneumoniae

<400> SEQUENCE: 92

Ile Pro Gln Gly Ser Ile Ile Gly Met
1               5

<210> SEQ ID NO 93
<211> LENGTH: 9
<212> TYPE: PRT
<213> ORGANISM: Streptococcus pneumoniae

<400> SEQUENCE: 93

Asp Pro Glu Leu Gln Lys Gln Phe Ala
1               5

<210> SEQ ID NO 94
<211> LENGTH: 9
<212> TYPE: PRT
<213> ORGANISM: Streptococcus pneumoniae

<400> SEQUENCE: 94

Ala Val Tyr Thr Phe Asp Ala Pro Gly
1               5

<210> SEQ ID NO 95
<211> LENGTH: 9
<212> TYPE: PRT
<213> ORGANISM: Streptococcus pneumoniae

<400> SEQUENCE: 95

Gln Ser Leu Thr Pro Glu Glu Arg Glu
1               5

<210> SEQ ID NO 96
<211> LENGTH: 8
<212> TYPE: PRT
<213> ORGANISM: Streptococcus pneumoniae

<400> SEQUENCE: 96

Ala Ile Tyr Ala Ala Ser Gln Ile
1               5

<210> SEQ ID NO 97
<211> LENGTH: 8
<212> TYPE: PRT
<213> ORGANISM: Streptococcus pneumoniae

<400> SEQUENCE: 97

Leu Glu Ile Pro Ala His Gln Ile
1               5

<210> SEQ ID NO 98
<211> LENGTH: 9
<212> TYPE: PRT
<213> ORGANISM: Streptococcus pneumoniae

<400> SEQUENCE: 98

Leu Leu Asp Leu Ala Pro Gln Val Pro
1               5

<210> SEQ ID NO 99
<211> LENGTH: 9
<212> TYPE: PRT
<213> ORGANISM: Streptococcus pneumoniae

<400> SEQUENCE: 99

Trp Gln Ile Glu Asp Lys His Phe Val
1               5

<210> SEQ ID NO 100
<211> LENGTH: 9
<212> TYPE: PRT
<213> ORGANISM: Streptococcus pneumoniae

<400> SEQUENCE: 100

Thr Leu Gly Arg Leu Thr Gln Leu Leu
1               5

<210> SEQ ID NO 101
<211> LENGTH: 9
<212> TYPE: PRT
<213> ORGANISM: Streptococcus pneumoniae

<400> SEQUENCE: 101

Leu Tyr Phe Asp Leu Phe Phe Gly Thr
1               5

<210> SEQ ID NO 102
<211> LENGTH: 9
<212> TYPE: PRT
<213> ORGANISM: Streptococcus pneumoniae

<400> SEQUENCE: 102

Ser Ile Asn Asp Leu Ala Ser Leu Lys
1               5

<210> SEQ ID NO 103
<211> LENGTH: 9
<212> TYPE: PRT
<213> ORGANISM: Streptococcus pneumoniae

<400> SEQUENCE: 103

Ser Ile Asn Asp Leu Ala Ser Leu Lys
1               5

<210> SEQ ID NO 104
<211> LENGTH: 9
<212> TYPE: PRT
<213> ORGANISM: Streptococcus pneumoniae

<400> SEQUENCE: 104

Tyr Tyr Asp Leu Pro Leu Asn Glu Leu
1               5

<210> SEQ ID NO 105
<211> LENGTH: 9
<212> TYPE: PRT
<213> ORGANISM: Streptococcus pneumoniae

<400> SEQUENCE: 105

Gln Lys Val Ile Leu Ala Gly His Ser
1               5

<210> SEQ ID NO 106
<211> LENGTH: 9
<212> TYPE: PRT
<213> ORGANISM: Streptococcus pneumoniae

<400> SEQUENCE: 106

Gly Thr Asp Asp Ser Ile Ile Gly Trp
1               5

<210> SEQ ID NO 107
<211> LENGTH: 9
<212> TYPE: PRT
<213> ORGANISM: Streptococcus pneumoniae

<400> SEQUENCE: 107

Thr Tyr Leu Ser Phe Asp Asn Leu Val
1               5

```
<210> SEQ ID NO 108
<211> LENGTH: 9
<212> TYPE: PRT
<213> ORGANISM: Streptococcus pneumoniae

<400> SEQUENCE: 108

Phe Gly Thr Ile Leu Asp Ala Gly Ile
1               5

<210> SEQ ID NO 109
<211> LENGTH: 9
<212> TYPE: PRT
<213> ORGANISM: Streptococcus pneumoniae

<400> SEQUENCE: 109

Asn Gln Ile Thr Ala Val Tyr Thr Phe
1               5

<210> SEQ ID NO 110
<211> LENGTH: 9
<212> TYPE: PRT
<213> ORGANISM: Streptococcus pneumoniae

<400> SEQUENCE: 110

His Leu Asp Asn Leu Val Leu Lys Val
1               5

<210> SEQ ID NO 111
<211> LENGTH: 9
<212> TYPE: PRT
<213> ORGANISM: Streptococcus pneumoniae

<400> SEQUENCE: 111

Asp Leu Ile Ala Gly Arg Val His Leu
1               5

<210> SEQ ID NO 112
<211> LENGTH: 9
<212> TYPE: PRT
<213> ORGANISM: Streptococcus pneumoniae

<400> SEQUENCE: 112

Ile Leu Leu Pro Lys Asp Tyr Glu Lys
1               5

<210> SEQ ID NO 113
<211> LENGTH: 9
<212> TYPE: PRT
<213> ORGANISM: Streptococcus pneumoniae

<400> SEQUENCE: 113

Glu Tyr Gln Asp Gln Ile Gly Cys Leu
1               5

<210> SEQ ID NO 114
<211> LENGTH: 9
<212> TYPE: PRT
<213> ORGANISM: Streptococcus pneumoniae

<400> SEQUENCE: 114

Tyr Phe His Asp Gly Gln Asn Val Phe
1               5

<210> SEQ ID NO 115
<211> LENGTH: 9
```

<212> TYPE: PRT
<213> ORGANISM: Streptococcus pneumoniae

<400> SEQUENCE: 115

Asn Pro Asp Ile Ser Arg Met Ile Val
1               5

<210> SEQ ID NO 116
<211> LENGTH: 9
<212> TYPE: PRT
<213> ORGANISM: Streptococcus pneumoniae

<400> SEQUENCE: 116

Ile Pro Trp Ser Glu Asn Leu Pro Asp
1               5

<210> SEQ ID NO 117
<211> LENGTH: 9
<212> TYPE: PRT
<213> ORGANISM: Streptococcus pneumoniae

<400> SEQUENCE: 117

Gln Phe Gly Gly Lys Gly Val Glu Tyr
1               5

<210> SEQ ID NO 118
<211> LENGTH: 9
<212> TYPE: PRT
<213> ORGANISM: Streptococcus pneumoniae

<400> SEQUENCE: 118

Ile Gly Leu Glu Tyr Gln Asp Gln Ile
1               5

<210> SEQ ID NO 119
<211> LENGTH: 8
<212> TYPE: PRT
<213> ORGANISM: Streptococcus pneumoniae

<400> SEQUENCE: 119

Val Tyr Phe His Asp Gly Gln Asn
1               5

<210> SEQ ID NO 120
<211> LENGTH: 8
<212> TYPE: PRT
<213> ORGANISM: Streptococcus pneumoniae

<400> SEQUENCE: 120

Met Glu Val Val Lys Pro Phe Ile
1               5

<210> SEQ ID NO 121
<211> LENGTH: 9
<212> TYPE: PRT
<213> ORGANISM: Streptococcus pneumoniae

<400> SEQUENCE: 121

Tyr Leu Lys Met Lys Glu His Lys Leu
1               5

<210> SEQ ID NO 122
<211> LENGTH: 9
<212> TYPE: PRT
<213> ORGANISM: Streptococcus pneumoniae

<400> SEQUENCE: 122

Lys Leu Ser Pro Asp Gln Arg Ile Phe
1               5

<210> SEQ ID NO 123
<211> LENGTH: 9
<212> TYPE: PRT
<213> ORGANISM: Streptococcus pneumoniae

<400> SEQUENCE: 123

Arg Ile Phe Ile Tyr Val Gly Thr Glu
1               5

<210> SEQ ID NO 124
<211> LENGTH: 9
<212> TYPE: PRT
<213> ORGANISM: Streptococcus pneumoniae

<400> SEQUENCE: 124

Phe Ile Asp Glu Thr Tyr Arg Thr Lys
1               5

<210> SEQ ID NO 125
<211> LENGTH: 9
<212> TYPE: PRT
<213> ORGANISM: Streptococcus pneumoniae

<400> SEQUENCE: 125

Asp Thr Asp Arg Ser Tyr Pro Val Val
1               5

<210> SEQ ID NO 126
<211> LENGTH: 9
<212> TYPE: PRT
<213> ORGANISM: Streptococcus pneumoniae

<400> SEQUENCE: 126

Tyr Ile Asp Ser Ser Leu Cys Tyr Tyr
1               5

<210> SEQ ID NO 127
<211> LENGTH: 9
<212> TYPE: PRT
<213> ORGANISM: Streptococcus pneumoniae

<400> SEQUENCE: 127

Thr Gln Phe Ile Gly Leu Glu Tyr Gln
1               5

<210> SEQ ID NO 128
<211> LENGTH: 9
<212> TYPE: PRT
<213> ORGANISM: Streptococcus pneumoniae

<400> SEQUENCE: 128

Lys Asp Thr Asp Arg Ser Tyr Pro Val
1               5

<210> SEQ ID NO 129
<211> LENGTH: 9
<212> TYPE: PRT
<213> ORGANISM: Streptococcus pneumoniae

<400> SEQUENCE: 129

Leu Cys Tyr Tyr His Asp Leu Ile Ala
1               5

<210> SEQ ID NO 130
<211> LENGTH: 9
<212> TYPE: PRT
<213> ORGANISM: Streptococcus pneumoniae

<400> SEQUENCE: 130

Asn Val Phe Asn Ser Lys Glu Ser Phe
1               5

<210> SEQ ID NO 131
<211> LENGTH: 9
<212> TYPE: PRT
<213> ORGANISM: Streptococcus pneumoniae

<400> SEQUENCE: 131

Met Leu Lys Asp Lys Ile Ala Phe Leu
1               5

<210> SEQ ID NO 132
<211> LENGTH: 9
<212> TYPE: PRT
<213> ORGANISM: Streptococcus pneumoniae

<400> SEQUENCE: 132

Ser Leu Ala Asp Tyr Thr Tyr Lys Val
1               5

<210> SEQ ID NO 133
<211> LENGTH: 9
<212> TYPE: PRT
<213> ORGANISM: Streptococcus pneumoniae

<400> SEQUENCE: 133

Phe Leu Leu Leu Gly Ala Phe Tyr Leu
1               5

<210> SEQ ID NO 134
<211> LENGTH: 9
<212> TYPE: PRT
<213> ORGANISM: Streptococcus pneumoniae

<400> SEQUENCE: 134

Val Leu Ile Asp Gly Leu Ser Gln Leu
1               5

<210> SEQ ID NO 135
<211> LENGTH: 9
<212> TYPE: PRT
<213> ORGANISM: Streptococcus pneumoniae

<400> SEQUENCE: 135

Ile Leu Ala Ser Leu Gly Phe Leu Leu
1               5

<210> SEQ ID NO 136
<211> LENGTH: 9
<212> TYPE: PRT
<213> ORGANISM: Streptococcus pneumoniae

<400> SEQUENCE: 136

Gly Leu Ser Gln Leu Leu Pro Val Ile

```
<210> SEQ ID NO 137
<211> LENGTH: 9
<212> TYPE: PRT
<213> ORGANISM: Streptococcus pneumoniae

<400> SEQUENCE: 137

Phe Leu Leu Asn His Tyr Met Thr Val
1               5

<210> SEQ ID NO 138
<211> LENGTH: 9
<212> TYPE: PRT
<213> ORGANISM: Streptococcus pneumoniae

<400> SEQUENCE: 138

Met Leu Ile Pro Asn Val Asp Arg Ala
1               5

<210> SEQ ID NO 139
<211> LENGTH: 9
<212> TYPE: PRT
<213> ORGANISM: Streptococcus pneumoniae

<400> SEQUENCE: 139

Lys Leu Glu Glu Met Ala Lys Gln Val
1               5

<210> SEQ ID NO 140
<211> LENGTH: 9
<212> TYPE: PRT
<213> ORGANISM: Streptococcus pneumoniae

<400> SEQUENCE: 140

Val Leu Lys Arg Gly Val Tyr Thr Ile
1               5

<210> SEQ ID NO 141
<211> LENGTH: 9
<212> TYPE: PRT
<213> ORGANISM: Streptococcus pneumoniae

<400> SEQUENCE: 141

Lys Val Ile Ala Gly Leu Leu Arg Lys
1               5

<210> SEQ ID NO 142
<211> LENGTH: 9
<212> TYPE: PRT
<213> ORGANISM: Streptococcus pneumoniae

<400> SEQUENCE: 142

Thr Leu Asn Tyr Glu His Met Asn Lys
1               5

<210> SEQ ID NO 143
<211> LENGTH: 9
<212> TYPE: PRT
<213> ORGANISM: Streptococcus pneumoniae

<400> SEQUENCE: 143

Asn Ile Gly Tyr Phe Phe Phe Lys Lys
1               5
```

<210> SEQ ID NO 144
<211> LENGTH: 9
<212> TYPE: PRT
<213> ORGANISM: Streptococcus pneumoniae

<400> SEQUENCE: 144

Lys Tyr Thr Asp Val Ile Glu Lys Phe
1               5

<210> SEQ ID NO 145
<211> LENGTH: 9
<212> TYPE: PRT
<213> ORGANISM: Streptococcus pneumoniae

<400> SEQUENCE: 145

Lys Tyr Asp Asp Ser Val Ser Thr Ile
1               5

<210> SEQ ID NO 146
<211> LENGTH: 9
<212> TYPE: PRT
<213> ORGANISM: Streptococcus pneumoniae

<400> SEQUENCE: 146

Thr Phe Asn Gln Met Ile Lys Glu Leu
1               5

<210> SEQ ID NO 147
<211> LENGTH: 9
<212> TYPE: PRT
<213> ORGANISM: Streptococcus pneumoniae

<400> SEQUENCE: 147

Asp Tyr Pro Glu Thr Gln Ser Val Phe
1               5

<210> SEQ ID NO 148
<211> LENGTH: 9
<212> TYPE: PRT
<213> ORGANISM: Streptococcus pneumoniae

<400> SEQUENCE: 148

Thr Pro Arg Ala Ile Asn Asn Thr Leu
1               5

<210> SEQ ID NO 149
<211> LENGTH: 9
<212> TYPE: PRT
<213> ORGANISM: Streptococcus pneumoniae

<400> SEQUENCE: 149

Ala Pro Leu Leu Val Asn Gly Glu Leu
1               5

<210> SEQ ID NO 150
<211> LENGTH: 9
<212> TYPE: PRT
<213> ORGANISM: Streptococcus pneumoniae

<400> SEQUENCE: 150

Tyr Ile Asp His Thr Asn Val Ala Tyr
1               5

<210> SEQ ID NO 151

```
<211> LENGTH: 9
<212> TYPE: PRT
<213> ORGANISM: Streptococcus pneumoniae

<400> SEQUENCE: 151

Lys Gln Asn Gly Asp Ser Tyr Gly Tyr
1               5

<210> SEQ ID NO 152
<211> LENGTH: 9
<212> TYPE: PRT
<213> ORGANISM: Streptococcus pneumoniae

<400> SEQUENCE: 152

Phe Leu Leu Asn His Tyr Met Thr Val
1               5

<210> SEQ ID NO 153
<211> LENGTH: 9
<212> TYPE: PRT
<213> ORGANISM: Streptococcus pneumoniae

<400> SEQUENCE: 153

Phe Tyr Leu Tyr Asn Gly Asp Leu Ser
1               5

<210> SEQ ID NO 154
<211> LENGTH: 8
<212> TYPE: PRT
<213> ORGANISM: Streptococcus pneumoniae

<400> SEQUENCE: 154

Lys Ser Phe Ala Pro Leu Leu Val
1               5

<210> SEQ ID NO 155
<211> LENGTH: 8
<212> TYPE: PRT
<213> ORGANISM: Streptococcus pneumoniae

<400> SEQUENCE: 155

Asp Glu Thr Val Val Arg Thr Val
1               5

<210> SEQ ID NO 156
<211> LENGTH: 9
<212> TYPE: PRT
<213> ORGANISM: Streptococcus pneumoniae

<400> SEQUENCE: 156

Tyr Ile Asp His Thr Asn Val Ala Tyr
1               5

<210> SEQ ID NO 157
<211> LENGTH: 9
<212> TYPE: PRT
<213> ORGANISM: Streptococcus pneumoniae

<400> SEQUENCE: 157

Met Leu Lys Asp Lys Ile Ala Phe Leu
1               5

<210> SEQ ID NO 158
<211> LENGTH: 9
<212> TYPE: PRT
```

```
<213> ORGANISM: Streptococcus pneumoniae

<400> SEQUENCE: 158

Lys Leu Arg Phe Lys Ile Lys Thr Asp
1               5

<210> SEQ ID NO 159
<211> LENGTH: 9
<212> TYPE: PRT
<213> ORGANISM: Streptococcus pneumoniae

<400> SEQUENCE: 159

Lys Leu Glu Leu Phe Tyr Glu Thr Gly
1               5

<210> SEQ ID NO 160
<211> LENGTH: 9
<212> TYPE: PRT
<213> ORGANISM: Streptococcus pneumoniae

<400> SEQUENCE: 160

Lys Ile Ala Phe Leu Gly Ser Asn Ile
1               5

<210> SEQ ID NO 161
<211> LENGTH: 9
<212> TYPE: PRT
<213> ORGANISM: Streptococcus pneumoniae

<400> SEQUENCE: 161

Ser Val Pro Arg Thr Ser Tyr Leu Ser
1               5

<210> SEQ ID NO 162
<211> LENGTH: 9
<212> TYPE: PRT
<213> ORGANISM: Streptococcus pneumoniae

<400> SEQUENCE: 162

Phe Gly Phe Gly Leu Ser Leu Phe Ser
1               5

<210> SEQ ID NO 163
<211> LENGTH: 9
<212> TYPE: PRT
<213> ORGANISM: Streptococcus pneumoniae

<400> SEQUENCE: 163

Ser Thr Ile Arg Ser Ile Glu Gln Val
1               5

<210> SEQ ID NO 164
<211> LENGTH: 9
<212> TYPE: PRT
<213> ORGANISM: Streptococcus pneumoniae

<400> SEQUENCE: 164

Phe Arg Lys Thr Thr Asp Asn Pro Phe
1               5

<210> SEQ ID NO 165
<211> LENGTH: 9
<212> TYPE: PRT
<213> ORGANISM: Streptococcus pneumoniae
```

```
<400> SEQUENCE: 165

Thr Val Val Arg Thr Val Arg Asp Ser
1               5

<210> SEQ ID NO 166
<211> LENGTH: 9
<212> TYPE: PRT
<213> ORGANISM: Streptococcus pneumoniae

<400> SEQUENCE: 166

Ser Thr Ile Arg Ser Ile Glu Gln Val
1               5

<210> SEQ ID NO 167
<211> LENGTH: 9
<212> TYPE: PRT
<213> ORGANISM: Streptococcus pneumoniae

<400> SEQUENCE: 167

Asp Gly Leu Ser Gln Leu Leu Pro Val
1               5

<210> SEQ ID NO 168
<211> LENGTH: 9
<212> TYPE: PRT
<213> ORGANISM: Streptococcus pneumoniae

<400> SEQUENCE: 168

Phe Gly Phe Gly Leu Ser Leu Phe Ser
1               5

<210> SEQ ID NO 169
<211> LENGTH: 9
<212> TYPE: PRT
<213> ORGANISM: Streptococcus pneumoniae

<400> SEQUENCE: 169

Lys Leu Val Asp Gln Gly Glu Gly Phe
1               5

<210> SEQ ID NO 170
<211> LENGTH: 9
<212> TYPE: PRT
<213> ORGANISM: Streptococcus pneumoniae

<400> SEQUENCE: 170

Ala Ile Val Thr Cys Met Asp Ser Arg
1               5

<210> SEQ ID NO 171
<211> LENGTH: 9
<212> TYPE: PRT
<213> ORGANISM: Streptococcus pneumoniae

<400> SEQUENCE: 171

Ala Gln Thr Phe Glu Asn Glu Pro Phe
1               5

<210> SEQ ID NO 172
<211> LENGTH: 9
<212> TYPE: PRT
<213> ORGANISM: Streptococcus pneumoniae

<400> SEQUENCE: 172
```

Ala Tyr Val Ala Leu His Gly Gln Leu
1               5

<210> SEQ ID NO 173
<211> LENGTH: 9
<212> TYPE: PRT
<213> ORGANISM: Streptococcus pneumoniae

<400> SEQUENCE: 173

Asp Asp Val Ile Ile Ser Gly Ala Ile
1               5

<210> SEQ ID NO 174
<211> LENGTH: 9
<212> TYPE: PRT
<213> ORGANISM: Streptococcus pneumoniae

<400> SEQUENCE: 174

Phe Glu Asn Glu Pro Phe Gln Glu Tyr
1               5

<210> SEQ ID NO 175
<211> LENGTH: 9
<212> TYPE: PRT
<213> ORGANISM: Streptococcus pneumoniae

<400> SEQUENCE: 175

Phe Met Gln Ala Asn Gln Ala Tyr Val
1               5

<210> SEQ ID NO 176
<211> LENGTH: 9
<212> TYPE: PRT
<213> ORGANISM: Streptococcus pneumoniae

<400> SEQUENCE: 176

Ile Ser Gln Gln Gln Met Gly Thr Arg
1               5

<210> SEQ ID NO 177
<211> LENGTH: 9
<212> TYPE: PRT
<213> ORGANISM: Streptococcus pneumoniae

<400> SEQUENCE: 177

Lys Pro Lys Thr Arg Val Ala Ile Val
1               5

<210> SEQ ID NO 178
<211> LENGTH: 9
<212> TYPE: PRT
<213> ORGANISM: Streptococcus pneumoniae

<400> SEQUENCE: 178

Leu His Gly Gln Leu Asn Leu Pro Leu
1               5

<210> SEQ ID NO 179
<211> LENGTH: 9
<212> TYPE: PRT
<213> ORGANISM: Streptococcus pneumoniae

<400> SEQUENCE: 179

Leu His Val Ala Gln Ala Leu Gly Leu
1               5

```
<210> SEQ ID NO 180
<211> LENGTH: 9
<212> TYPE: PRT
<213> ORGANISM: Streptococcus pneumoniae

<400> SEQUENCE: 180

Leu Pro Leu Lys Pro Lys Thr Arg Val
1               5

<210> SEQ ID NO 181
<211> LENGTH: 9
<212> TYPE: PRT
<213> ORGANISM: Streptococcus pneumoniae

<400> SEQUENCE: 181

Met Gly Thr Arg Glu Ile Val Val Leu
1               5

<210> SEQ ID NO 182
<211> LENGTH: 9
<212> TYPE: PRT
<213> ORGANISM: Streptococcus pneumoniae

<400> SEQUENCE: 182

Met Gln Leu Leu Ile Glu Ser Pro Leu
1               5

<210> SEQ ID NO 183
<211> LENGTH: 9
<212> TYPE: PRT
<213> ORGANISM: Streptococcus pneumoniae

<400> SEQUENCE: 183

Gln Ala Asn Gln Ala Tyr Val Ala Leu
1               5

<210> SEQ ID NO 184
<211> LENGTH: 9
<212> TYPE: PRT
<213> ORGANISM: Streptococcus pneumoniae

<400> SEQUENCE: 184

Gln Phe Met Gln Ala Asn Gln Ala Tyr
1               5

<210> SEQ ID NO 185
<211> LENGTH: 9
<212> TYPE: PRT
<213> ORGANISM: Streptococcus pneumoniae

<400> SEQUENCE: 185

Gln Leu Asn Leu Pro Leu Lys Pro Lys
1               5

<210> SEQ ID NO 186
<211> LENGTH: 9
<212> TYPE: PRT
<213> ORGANISM: Streptococcus pneumoniae

<400> SEQUENCE: 186

Gln Gln Met Gly Thr Arg Glu Ile Val
1               5
```

```
<210> SEQ ID NO 187
<211> LENGTH: 9
<212> TYPE: PRT
<213> ORGANISM: Streptococcus pneumoniae

<400> SEQUENCE: 187

Arg Glu Ile Val Val Leu His His Thr
1               5

<210> SEQ ID NO 188
<211> LENGTH: 9
<212> TYPE: PRT
<213> ORGANISM: Streptococcus pneumoniae

<400> SEQUENCE: 188

Ser Pro Leu Ile Pro Asp Asp Val Ile
1               5

<210> SEQ ID NO 189
<211> LENGTH: 9
<212> TYPE: PRT
<213> ORGANISM: Streptococcus pneumoniae

<400> SEQUENCE: 189

Ser Arg Leu His Val Ala Gln Ala Leu
1               5

<210> SEQ ID NO 190
<211> LENGTH: 9
<212> TYPE: PRT
<213> ORGANISM: Streptococcus pneumoniae

<400> SEQUENCE: 190

Thr Glu Asp Met Ile Arg Ser Leu Val
1               5

<210> SEQ ID NO 191
<211> LENGTH: 9
<212> TYPE: PRT
<213> ORGANISM: Streptococcus pneumoniae

<400> SEQUENCE: 191

Val Asp Val Ser Asp Gln Asp Phe Leu
1               5

<210> SEQ ID NO 192
<211> LENGTH: 9
<212> TYPE: PRT
<213> ORGANISM: Streptococcus pneumoniae

<400> SEQUENCE: 192

Val Ser Asp Gln Asp Phe Leu Pro Phe
1               5

<210> SEQ ID NO 193
<211> LENGTH: 9
<212> TYPE: PRT
<213> ORGANISM: Streptococcus pneumoniae

<400> SEQUENCE: 193

Val Thr Glu Asp Met Ile Arg Ser Leu
1               5

<210> SEQ ID NO 194
<211> LENGTH: 9
```

```
<212> TYPE: PRT
<213> ORGANISM: Streptococcus pneumoniae

<400> SEQUENCE: 194

Gly Ile Glu Val Glu Lys Pro Leu Tyr
1               5

<210> SEQ ID NO 195
<211> LENGTH: 9
<212> TYPE: PRT
<213> ORGANISM: Streptococcus pneumoniae

<400> SEQUENCE: 195

Ala Glu Ala His Leu Leu Tyr Arg Met
1               5

<210> SEQ ID NO 196
<211> LENGTH: 9
<212> TYPE: PRT
<213> ORGANISM: Streptococcus pneumoniae

<400> SEQUENCE: 196

Ala Leu Leu Asn Gln Asp Asn Met Arg
1               5

<210> SEQ ID NO 197
<211> LENGTH: 9
<212> TYPE: PRT
<213> ORGANISM: Streptococcus pneumoniae

<400> SEQUENCE: 197

Ala Pro Pro Glu Arg Asn Tyr Leu Tyr
1               5

<210> SEQ ID NO 198
<211> LENGTH: 9
<212> TYPE: PRT
<213> ORGANISM: Streptococcus pneumoniae

<400> SEQUENCE: 198

Ala Gln Asn Ser Tyr Ile His Ile Leu
1               5

<210> SEQ ID NO 199
<211> LENGTH: 9
<212> TYPE: PRT
<213> ORGANISM: Streptococcus pneumoniae

<400> SEQUENCE: 199

Ala Val Ala Ser Met Gly Thr Ala Leu
1               5

<210> SEQ ID NO 200
<211> LENGTH: 9
<212> TYPE: PRT
<213> ORGANISM: Streptococcus pneumoniae

<400> SEQUENCE: 200

Ala Tyr Leu Leu Thr Lys Thr Arg Ile
1               5

<210> SEQ ID NO 201
<211> LENGTH: 9
<212> TYPE: PRT
<213> ORGANISM: Streptococcus pneumoniae
```

<400> SEQUENCE: 201

Asp Ala Ala Lys Phe Tyr His Ala Ile
1               5

<210> SEQ ID NO 202
<211> LENGTH: 9
<212> TYPE: PRT
<213> ORGANISM: Streptococcus pneumoniae

<400> SEQUENCE: 202

Asp Thr Ala Leu Glu Glu Leu Glu Arg
1               5

<210> SEQ ID NO 203
<211> LENGTH: 9
<212> TYPE: PRT
<213> ORGANISM: Streptococcus pneumoniae

<400> SEQUENCE: 203

Glu Glu Tyr Gln Gly Val Pro Phe Ile
1               5

<210> SEQ ID NO 204
<211> LENGTH: 9
<212> TYPE: PRT
<213> ORGANISM: Streptococcus pneumoniae

<400> SEQUENCE: 204

Glu Phe Leu Glu Lys Ile Ala Pro Leu
1               5

<210> SEQ ID NO 205
<211> LENGTH: 9
<212> TYPE: PRT
<213> ORGANISM: Streptococcus pneumoniae

<400> SEQUENCE: 205

Glu Phe Gln Val Leu Tyr Asp Leu Leu
1               5

<210> SEQ ID NO 206
<211> LENGTH: 9
<212> TYPE: PRT
<213> ORGANISM: Streptococcus pneumoniae

<400> SEQUENCE: 206

Glu His Val Glu His Leu Lys Arg Leu
1               5

<210> SEQ ID NO 207
<211> LENGTH: 9
<212> TYPE: PRT
<213> ORGANISM: Streptococcus pneumoniae

<400> SEQUENCE: 207

Glu Leu Ser Glu Val Glu Met Thr Arg
1               5

<210> SEQ ID NO 208
<211> LENGTH: 9
<212> TYPE: PRT
<213> ORGANISM: Streptococcus pneumoniae

<400> SEQUENCE: 208

```
Glu Ser Pro Leu Val Leu Asn Asp Tyr
1               5

<210> SEQ ID NO 209
<211> LENGTH: 9
<212> TYPE: PRT
<213> ORGANISM: Streptococcus pneumoniae

<400> SEQUENCE: 209

Gly Glu Lys Thr Pro Ser Phe Asn Val
1               5

<210> SEQ ID NO 210
<211> LENGTH: 9
<212> TYPE: PRT
<213> ORGANISM: Streptococcus pneumoniae

<400> SEQUENCE: 210

Gly Leu Cys Pro Phe His Gly Glu Lys
1               5

<210> SEQ ID NO 211
<211> LENGTH: 9
<212> TYPE: PRT
<213> ORGANISM: Streptococcus pneumoniae

<400> SEQUENCE: 211

Ile Gly Asp Met Pro Val Gln Ile Val
1               5

<210> SEQ ID NO 212
<211> LENGTH: 9
<212> TYPE: PRT
<213> ORGANISM: Streptococcus pneumoniae

<400> SEQUENCE: 212

Ile Thr Met Pro Val Thr Lys Gln Leu
1               5

<210> SEQ ID NO 213
<211> LENGTH: 9
<212> TYPE: PRT
<213> ORGANISM: Streptococcus pneumoniae

<400> SEQUENCE: 213

Lys Ala Leu Leu Asn Gln Asp Asn Met
1               5

<210> SEQ ID NO 214
<211> LENGTH: 9
<212> TYPE: PRT
<213> ORGANISM: Streptococcus pneumoniae

<400> SEQUENCE: 214

Lys Arg Leu Thr Lys Lys Leu Val Leu
1               5

<210> SEQ ID NO 215
<211> LENGTH: 9
<212> TYPE: PRT
<213> ORGANISM: Streptococcus pneumoniae

<400> SEQUENCE: 215

Leu Thr Lys Thr Arg Ile Ser Pro Ile
```

```
<210> SEQ ID NO 216
<211> LENGTH: 9
<212> TYPE: PRT
<213> ORGANISM: Streptococcus pneumoniae

<400> SEQUENCE: 216

Leu Val Leu Val Tyr Asp Gly Asp Lys
1               5

<210> SEQ ID NO 217
<211> LENGTH: 9
<212> TYPE: PRT
<213> ORGANISM: Streptococcus pneumoniae

<400> SEQUENCE: 217

Met Arg Ala Glu Ala His Leu Leu Tyr
1               5

<210> SEQ ID NO 218
<211> LENGTH: 9
<212> TYPE: PRT
<213> ORGANISM: Streptococcus pneumoniae

<400> SEQUENCE: 218

Asn Gly Pro Glu Asp Leu Ala Tyr Leu
1               5

<210> SEQ ID NO 219
<211> LENGTH: 9
<212> TYPE: PRT
<213> ORGANISM: Streptococcus pneumoniae

<400> SEQUENCE: 219

Gln Thr Glu Glu Val Glu Arg Ala Trp
1               5

<210> SEQ ID NO 220
<211> LENGTH: 9
<212> TYPE: PRT
<213> ORGANISM: Streptococcus pneumoniae

<400> SEQUENCE: 220

Ser Glu Ile Tyr Leu Met Glu Gly Phe
1               5

<210> SEQ ID NO 221
<211> LENGTH: 9
<212> TYPE: PRT
<213> ORGANISM: Streptococcus pneumoniae

<400> SEQUENCE: 221

Ser Pro His Gln Ala Leu Tyr Asp Met
1               5

<210> SEQ ID NO 222
<211> LENGTH: 9
<212> TYPE: PRT
<213> ORGANISM: Streptococcus pneumoniae

<400> SEQUENCE: 222

Val Asp Lys Gln Val Ile Glu Glu Ile
1               5
```

```
<210> SEQ ID NO 223
<211> LENGTH: 9
<212> TYPE: PRT
<213> ORGANISM: Streptococcus pneumoniae

<400> SEQUENCE: 223

Val Glu Met Thr Arg Asn Lys Ala Leu
1               5

<210> SEQ ID NO 224
<211> LENGTH: 9
<212> TYPE: PRT
<213> ORGANISM: Streptococcus pneumoniae

<400> SEQUENCE: 224

Val Leu Tyr Asp Leu Leu Gly Gln Tyr
1               5

<210> SEQ ID NO 225
<211> LENGTH: 9
<212> TYPE: PRT
<213> ORGANISM: Streptococcus pneumoniae

<400> SEQUENCE: 225

Val Pro Phe Ile Glu Ala Val Gln Ile
1               5

<210> SEQ ID NO 226
<211> LENGTH: 9
<212> TYPE: PRT
<213> ORGANISM: Streptococcus pneumoniae

<400> SEQUENCE: 226

Trp Tyr Gln Val Leu Ala Gln Asp Leu
1               5

<210> SEQ ID NO 227
<211> LENGTH: 9
<212> TYPE: PRT
<213> ORGANISM: Streptococcus pneumoniae

<400> SEQUENCE: 227

Tyr Leu Met Glu Gly Phe Met Asp Val
1               5

<210> SEQ ID NO 228
<211> LENGTH: 9
<212> TYPE: PRT
<213> ORGANISM: Streptococcus pneumoniae

<400> SEQUENCE: 228

Ala Ala Tyr Ala Pro Asn Glu Val Val
1               5

<210> SEQ ID NO 229
<211> LENGTH: 9
<212> TYPE: PRT
<213> ORGANISM: Streptococcus pneumoniae

<400> SEQUENCE: 229

Ala Gly Asp Leu Arg Gly Lys Ile Ile
1               5

<210> SEQ ID NO 230
```

<210> SEQ ID NO 230
<211> LENGTH: 9
<212> TYPE: PRT
<213> ORGANISM: Streptococcus pneumoniae

<400> SEQUENCE: 230

Asp Glu Ile Ala Asn Glu Val Trp Tyr
1               5

<210> SEQ ID NO 231
<211> LENGTH: 9
<212> TYPE: PRT
<213> ORGANISM: Streptococcus pneumoniae

<400> SEQUENCE: 231

Asp Asn Tyr Leu Ile Tyr Gly Asp Leu
1               5

<210> SEQ ID NO 232
<211> LENGTH: 9
<212> TYPE: PRT
<213> ORGANISM: Streptococcus pneumoniae

<400> SEQUENCE: 232

Asp Gln Lys Glu His Pro Glu Lys Phe
1               5

<210> SEQ ID NO 233
<211> LENGTH: 9
<212> TYPE: PRT
<213> ORGANISM: Streptococcus pneumoniae

<400> SEQUENCE: 233

Asp Ser Leu Thr Asp Arg Leu Lys Leu
1               5

<210> SEQ ID NO 234
<211> LENGTH: 9
<212> TYPE: PRT
<213> ORGANISM: Streptococcus pneumoniae

<400> SEQUENCE: 234

Glu Ala Lys Asn Lys Asn Lys Phe Val
1               5

<210> SEQ ID NO 235
<211> LENGTH: 9
<212> TYPE: PRT
<213> ORGANISM: Streptococcus pneumoniae

<400> SEQUENCE: 235

Glu Gly Gln Gly Arg Asn Arg Lys Leu
1               5

<210> SEQ ID NO 236
<211> LENGTH: 9
<212> TYPE: PRT
<213> ORGANISM: Streptococcus pneumoniae

<400> SEQUENCE: 236

Glu Ile Lys Gly Ala Gly Asp Leu Arg
1               5

<210> SEQ ID NO 237
<211> LENGTH: 9
<212> TYPE: PRT

```
<213> ORGANISM: Streptococcus pneumoniae

<400> SEQUENCE: 237

Glu Pro Ile Ala Glu Gly Gln Tyr Phe
1               5

<210> SEQ ID NO 238
<211> LENGTH: 9
<212> TYPE: PRT
<213> ORGANISM: Streptococcus pneumoniae

<400> SEQUENCE: 238

Glu Val Ser Glu Leu Lys Pro His Arg
1               5

<210> SEQ ID NO 239
<211> LENGTH: 9
<212> TYPE: PRT
<213> ORGANISM: Streptococcus pneumoniae

<400> SEQUENCE: 239

Gly Ala Phe Phe Asp Lys Ser Lys Ile
1               5

<210> SEQ ID NO 240
<211> LENGTH: 9
<212> TYPE: PRT
<213> ORGANISM: Streptococcus pneumoniae

<400> SEQUENCE: 240

Gly Asp Leu Lys Trp Asp Gly Leu Ile
1               5

<210> SEQ ID NO 241
<211> LENGTH: 9
<212> TYPE: PRT
<213> ORGANISM: Streptococcus pneumoniae

<400> SEQUENCE: 241

Gly Glu Val Glu Lys Asn Leu Glu Val
1               5

<210> SEQ ID NO 242
<211> LENGTH: 9
<212> TYPE: PRT
<213> ORGANISM: Streptococcus pneumoniae

<400> SEQUENCE: 242

Ile His Phe Glu Ser Val Glu Glu Met
1               5

<210> SEQ ID NO 243
<211> LENGTH: 9
<212> TYPE: PRT
<213> ORGANISM: Streptococcus pneumoniae

<400> SEQUENCE: 243

Ile Met Phe Ile Val Gly Ile Phe Leu
1               5

<210> SEQ ID NO 244
<211> LENGTH: 9
<212> TYPE: PRT
<213> ORGANISM: Streptococcus pneumoniae
```

```
<400> SEQUENCE: 244

Ile Pro Gly Thr Leu Asn Lys Gly Ile
1               5

<210> SEQ ID NO 245
<211> LENGTH: 9
<212> TYPE: PRT
<213> ORGANISM: Streptococcus pneumoniae

<400> SEQUENCE: 245

Ile Arg Tyr Gln Val Phe Thr Phe Lys
1               5

<210> SEQ ID NO 246
<211> LENGTH: 9
<212> TYPE: PRT
<213> ORGANISM: Streptococcus pneumoniae

<400> SEQUENCE: 246

Ile Ser Asp Lys Gly Gly Phe Asn Trp
1               5

<210> SEQ ID NO 247
<211> LENGTH: 9
<212> TYPE: PRT
<213> ORGANISM: Streptococcus pneumoniae

<400> SEQUENCE: 247

Ile Val Ser Glu Glu Asp Phe Ile Leu
1               5

<210> SEQ ID NO 248
<211> LENGTH: 9
<212> TYPE: PRT
<213> ORGANISM: Streptococcus pneumoniae

<400> SEQUENCE: 248

Lys Glu Ile Gly Val Glu Glu Ala Ile
1               5

<210> SEQ ID NO 249
<211> LENGTH: 9
<212> TYPE: PRT
<213> ORGANISM: Streptococcus pneumoniae

<400> SEQUENCE: 249

Lys Ile Val Val Lys Asp Phe Ala Arg
1               5

<210> SEQ ID NO 250
<211> LENGTH: 9
<212> TYPE: PRT
<213> ORGANISM: Streptococcus pneumoniae

<400> SEQUENCE: 250

Lys Lys Ile Asn Phe Gln Pro Ser Leu
1               5

<210> SEQ ID NO 251
<211> LENGTH: 9
<212> TYPE: PRT
<213> ORGANISM: Streptococcus pneumoniae

<400> SEQUENCE: 251
```

-continued

Lys Leu Lys Phe Val Tyr Ile Gly Lys
1               5

<210> SEQ ID NO 252
<211> LENGTH: 9
<212> TYPE: PRT
<213> ORGANISM: Streptococcus pneumoniae

<400> SEQUENCE: 252

Lys Val Tyr Tyr Gly Asn Asn Tyr Lys
1               5

<210> SEQ ID NO 253
<211> LENGTH: 9
<212> TYPE: PRT
<213> ORGANISM: Streptococcus pneumoniae

<400> SEQUENCE: 253

Lys Tyr Trp Gln Ala Ile Arg Ala Leu
1               5

<210> SEQ ID NO 254
<211> LENGTH: 9
<212> TYPE: PRT
<213> ORGANISM: Streptococcus pneumoniae

<400> SEQUENCE: 254

Leu His Ile Asp Asn Thr Arg Asp Phe
1               5

<210> SEQ ID NO 255
<211> LENGTH: 9
<212> TYPE: PRT
<213> ORGANISM: Streptococcus pneumoniae

<400> SEQUENCE: 255

Met Arg Phe Lys Lys Glu Asp Leu Lys
1               5

<210> SEQ ID NO 256
<211> LENGTH: 9
<212> TYPE: PRT
<213> ORGANISM: Streptococcus pneumoniae

<400> SEQUENCE: 256

Asn Glu Ser Val Val Asp Asn Tyr Leu
1               5

<210> SEQ ID NO 257
<211> LENGTH: 9
<212> TYPE: PRT
<213> ORGANISM: Streptococcus pneumoniae

<400> SEQUENCE: 257

Asn Glu Val Trp Tyr Ala Gly Ala Ala
1               5

<210> SEQ ID NO 258
<211> LENGTH: 9
<212> TYPE: PRT
<213> ORGANISM: Streptococcus pneumoniae

<400> SEQUENCE: 258

Asn Ile Asn Asp Ile Val Asp Gly Leu
1               5

```
<210> SEQ ID NO 259
<211> LENGTH: 9
<212> TYPE: PRT
<213> ORGANISM: Streptococcus pneumoniae

<400> SEQUENCE: 259

Gln Tyr Leu Leu Lys Asp Asn Ile Ile
1               5

<210> SEQ ID NO 260
<211> LENGTH: 9
<212> TYPE: PRT
<213> ORGANISM: Streptococcus pneumoniae

<400> SEQUENCE: 260

Ser Pro Arg Gln Gln Gly Ala Gly Leu
1               5

<210> SEQ ID NO 261
<211> LENGTH: 9
<212> TYPE: PRT
<213> ORGANISM: Streptococcus pneumoniae

<400> SEQUENCE: 261

Ser Arg Ser Lys Thr Leu Gly Gly Tyr
1               5

<210> SEQ ID NO 262
<211> LENGTH: 9
<212> TYPE: PRT
<213> ORGANISM: Streptococcus pneumoniae

<400> SEQUENCE: 262

Ser Ser Leu Lys Asn Thr Lys Val Leu
1               5

<210> SEQ ID NO 263
<211> LENGTH: 9
<212> TYPE: PRT
<213> ORGANISM: Streptococcus pneumoniae

<400> SEQUENCE: 263

Thr Ala Ala Val Ile Leu Ala Ala Tyr
1               5

<210> SEQ ID NO 264
<211> LENGTH: 9
<212> TYPE: PRT
<213> ORGANISM: Streptococcus pneumoniae

<400> SEQUENCE: 264

Trp Thr Glu Leu Pro Ala Met Gly Tyr
1               5
```

VACCINES AND COMPOSITIONS AGAINST *STREPTOCOCCUS PNEUMONIAE*

RELATED APPLICATIONS

This application is a divisional application of U.S. application Ser. No. 12/826,084, filed on Jun. 29, 2010, now U.S. patent Ser. No. 10/105,412, which claims the benefit of the filing date of U.S. Provisional Application No. 61/221,541, filed Jun. 29, 2009, U.S. Provisional Application No. 61/240,616, filed Sep. 8, 2009, U.S. Provisional Application No. 61/240,598, filed Sep. 8, 2009, and U.S. Provisional Application No. 61/316,267, filed Mar. 22, 2010. The entire teachings of the referenced applications are expressly incorporated herein by reference.

SEQUENCE LISTING

The instant application contains a Sequence Listing which has been submitted via EFSWeb and is hereby incorporated by reference in its entirety. Said ASCII copy, created on May 13, 2019, is named 2007781-0200 SL.txt and is 142932 bytes in size.

I. BACKGROUND

Pneumococcal disease continues to be a leading cause of sickness and death in the United States and throughout the world. Each year, millions of cases of pneumonia, meningitis, bacteremia, and otitis media are attributed to infection with the pathogen *Streptococcus pneumoniae*. *S. pneumoniae* is a Gram-positive encapsulated coccus that colonizes the nasopharynx in about 5-10% of healthy adults and 20-40% of healthy children. Normal colonization becomes infectious when *S. pneumoniae* is carried into the Eustachian tubes, nasal sinuses, lungs, bloodstream, meninges, joint spaces, bones and peritoneal cavity. *S. pneumoniae* has several virulence factors that enable the organism to evade the immune system. Examples include a polysaccharide capsule that prevents phagocytosis by host immune cells, proteases that inhibit complement-mediated opsonization, and proteins that cause lysis of host cells. In the polysaccharide capsule, the presence of complex polysaccharides forms the basis for dividing pneumococci into different serotypes. To date, 93 serotypes of *S. pneumoniae* have been identified.

Various pharmaceutical compositions have been used to harness an immune response against infection by *S. pneumoniae*. A polyvalent pneumococcal vaccine, PPV-23, was developed for preventing pneumonia and other invasive diseases due to *S. pneumoniae* in the adult and aging populations. The vaccine contains capsular polysaccharides (CPs) from 23 serotypes of *S. pneumoniae*. As T cell independent antigens, these CPs induce only short-lived antibody responses, necessitating repeated doses, which increases the risk of immunological tolerance. The antibodies raised against *S. pneumoniae*, termed anticapsular antibodies, are recognized as protective in adult and immunocompetent individuals. However, children under 2 years of age and immunocompromised individuals, including the elderly, do not respond well to T-cell independent antigens and, therefore, are not afforded optimal protection by PPV-23. A second *S. pneumoniae* vaccine, Prevnar, includes bacterial polysaccharides from 7 *S. pneumoniae* strains conjugated to the diphtheria toxoid protein. This vaccine induces both B and T cell responses. However, because it only protects against 7 pneumococcal serotypes, serotype replacement can render Prevnar ineffective. PPV-23 suffers from the same limitation. Serotype replacement has already been demonstrated in several clinical trials and epidemiologic studies, and raises the possibility that different formulations of the vaccines will need to be developed, presumably at even higher cost. Furthermore, both PPV-23 and Prevnar are expensive to manufacture, greatly limiting their availability in the developing world.

Thus, there remains a need to design more effective pharmaceutical compositions than the current strategies offer. In particular, such compositions need to incorporate novel or specific antigens that elicit an immune response against *S. pneumoniae*.

II. SUMMARY

*Streptococcus pneumoniae* is a major health concern, especially in very young, elderly, or immunocompromised patients. While DNA and protein sequence information for *S. pneumoniae* has been known for some time, and researchers have long attempted to produce vaccines against *S. pneumoniae*, a major problem was how to identify protective polypeptides from among the approximately 2100 genes in the *S. pneumoniae* genome. The instant application presents the results of whole-genome screens designed to identify the most immunogenic proteins in the *S. pneumoniae* genome. Several of the hits from the screen have been shown to protect against *S. pneumoniae* colonization in a mouse model. Accordingly, the present disclosure provides, inter alia, certain highly effective vaccines in *Streptococcus pneumoniae*. The vaccines may be used therapeutically or prophylactically. The present disclosure also provides specific antigens and methods for using the antigens to elicit an immune response against *S. pneumoniae*.

The present disclosure provides, for example, a vaccine formulation comprising a pharmaceutically acceptable carrier and one or more polypeptides having an amino acid sequence comprising any of SEQ ID NOS: 1-11 or an immunogenic fragment thereof, and optionally further comprising a polypeptide having an amino acid sequence comprising either of SEQ ID NOS: 12 or 13 or an immunogenic fragment thereof.

The present disclosure also provides a vaccine formulation comprising a pharmaceutically acceptable carrier and a polypeptide having an amino acid sequence consisting of SEQ ID NO: 11 or an immunogenic fragment thereof. In addition, the present disclosure provides a vaccine formulation comprising a pharmaceutically acceptable carrier and a polypeptide having an amino acid sequence comprising SEQ ID NO: 12.

Furthermore, the instant application provides a vaccine formulation comprising a pharmaceutically acceptable carrier and one or more polypeptides having an amino acid sequence comprising any of SEQ ID NOS: 14-21 or an immunogenic fragment thereof.

This application provides, inter alia, a method for treating a subject suffering from or susceptible to *S. pneumoniae* infection, comprising administering an effective amount of any of the vaccine formulations described herein.

The present disclosure further provides an immunogenic composition comprising a pharmaceutically acceptable carrier and two or more polypeptides having amino acid sequences comprising any of SEQ ID NOS: 1-13 or an immunogenic fragment thereof, wherein at least one of said polypeptides has an amino acid sequence comprising one of SEQ ID NOS: 1-10 or an immunogenic fragment thereof.

III. BRIEF DESCRIPTION OF THE DRAWINGS

FIG. 1 shows the concentration of IL-17 generated by blood samples from mice that were immunized with the indicated protein(s) and cholera toxin, then stimulated with killed, unencapsulated whole cell *S. pneumoniae*, as described in Example 5. The left panel shows the data in scatter format, and the right panel shows the average and standard deviation for each sample. Immunization group "All 3" represents animals immunized with a combination of SP2108, SP0148, and SP1634.

IV. DETAILED DESCRIPTION

Figure 1:
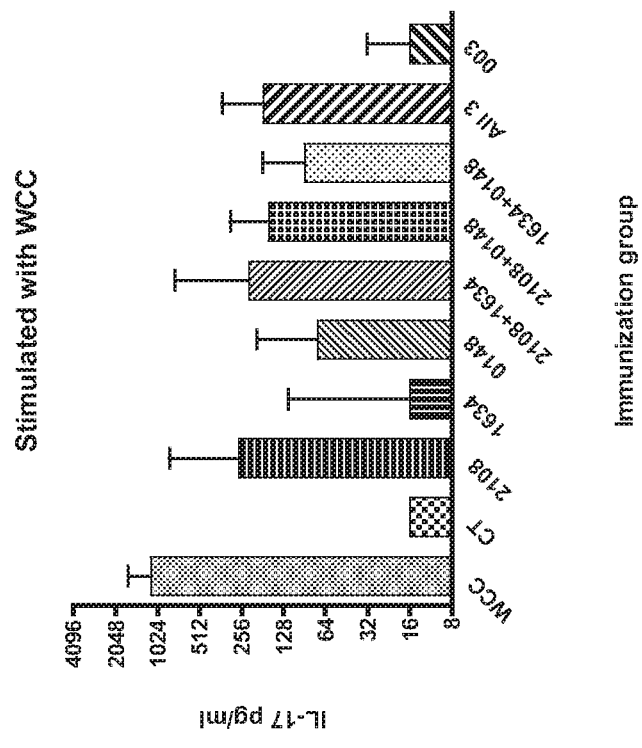
Figure 1:
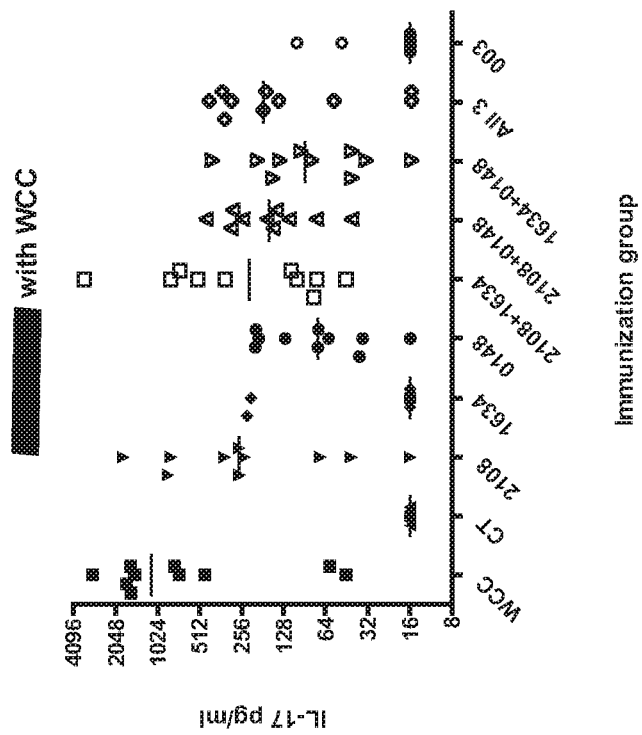

A. Specific Polypeptides and Nucleic Acids for Use in *S. pneumoniae* Vaccines and Immunogenic Compositions This application describes *S. pneumoniae* vaccines that include one or more of the polypeptides or genes listed in Table 1, or variants or fragments thereof as described below. The vaccine may include a polypeptide that comprises a sequence of Table 1 or a variant or immunogenic fragment thereof or a polypeptide that consists of a sequence of Table 1 or a variant or immunogenic fragment thereof. The DNA and protein sequence of each gene and polypeptide may be found by searching for the Locus Tag in the publicly available database, Entrez Gene (on the NCBI NIH web site on the World Wide Web, at www.ncbi.nlm.nih.gov/sites/entrez?db=gene), in the *Streptococcus pneumoniae* TIGR4 genome, and the indicated sequences are also included in this application.

TABLE 1

Immunogenic polypeptides for vaccine formulations

| Locus tag name and description | Protein SEQ ID No. | DNA SEQ ID No. | DNA GenBank Accession No. (from Mar. 30, 2010) |
|---|---|---|---|
| SP0024 | 1 | — | NC_003028.3\|:27381-27878 |
| SP0882 | 2 | — | NC_003028.3\|:831.804-832628 |
| SP0882N | 3 | 24 | — |
| SP0882 with exogenous leader | 4 | 25 | — |
| SP0882N with exogenous leader | 5 | 26 | — |
| SP0148 lacking signal sequence | 6 | 27 | — |
| SP0148 including signal sequence | 7 | 28 | — |
| SP1072 | 8 | — | NC_003028.3\|:1008420-1010180 |
| SP2108 including signal sequence | 9 | — | NC_003028.3\|:2020750-2022021 |
| SP2108 lacking signal sequence | 10 | 29 | — |
| SP0641M | 11 | 30 | — |
| SP0641 | 12 | — | NC_003028.3\|:2020750-2022021 |
| SP0641N | 13 | 31 | — |
| SP0882 consensus | 14 | — | — |
| SP0882N consensus | 15 | — | — |
| SP0882 consensus with exogenous leader | 16 | — | — |
| SP0882N consensus with exogenous leader | 17 | — | — |
| SP0148 consensus lacking signal sequence | 18 | — | — |
| SP0148 consensus including signal sequence | 19 | — | — |
| SP2108 consensus lacking signal sequence | 20 | — | — |
| SP2108 consensus including signal sequence | 21 | — | — |
| SP1634 | 22 | — | NC_003028.3\|:1534348-1535421 |
| SP0314 | 23 | — | NC_003028.3\|:287483-290683 |

Certain polypeptides of Table 1, and variants thereof, are described in greater detail below.

1. SP0024 (SEQ ID NO: 1) and Variants Thereof

SP0024 represents a hypothetical protein of 165 amino acids, containing a conserved carbonic anhydrase domain that extends from amino acid 27 to amino acid 163. Based on this consensus motif, SP0024 may be a zinc-binding protein.

In some embodiments, vaccines or pharmaceutical compositions comprising an *S. pneumoniae* polypeptide include a polypeptide containing at least 20 consecutive amino acid residues selected from SP0024. The polypeptide may also be a variant of the at least 20 residue fragment. In certain embodiments, the polypeptide includes no more than 150, 125, or 100 consecutive amino acids from SP0024.

2. SP0882 (SEQ ID NO: 2) and Variants Thereof

SP0882 is a conserved hypothetical protein of 274 amino acids. Much of the protein (amino acids 2-270) forms an esterase or lipase-like region.

In some embodiments, vaccines or pharmaceutical compositions comprising an *S. pneumoniae* polypeptide include a polypeptide containing at least 20 consecutive amino acid residues selected from SP0882. The polypeptide may also be a variant of the at least 20 residue fragment. In certain embodiments, the polypeptide includes no more than 250, 275, 200, 175, 150, 125, or 100 consecutive amino acids from SP0882.

One particular truncation variant named SP0882N consists of the N-terminal 130 amino acids of SP0882, and is shown as SEQ ID NO: 3. SP0882N includes a region that is particularly well conserved among different serotypes. In certain embodiments, a polypeptide comprising SP0882 or SP0882N, or an immunogenic fragment of either, also comprises an exogenous leader sequence. The leader sequence may be, for example, the leader sequence of SP2108. Two exemplary such polypeptides are SEQ ID NOS: 4 and 5.

Variants of DNA and protein sequences of SP0882 are described, inter alia, in US Patent Application Publication No. 2009/0215149 and International Applications WO2002/077021, WO98/18931, and WO2007/106407. A variant of SP0882N is disclosed in International Application WO2008/146164.

Sequence variation occurs at the protein level between different *S. pneumoniae* serotypes, and consensus sequences illustrating combinations of SP0882 sequences from different *S. pneumoniae* serotypes are provided as SEQ ID NOS: 14-17. Accordingly, in certain embodiments, the vaccine formulation comprises a polypeptide having an amino acid sequence comprising, or consisting of, any of SEQ ID NOS: 14-17, or an immunogenic fragment thereof (e.g., in place of a polypeptide having an amino acid sequence comprising one of SEQ ID NOS: 2-5).

Nucleic acid sequences encoding different variants of SP0882 are provided as SEQ ID NOS: 24-26, although due to degeneracy in the genetic code, other DNA sequences (including codon-optimized sequences) could encode these polypeptides.

3. SP0148 (SEQ ID NO: 7) and Variants Thereof

The protein SP0148 is named "ABC transporter, substrate-binding protein". Proteins of this class are typically extracellular proteins that interact transiently with a transmembrane protein complex. Such complexes use energy generated by ATP hydrolysis to translocate specific substrates across a cell membrane. SP0148 is a 276 amino acid protein that contains a conserved PBPb (periplasmic binding protein) domain, spanning amino acids 40-246, which is typical of membrane-bound transport complexes. In addition. SB0148 has a bacterial extracellular solute-binding proteins, family 3 domain which is largely co-extensive with the PBPb domain and extends from amino acid 40 to 244. In some embodiments, a vaccine or other composition comprises a truncation mutant of SP0148 comprising or lacking one or more of said domains and motifs.

In some embodiments, vaccines or pharmaceutical compositions comprising an *S. pneumoniae* polypeptide include a polypeptide containing at least 20 consecutive amino acid residues selected from SP0148. The polypeptide may also be a variant of the at least 20 residue fragment. In certain embodiments, the polypeptide includes no more than 250, 275, 200, 175, 150, 125, or 100 consecutive amino acids from SP0148.

Endogenous SP0148 comprises a putative signal sequence that may direct its secretion. In some embodiments, a variant of SP0148 that lacks the signal sequence (SEQ ID NO: 6) is used. The polypeptide of SEQ ID NO: 6 is encoded by the nucleic acid of SEQ ID NO: 27, although other nucleic acid sequences (including codon-optimized sequences) may be used. SEQ ID NO: 28 encodes the full length sequence of SP0148 used in the screens herein.

Variants of the amino acid sequence and nucleotide sequence of SP0148 may be found in U.S. Patent Application Publication No. 2005/0020813. U.S. Pat. Nos. 7,378,514 and 7,504,110, and European Patent Application No. EP1572868 and EP1855717.

Consensus sequences illustrating combinations of SP0148 sequences from different *S. pneumoniae* serotypes are provided as SEQ ID NOS: 18 and 19. Accordingly, in certain embodiments, the vaccine formulation comprises a polypeptide having an amino acid sequence comprising, or consisting of, either of SEQ ID NOS: 18-19, or an immunogenic fragment thereof (e.g., in place of a polypeptide having an amino acid sequence comprising one of SEQ ID NOS: 6 or 7).

4. SP1072 (SEQ ID NO: 8) and Variants Thereof

SP1072, also known as dnaG, is a DNA primase enzyme that catalyzes formation of an RNA primer which allows DNA polymerase to initiate DNA replication. A protein of 586 amino acids, SP1072 contains several conserved motifs. Beginning at the N-terminus, amino acids 2-96 form a zinc finger domain, the DNA primase catalytic core spans amino acids 122-250, and a highly conserved topoisomerase-primase (TORPIM) nucleotidyl transferase/hydrolase domain region extends from amino acid 258 to 330. In some embodiments, a vaccine or other composition comprises a truncation mutant of SP1072 comprising or lacking one or more of said domains and motifs.

In some embodiments, vaccines or pharmaceutical compositions comprising an *S. pneumoniae* polypeptide include a polypeptide containing at least 20 consecutive amino acid residues selected form SP1072. The polypeptide may also be a variant of the at least 20 residue fragment. In certain embodiments, the polypeptide includes no more than 550, 500, 450, 400, 350, 300, 250, 200, 150, or 100 consecutive amino acids from SP1072.

5. SP2108 (SEQ ID NO: 9) and Variants Thereof

The polypeptide SP2108 is 423 amino acids in length and is alternatively known as MalX, maltose/maltodextrin ABC transporter, or maltose/maltodextrin-binding protein. Much of the protein (amino acids 3-423) is classified as a MalE (Maltose-binding periplasmic) domain. In addition. SP2108 contains a signal sequence that directs its secretion. In some embodiments, a vaccine or other composition comprises a truncation mutant of SP2108 comprising one or more of said domains and motifs.

In some embodiments, the compositions and methods herein call for the use of an SP2108 variant that lacks the signal sequence. This variant is represented by polypeptide sequence SEQ ID NO: 10 and may be encoded by, for example, a nucleic acid according to SEQ ID NO: 29.

In some embodiments, vaccines or pharmaceutical compositions comprising an *S. pneumoniae* polypeptide include a polypeptide containing at least 20 consecutive amino acid residues selected from SP2108. The polypeptide may also be a variant of the at least 20 residue fragment. In certain embodiments, the polypeptide includes no more than 400, 350, 300, 250, 200, 150, or 100 consecutive amino acids from SP2108.

Consensus sequences illustrating combinations of SP2108 sequences from different serotypes are provided as SEQ ID NOS: 20 and 21. Thus, in certain embodiments, the vaccine formulation comprises a polypeptide having an amino acid sequence comprising, or consisting of, either of SEQ ID NOS: 20-21, or an immunogenic fragment thereof (e.g., in place of a polypeptide having an amino acid sequence comprising one of SEQ ID NOS: 9 or 10).

6. SP0641 (SEQ ID NO: 12) and Variants Thereof

At 2144 amino acids in length, SP0641 is also known as PrtA, a cell wall-associated serine protease. Full-length SP0641 contains a number of conserved motifs: the PA_2 motif, extending between amino acids 485 and 597, which may form a protein binding surface; the Fn3-like domain (amino acids 800-939); and two predicted catalytic domains of the SS8 C5a type located at amino acids 226-449 and 639-777. In some embodiments, a vaccine or other composition comprises a truncation mutant of SP0641 comprising or lacking one or more of said domains and motifs.

In some embodiments, vaccines or pharmaceutical compositions comprising an *S. pneumoniae* polypeptide include a polypeptide containing at least 20 consecutive amino acid residues selected from SP0641. The polypeptide may also be a variant of the at least 20 residue fragment. In certain embodiments, the polypeptide includes no more than 1000, 900, 800, 700, 600, 500, 400, 300, 200, or 100 consecutive amino acids from SP0641.

Certain other truncation mutants of SP0641 may also be used. For instance, the polypeptide designated SP0641N (SEQ ID NO: 13) consists of 661 amino acids corresponding to amino acids 24-684 near the N-terminus of SP0641. Roughly adjacent to SP0641N (and corresponding to amino acids 686-1333 of SP0641) lies the 648 residue region captured by the truncation variant SP0641M (SEQ ID NO: 11).

Variants of SP0641 are disclosed in, for example, U.S. Pat. Nos. 7,338,786, 6,573,082, and 7,132,107, as well as International Application WO00/06738.

SEQ ID NOS: 30 and 31 display the DNA sequences of SP0641M and SP0641N, respectively, although due to degeneracy in the genetic code, other DNA sequences (including codon-optimized sequences) could encode SP0641.

Polypeptides homologous to the polypeptides of Tables 1 and 2 (for example, SP0024, 0882, 0882N, 0148 with or without a signal sequence, 1072, SP1028 with or without a signal sequence, SP0641, SP0641M, or SP0641N) may also be used in the compositions and methods disclosed herein. Individual strains of *S. pneumoniae* contain numerous mutations relative to each other, and some of these result different protein sequences between the different strains. One of skill in the art may readily substitute an amino acid sequence, or a portion thereof, with the homologous amino acid sequence from a different *S. pneumoniae* strain. In certain aspects, this application provides immunogenic polypeptides with at least 90%, 95%, 97%, 98%, 99%, or 99.5% identity to the polypeptides of Tables 1 and 2 or an immunogenic fragment thereof. Serotypic variation may be used to design such variants of the polypeptides of Tables 1 and 2.

In some embodiments, the vaccine compositions herein comprise a fragment of a protein of Table 1 or 2 (for example, fragments of SP0024, SP0882, SP0882N, 0SP148 with or without a signal sequence, SP1072, SP1028 with or without a signal sequence, SP0641, SP0641M, or SP0641N). In some embodiments, this application provides truncation mutants that are close in size to the polypeptide of Table 1 or 2 (for example, one of SEQ ID NOS: 1-13). For example, they may lack at most one, two three, four, five, ten, or twenty amino acids from one or both termini. Internal deletions, e.g., of 1-10, 11-20, 21-30, or 31-40 amino acids, are also contemplated.

In certain embodiments the vaccine formulation comprises one or more polypeptides having an amino acid sequence comprising, or consisting of, any of SEQ ID NOS: 14-21. In certain embodiments, the fragment is a truncated fragment of any of SEQ ID NOS: 14-21 wherein from 1-5, 1-10, or 1-20 amino acid residues are removed from the N-terminus, C-terminus, or both. In certain embodiments, the fragment is a truncated fragment of any of SEQ ID NOS: 14-21 wherein from 1-10 amino acid residues are removed from the N-terminus, C-terminus, or both. For instance, 10 amino acid residues may be removed from each of the N-terminus and C-terminus resulting in a protein with 20 amino acid residues removed.

In addition to those nucleic acids and polypeptides described in Table 1 above, this application also provides immunogenic compositions that include one or more of the polypeptides or genes listed in Table 1 and/or Table 2, or variants or fragments thereof as described herein. The DNA and protein sequence of each gene and protein may be found by searching for the Locus Tag in the publicly available database, Entrez Gene, as described above.

TABLE 2

Immunogenic proteins identified in human and mouse screens

| Locus tag name | Protein accession number | DNA accession number (from Mar. 30, 2010) |
|---|---|---|
| SP1574 | AAK75660.1 | NC_003028.3\|:c1481367-1480609 |
| SP1655 | AAK75734.1 | NC_003028.3\|:c1557922-1557230 |
| SP2106 | AAK76165.1 | NC_003028.3\|:c2018657-2016399 |
| SP1473 | AAK75567.1 | NC_003028.3\|:c1386534-1386277 |
| SP0605 | AAK74757.1 | NC_003028.3\|:571604-572485 |
| SP1177 | AAK75286.1 | NC_003028.3\|:c1115580-1115317 |
| SP0335 | AAK74510.1 | NC_003028.3\|:306559-306876 |
| SP0906 | AAK75031.1 | NC_003028.3\|:c859160-859029 |
| SP1828 | AAK75901.1 | NC_003028.3\|:c1740010-1739000 |
| SP2157 | AAK76211.1 | NC_003028.3\|:c2072146-2070995 |
| SP1229 | AAK75335.1 | NC_003028.3\|:c1163388-1161718 |
| SP1128 | AAK75238.1 | NC_003028.3\|:1061773-1063077 |
| SP1836 | AAK75909.1 | NC_003028.3\|:1746104-1746280 |
| SP1865 | AAK75937.1 | NC_003028.3\|:c1772987-1771923 |
| SP0904 | AAK75029.1 | NC_003028.3\|:c858126-857311 |
| SP0765 | AAK74903.1 | NC_003028.3\|:724170-725207 |
| SP1634 | AAK75714.1 | NC_003028.3\|:1534348-1535421 |
| SP0418 | AAK74581.1 | NC_003028.3\|:396692-396916 |
| SP1923 | AAK75991.1 | NC_003028.3\|:c1833311-1831896 |
| SP1313 | AAK75991.1 | NC_003028.3\|:c1833311-1831896 |
| SP0775 | AAK74913.1 | NC_003028.3\|:731798-732070 |
| SP0314 | AAK74491.1 | NC_003028.3\|:287483-290683 |
| SP0912 | AAK75037.1 | NC_003028.3\|:864707-865465 |
| SP0159 | AAK74341.1 | NC_003028.3\|:c157554-156292 |
| SP0910 | AAK75035.1 | NC_003028.3\|:863462-863734 |
| SP2148 | AAK76205.1 | NC_003028.3\|:2062144-2063373 |
| SP1412 | AAK75510.1 | NC_003028.3\|:c1332393-1331605 |
| SP0372 | AAK74539.1 | NC_003028.3\|:350268-350597 |
| SP1304 | AAK75407.1 | NC_003028.3\|:c1232491-1232390 |
| SP2002 | AAK76069.1 | NC_003028.3\|:c1906183-1905446 |
| SP0612 | AAK74764.1 | NC_003028.3\|:579708-579806 |
| SP1988 | AAK76055.1 | NC_003028.3\|:c1892598-1890565 |
| SP0484 | AAK74643.1 | NC_003028.3\|:465572-466402 |
| SP0847 | AAK74978.1 | NC_003028.3\|:794144-795202 |
| SP1527 | AAK75616.1 | NC_003028.3\|:c1439494-1437536 |
| SP0542 | AAK74699.1 | NC_003028.3\|:515940-516059 |
| SP0441 | AAK74602.1 | NC_003028.3\|:414869-415057 |
| SP0350 | AAK74523.1 | NC_003028.3\|:323990-324625 |
| SP0014 | AAK74207.1 | NC_003028.3\|:14450-14929 |
| SP1965 | AAK76032.1 | NC_003028.3\|:c1873279-1873073 |
| SP0117 | AAK74303.1 | NC_003028.3\|:118423-120657 |
| SP0981 | AAK75102.1 | NC_003028.3\|:927115-928056 |
| SP2229 | AAK76277.1 | NC_003028.3\|:c2148627-2147602 |
| SP2136 | AAK76194.1 | NC_003028.3\|:c2048521-2046656 |
| SP1179 | AAK75288.1 | NC_003028.3\|:1116230-1118389 |
| SP1174 | AAK75283.1 | NC_003028.3\|:c110717-1108258 |
| SP2216 | AAK76264.1 | NC_003028.3\|:c2136445-2135267 |

TABLE 2-continued

Immunogenic proteins identified in human and mouse screens

| Locus tag name | Protein accession number | DNA accession number (from Mar. 30, 2010) |
|---|---|---|
| SP1393 | AAK75491.1 | NC_003028.3\|:1316756-1318027 |
| SP0641.1 | Amino acids 28-1006 of AAK74791.1 (which is full-length SP0641) | Nucleotides 603976-606910 of NC_003028.3 |
| SP1384 | AAK75482.1 | NC_003028.3\|:c1309464-1308967 |
| SP2032 | AAK76097.1 | NC_003028.3\|:c1939994-1938321 |

Typically, the polypeptides present in compounds of the invention are immunogenic, either alone or as a variant, which includes polypeptides fused to another polypeptide or mixed with or complexed to an adjuvant. Variants also include sequences with less than 100% sequence identity, as described herein. In certain embodiments, an antigen of Table 1 or 2 is provided as a full length polypeptide. In addition, one may use fragments, precursors and analogs that have an appropriate immunogenicity.

These polypeptides may be immunogenic in mammals, for example mice, guinea pigs, or humans. An immunogenic polypeptide is typically one capable of raising a significant immune response in an assay or in a subject. For instance, an immunogenic polypeptide may increase the amount of IL-17 produced by T cells. The IL-17 assay described in Examples 1-4 is an example of an assay that may be used to identify an immunogenic polypeptide. Alternatively, an immunogenic polypeptide may (i) induce production of antibodies, e.g., neutralizing antibodies, that bind to the polypeptide (ii) induce $T_H1$ immunity. (iii) activate the CD8+ CTL response, for example by increasing CD8+ T cells and/or increasing localization of CD8+ T cells to the site of infection or reinfection, (iv) induce $T_H17$ immunity, and/or (v) activate innate immunity. In some embodiments, an immunogenic polypeptide causes the production of a detectable amount of antibody specific to that antigen.

In certain embodiments, polypeptides have less than 20%, 30%, 40%, 50%, 60% or 70% identity to human autoantigens and/or gut commensal bacteria (e.g., certain *Bacteroides, Clostridium, Fusobacterium, Eubacterium, Ruminococcus, Peptococcus, Peptostreptococcus, Bifidobacterium, Escherichia* and *Lactobacillus* species). Examples of human autoantigens include insulin, proliferating cell nuclear antigen, cytochrome P450, and myelin basic protein.

The present disclosure provides, for example, a vaccine formulation comprising a pharmaceutically acceptable carrier and one or more polypeptides having an amino acid sequence comprising any of SEQ ID NOS: 1-11 or an immunogenic fragment thereof, and optionally further comprising a polypeptide having an amino acid sequence comprising either of SEQ ID NOS: 12 or 13 or an immunogenic fragment thereof. In certain embodiments, the vaccine formulation comprises at least two different polypeptides having an amino acid sequence comprising any of SEQ ID NOS: 1-13 or an immunogenic fragment thereof, wherein at least one of said polypeptides has an amino acid sequence comprising one of SEQ ID NOS: 1-10 or an immunogenic fragment thereof. Here, the term "different" signifies that each of said two peptides originates from a different sequence selected from SEQ ID NOS: 1-13.

The vaccine formulation may also comprise one or more polypeptides having an amino acid sequence consisting of any of SEQ ID NOS: 1-11.

In some embodiments, the vaccine formulation comprises at least two polypeptides, each polypeptide belonging to a different group of (i)-(vi): (i) SEQ ID NO: 1 or an immunogenic fragment thereof. (ii) one of SEQ ID NOS: 2-5 or an immunogenic fragment thereof, (iii) one of SEQ ID NOS: 6-7 or an immunogenic fragment thereof, (iv) SEQ ID NO: 8 or an immunogenic fragment thereof, (v) one of SEQ ID NOS: 9-10 or an immunogenic fragment thereof, and (vi) one of SEQ ID NO: 11-13 or an immunogenic fragment thereof. Examples of such combinations are listed below:

SEQ ID NO: 1 and SEQ ID NO: 2
SEQ ID NO: 1 and SEQ ID NO: 3
SEQ ID NO: 1 and SEQ ID NO: 4
SEQ ID NO: 1 and SEQ ID NO: 5
SEQ ID NO: 1 and SEQ ID NO: 6
SEQ ID NO: 1 and SEQ ID NO: 7
SEQ ID NO: 1 and SEQ ID NO: 8
SEQ ID NO: 1 and SEQ ID NO: 9
SEQ ID NO: 1 and SEQ ID NO: 10
SEQ ID NO: 1 and SEQ ID NO: 11
SEQ ID NO: 1 and SEQ ID NO: 12
SEQ ID NO: 1 and SEQ ID NO: 13
SEQ ID NO: 2 and SEQ ID NO: 6
SEQ ID NO: 2 and SEQ ID NO: 7
SEQ ID NO: 2 and SEQ ID NO: 8
SEQ ID NO: 2 and SEQ ID NO: 9
SEQ ID NO: 2 and SEQ ID NO: 10
SEQ ID NO: 2 and SEQ ID NO: 11
SEQ ID NO: 2 and SEQ ID NO: 12
SEQ ID NO: 2 and SEQ ID NO: 13
SEQ ID NO: 3 and SEQ ID NO: 6
SEQ ID NO: 3 and SEQ ID NO: 7
SEQ ID NO: 3 and SEQ ID NO: 8
SEQ ID NO: 3 and SEQ ID NO: 9
SEQ ID NO: 3 and SEQ ID NO: 10
SEQ ID NO: 3 and SEQ ID NO: 11
SEQ ID NO: 3 and SEQ ID NO: 12
SEQ ID NO: 3 and SEQ ID NO: 13
SEQ ID NO: 4 and SEQ ID NO: 6
SEQ ID NO: 4 and SEQ ID NO: 7
SEQ ID NO: 4 and SEQ ID NO: 8
SEQ ID NO: 4 and SEQ ID NO: 9
SEQ ID NO: 4 and SEQ ID NO: 10
SEQ ID NO: 4 and SEQ ID NO: 11
SEQ ID NO: 4 and SEQ ID NO: 12
SEQ ID NO: 4 and SEQ ID NO: 13
SEQ ID NO: 5 and SEQ ID NO: 6
SEQ ID NO: 5 and SEQ ID NO: 7
SEQ ID NO: 5 and SEQ ID NO: 8
SEQ ID NO: 5 and SEQ ID NO: 9
SEQ ID NO: 5 and SEQ ID NO: 10
SEQ ID NO: 5 and SEQ ID NO: 11
SEQ ID NO: 5 and SEQ ID NO: 12
SEQ ID NO: 5 and SEQ ID NO: 13
SEQ ID NO: 6 and SEQ ID NO: 8
SEQ ID NO: 6 and SEQ ID NO: 9
SEQ ID NO: 6 and SEQ ID NO: 10
SEQ ID NO: 6 and SEQ ID NO: 11
SEQ ID NO: 6 and SEQ ID NO: 12
SEQ ID NO: 6 and SEQ ID NO: 13
SEQ ID NO: 7 and SEQ ID NO: 8
SEQ ID NO: 7 and SEQ ID NO: 9
SEQ ID NO: 7 and SEQ ID NO: 10
SEQ ID NO: 7 and SEQ ID NO: 11
SEQ ID NO: 7 and SEQ ID NO: 12
SEQ ID NO: 7 and SEQ ID NO: 13
SEQ ID NO: 8 and SEQ ID NO: 9

SEQ ID NO: 8 and SEQ ID NO: 10
SEQ ID NO: 8 and SEQ ID NO: 11
SEQ ID NO: 8 and SEQ ID NO: 12
SEQ ID NO: 8 and SEQ ID NO: 13
SEQ ID NO: 9 and SEQ ID NO: 11
SEQ ID NO: 9 and SEQ ID NO: 12
SEQ ID NO: 9 and SEQ ID NO: 13
SEQ ID NO: 10 and SEQ ID NO: 11
SEQ ID NO: 10 and SEQ ID NO: 12
SEQ ID NO: 10 and SEQ ID NO: 13

In certain embodiments, the vaccine formulation comprises at least three different polypeptides having an amino acid sequence comprising any of SEQ ID NOS: 1-13 or an immunogenic fragment thereof, wherein at least one of said polypeptides has an amino acid sequence comprising one of SEQ ID NOS: 1-10. In certain such embodiments, the vaccine formulation comprises at least three polypeptides, each polypeptide belonging to a different group of (i)-(vi): (i) SEQ ID NO: 1 or an immunogenic fragment thereof. (ii) one of SEQ ID NOS: 2-5 or an immunogenic fragment thereof, (iii) one of SEQ ID NOS: 6-7 or an immunogenic fragment thereof, (iv) SEQ ID NO: 8 or an immunogenic fragment thereof, (v) one of SEQ ID NOS: 9-10 or an immunogenic fragment thereof, and (vi) one of SEQ ID NO: 11-13 or an immunogenic fragment thereof. Examples of such combinations are listed below:

SEQ ID NO: 1, SEQ ID NO: 2, and SEQ ID NO: 6
SEQ ID NO: 1, SEQ ID NO: 2, and SEQ ID NO: 7
SEQ ID NO: 1, SEQ ID NO: 2, and SEQ ID NO: 8
SEQ ID NO: 1, SEQ ID NO: 2, and SEQ ID NO: 9
SEQ ID NO: 1, SEQ ID NO: 2, and SEQ ID NO: 10
SEQ ID NO: 1, SEQ ID NO: 2, and SEQ ID NO: 11
SEQ ID NO: 1, SEQ ID NO: 2, and SEQ ID NO: 12
SEQ ID NO: 1, SEQ ID NO: 2, and SEQ ID NO: 13
SEQ ID NO: 1, SEQ ID NO: 3, and SEQ ID NO: 6
SEQ ID NO: 1, SEQ ID NO: 3, and SEQ ID NO: 7
SEQ ID NO: 1, SEQ ID NO: 3, and SEQ ID NO: 8
SEQ ID NO: 1, SEQ ID NO: 3, and SEQ ID NO: 9
SEQ ID NO: 1, SEQ ID NO: 3, and SEQ ID NO: 10
SEQ ID NO: 1, SEQ ID NO: 3, and SEQ ID NO: 11
SEQ ID NO: 1, SEQ ID NO: 3, and SEQ ID NO: 12
SEQ ID NO: 1, SEQ ID NO: 3, and SEQ ID NO: 13
SEQ ID NO: 1, SEQ ID NO: 4; and SEQ ID NO: 6
SEQ ID NO: 1, SEQ ID NO: 4; and SEQ ID NO: 7
SEQ ID NO: 1, SEQ ID NO: 4; and SEQ ID NO: 8
SEQ ID NO: 1, SEQ ID NO: 4; and SEQ ID NO: 9
SEQ ID NO: 1, SEQ ID NO: 4; and SEQ ID NO: 10
SEQ ID NO: 1, SEQ ID NO: 4; and SEQ ID NO: 11
SEQ ID NO: 1, SEQ ID NO: 4; and SEQ ID NO: 12
SEQ ID NO: 1, SEQ ID NO: 4; and SEQ ID NO: 13
SEQ ID NO: 1, SEQ ID NO: 5; and SEQ ID NO: 6
SEQ ID NO: 1, SEQ ID NO: 5; and SEQ ID NO: 7
SEQ ID NO: 1, SEQ ID NO: 5; and SEQ ID NO: 8
SEQ ID NO: 1, SEQ ID NO: 5; and SEQ ID NO: 9
SEQ ID NO: 1, SEQ ID NO: 5; and SEQ ID NO: 10
SEQ ID NO: 1, SEQ ID NO: 5; and SEQ ID NO: 11
SEQ ID NO: 1, SEQ ID NO: 5; and SEQ ID NO: 12
SEQ ID NO: 1, SEQ ID NO: 5; and SEQ ID NO: 13
SEQ ID NO: 1, SEQ ID NO: 6; and SEQ ID NO: 8
SEQ ID NO: 1, SEQ ID NO: 6; and SEQ ID NO: 9
SEQ ID NO: 1, SEQ ID NO: 6; and SEQ ID NO: 10
SEQ ID NO: 1, SEQ ID NO: 6; and SEQ ID NO: 11
SEQ ID NO: 1, SEQ ID NO: 6; and SEQ ID NO: 12
SEQ ID NO: 1, SEQ ID NO: 6; and SEQ ID NO: 13
SEQ ID NO: 1, SEQ ID NO: 7; and SEQ ID NO: 8
SEQ ID NO: 1, SEQ ID NO: 7; and SEQ ID NO: 9
SEQ ID NO: 1, SEQ ID NO: 7; and SEQ ID NO: 10
SEQ ID NO: 1, SEQ ID NO: 7; and SEQ ID NO: 11
SEQ ID NO: 1, SEQ ID NO: 7; and SEQ ID NO: 12
SEQ ID NO: 1, SEQ ID NO: 7; and SEQ ID NO: 13
SEQ ID NO: 1, SEQ ID NO: 8; and SEQ ID NO: 9
SEQ ID NO: 1, SEQ ID NO: 8; and SEQ ID NO: 10
SEQ ID NO: 1, SEQ ID NO: 8; and SEQ ID NO: 11
SEQ ID NO: 1, SEQ ID NO: 8; and SEQ ID NO: 12
SEQ ID NO: 1, SEQ ID NO: 8; and SEQ ID NO: 13
SEQ ID NO: 1, SEQ ID NO: 9; and SEQ ID NO: 11
SEQ ID NO: 1, SEQ ID NO: 9; and SEQ ID NO: 12
SEQ ID NO: 1, SEQ ID NO: 9; and SEQ ID NO: 13
SEQ ID NO: 1, SEQ ID NO: 10; and SEQ ID NO: 11
SEQ ID NO: 1, SEQ ID NO: 10; and SEQ ID NO: 12
SEQ ID NO: 1, SEQ ID NO: 10; and SEQ ID NO: 13
SEQ ID NO: 2, SEQ ID NO: 6; and SEQ ID NO: 8
SEQ ID NO: 2, SEQ ID NO: 6; and SEQ ID NO: 9
SEQ ID NO: 2, SEQ ID NO: 6; and SEQ ID NO: 10
SEQ ID NO: 2, SEQ ID NO: 6; and SEQ ID NO: 11
SEQ ID NO: 2, SEQ ID NO: 6; and SEQ ID NO: 12
SEQ ID NO: 2, SEQ ID NO: 6; and SEQ ID NO: 13
SEQ ID NO: 2, SEQ ID NO: 7; and SEQ ID NO: 8
SEQ ID NO: 2, SEQ ID NO: 7; and SEQ ID NO: 9
SEQ ID NO: 2, SEQ ID NO: 7; and SEQ ID NO: 10
SEQ ID NO: 2, SEQ ID NO: 7; and SEQ ID NO: 11
SEQ ID NO: 2, SEQ ID NO: 7; and SEQ ID NO: 12
SEQ ID NO: 2, SEQ ID NO: 7; and SEQ ID NO: 13
SEQ ID NO: 2, SEQ ID NO: 8; and SEQ ID NO: 9
SEQ ID NO: 2, SEQ ID NO: 8; and SEQ ID NO: 10
SEQ ID NO: 2, SEQ ID NO: 8; and SEQ ID NO: 11
SEQ ID NO: 2, SEQ ID NO: 8; and SEQ ID NO: 12
SEQ ID NO: 2, SEQ ID NO: 8; and SEQ ID NO: 13
SEQ ID NO: 2, SEQ ID NO: 9; and SEQ ID NO: 11
SEQ ID NO: 2, SEQ ID NO: 9; and SEQ ID NO: 12
SEQ ID NO: 2, SEQ ID NO: 9; and SEQ ID NO: 13
SEQ ID NO: 2, SEQ ID NO: 10; and SEQ ID NO: 11
SEQ ID NO: 2, SEQ ID NO: 10; and SEQ ID NO: 12
SEQ ID NO: 2, SEQ ID NO: 10; and SEQ ID NO: 13
SEQ ID NO: 3, SEQ ID NO: 6; and SEQ ID NO: 8
SEQ ID NO: 3, SEQ ID NO: 6; and SEQ ID NO: 9
SEQ ID NO: 3, SEQ ID NO: 6; and SEQ ID NO: 10
SEQ ID NO: 3, SEQ ID NO: 6; and SEQ ID NO: 11
SEQ ID NO: 3, SEQ ID NO: 6; and SEQ ID NO: 12
SEQ ID NO: 3, SEQ ID NO: 6; and SEQ ID NO: 13
SEQ ID NO: 3, SEQ ID NO: 7; and SEQ ID NO: 8
SEQ ID NO: 3, SEQ ID NO: 7; and SEQ ID NO: 9
SEQ ID NO: 3, SEQ ID NO: 7; and SEQ ID NO: 10
SEQ ID NO: 3, SEQ ID NO: 7; and SEQ ID NO: 11
SEQ ID NO: 3, SEQ ID NO: 7; and SEQ ID NO: 12
SEQ ID NO: 3, SEQ ID NO: 7; and SEQ ID NO: 13
SEQ ID NO: 3, SEQ ID NO: 8; and SEQ ID NO: 9
SEQ ID NO: 3, SEQ ID NO: 8; and SEQ ID NO: 10
SEQ ID NO: 3, SEQ ID NO: 8; and SEQ ID NO: 11
SEQ ID NO: 3, SEQ ID NO: 8; and SEQ ID NO: 12
SEQ ID NO: 3, SEQ ID NO: 8; and SEQ ID NO: 13
SEQ ID NO: 3, SEQ ID NO: 9; and SEQ ID NO: 11
SEQ ID NO: 3, SEQ ID NO: 9; and SEQ ID NO: 12
SEQ ID NO: 3, SEQ ID NO: 9; and SEQ ID NO: 13
SEQ ID NO: 3, SEQ ID NO: 10; and SEQ ID NO: 11
SEQ ID NO: 3, SEQ ID NO: 10; and SEQ ID NO: 12
SEQ ID NO: 3, SEQ ID NO: 10; and SEQ ID NO: 13
SEQ ID NO: 4, SEQ ID NO: 6; and SEQ ID NO: 8
SEQ ID NO: 4, SEQ ID NO: 6; and SEQ ID NO: 9
SEQ ID NO: 4, SEQ ID NO: 6; and SEQ ID NO: 10
SEQ ID NO: 4, SEQ ID NO: 6; and SEQ ID NO: 11
SEQ ID NO: 4, SEQ ID NO: 6; and SEQ ID NO: 12
SEQ ID NO: 4, SEQ ID NO: 6; and SEQ ID NO: 13
SEQ ID NO: 4, SEQ ID NO: 7; and SEQ ID NO: 8

SEQ ID NO: 4, SEQ ID NO: 7; and SEQ ID NO: 9
SEQ ID NO: 4, SEQ ID NO: 7; and SEQ ID NO: 10
SEQ ID NO: 4, SEQ ID NO: 7; and SEQ ID NO: 11
SEQ ID NO: 4, SEQ ID NO: 7; and SEQ ID NO: 12
SEQ ID NO: 4, SEQ ID NO: 7; and SEQ ID NO: 13
SEQ ID NO: 4, SEQ ID NO: 8; and SEQ ID NO: 9
SEQ ID NO: 4, SEQ ID NO: 8; and SEQ ID NO: 10
SEQ ID NO: 4, SEQ ID NO: 8; and SEQ ID NO: 11
SEQ ID NO: 4, SEQ ID NO: 8; and SEQ ID NO: 12
SEQ ID NO: 4, SEQ ID NO: 8; and SEQ ID NO: 13
SEQ ID NO: 4, SEQ ID NO: 9; and SEQ ID NO: 11
SEQ ID NO: 4, SEQ ID NO: 9; and SEQ ID NO: 12
SEQ ID NO: 4, SEQ ID NO: 9; and SEQ ID NO: 13
SEQ ID NO: 4, SEQ ID NO: 10; and SEQ ID NO: 11
SEQ ID NO: 4, SEQ ID NO: 10; and SEQ ID NO: 12
SEQ ID NO: 4, SEQ ID NO: 10; and SEQ ID NO: 13
SEQ ID NO: 5, SEQ ID NO: 6; and SEQ ID NO: 8
SEQ ID NO: 5, SEQ ID NO: 6; and SEQ ID NO: 9
SEQ ID NO: 5, SEQ ID NO: 6; and SEQ ID NO: 10
SEQ ID NO: 5, SEQ ID NO: 6; and SEQ ID NO: 11
SEQ ID NO: 5, SEQ ID NO: 6; and SEQ ID NO: 12
SEQ ID NO: 5, SEQ ID NO: 6; and SEQ ID NO: 13
SEQ ID NO: 5, SEQ ID NO: 7; and SEQ ID NO: 8
SEQ ID NO: 5, SEQ ID NO: 7; and SEQ ID NO: 9
SEQ ID NO: 5, SEQ ID NO: 7; and SEQ ID NO: 10
SEQ ID NO: 5, SEQ ID NO: 7; and SEQ ID NO: 11
SEQ ID NO: 5, SEQ ID NO: 7; and SEQ ID NO: 12
SEQ ID NO: 5, SEQ ID NO: 7; and SEQ ID NO: 13
SEQ ID NO: 5, SEQ ID NO: 8; and SEQ ID NO: 9
SEQ ID NO: 5, SEQ ID NO: 8; and SEQ ID NO: 10
SEQ ID NO: 5, SEQ ID NO: 8; and SEQ ID NO: 11
SEQ ID NO: 5, SEQ ID NO: 8; and SEQ ID NO: 12
SEQ ID NO: 5, SEQ ID NO: 8; and SEQ ID NO: 13
SEQ ID NO: 5, SEQ ID NO: 9; and SEQ ID NO: 11
SEQ ID NO: 5, SEQ ID NO: 9; and SEQ ID NO: 12
SEQ ID NO: 5, SEQ ID NO: 9; and SEQ ID NO: 13
SEQ ID NO: 5, SEQ ID NO: 10; and SEQ ID NO: 11
SEQ ID NO: 5, SEQ ID NO: 10; and SEQ ID NO: 12
SEQ ID NO: 5, SEQ ID NO: 10; and SEQ ID NO: 13
SEQ ID NO: 6, SEQ ID NO: 8; and SEQ ID NO: 9
SEQ ID NO: 6, SEQ ID NO: 8; and SEQ ID NO: 10
SEQ ID NO: 6, SEQ ID NO: 8; and SEQ ID NO: 11
SEQ ID NO: 6, SEQ ID NO: 8; and SEQ ID NO: 12
SEQ ID NO: 6, SEQ ID NO: 8; and SEQ ID NO: 13
SEQ ID NO: 6, SEQ ID NO: 9; and SEQ ID NO: 11
SEQ ID NO: 6, SEQ ID NO: 9; and SEQ ID NO: 12
SEQ ID NO: 6, SEQ ID NO: 9; and SEQ ID NO: 13
SEQ ID NO: 6, SEQ ID NO: 10; and SEQ ID NO: 11
SEQ ID NO: 6, SEQ ID NO: 10; and SEQ ID NO: 12
SEQ ID NO: 6, SEQ ID NO: 10; and SEQ ID NO: 13
SEQ ID NO: 7, SEQ ID NO: 8; and SEQ ID NO: 9
SEQ ID NO: 7, SEQ ID NO: 8; and SEQ ID NO: 10
SEQ ID NO: 7, SEQ ID NO: 8; and SEQ ID NO: 11
SEQ ID NO: 7, SEQ ID NO: 8; and SEQ ID NO: 12
SEQ ID NO: 7, SEQ ID NO: 8; and SEQ ID NO: 13
SEQ ID NO: 7, SEQ ID NO: 9; and SEQ ID NO: 11
SEQ ID NO: 7, SEQ ID NO: 9; and SEQ ID NO: 12
SEQ ID NO: 7, SEQ ID NO: 9; and SEQ ID NO: 13
SEQ ID NO: 7, SEQ ID NO: 10; and SEQ ID NO: 11
SEQ ID NO: 7, SEQ ID NO: 10; and SEQ ID NO: 12
SEQ ID NO: 7, SEQ ID NO: 10; and SEQ ID NO: 13
SEQ ID NO: 8, SEQ ID NO: 9; and SEQ ID NO: 11
SEQ ID NO: 8, SEQ ID NO: 9; and SEQ ID NO: 12
SEQ ID NO: 8, SEQ ID NO: 9; and SEQ ID NO: 13
SEQ ID NO: 8, SEQ ID NO: 10; and SEQ ID NO: 11
SEQ ID NO: 8, SEQ ID NO: 10; and SEQ ID NO: 12
SEQ ID NO: 8, SEQ ID NO: 10; and SEQ ID NO: 13

In some embodiments, the vaccine formulation comprises at least two different polypeptides having an amino acid sequence comprising any of SEQ ID NOS: 14-21 or an immunogenic fragment thereof. In certain such embodiments, the vaccine formulation comprises at least two polypeptides, each polypeptide belonging to a different group of (i)-(iii): (i) one of SEQ ID NOS: 14-17 or an immunogenic fragment thereof, (ii) one of SEQ ID NOS: 18-19 or an immunogenic fragment thereof; and (iii) one of SEQ ID NOS: 20-21 or an immunogenic fragment thereof. Examples of such combinations are listed below:
SEQ ID NO: 14 and SEQ ID NO: 18
SEQ ID NO: 14 and SEQ ID NO: 19
SEQ ID NO: 14 and SEQ ID NO: 20
SEQ ID NO: 14 and SEQ ID NO: 21
SEQ ID NO: 15 and SEQ ID NO: 18
SEQ ID NO: 15 and SEQ ID NO: 19
SEQ ID NO: 15 and SEQ ID NO: 20
SEQ ID NO: 15 and SEQ ID NO: 21
SEQ ID NO: 16 and SEQ ID NO: 18
SEQ ID NO: 16 and SEQ ID NO: 19
SEQ ID NO: 16 and SEQ ID NO: 20
SEQ ID NO: 16 and SEQ ID NO: 21
SEQ ID NO: 17 and SEQ ID NO: 18
SEQ ID NO: 17 and SEQ ID NO: 19
SEQ ID NO: 17 and SEQ ID NO: 20
SEQ ID NO: 17 and SEQ ID NO: 21
SEQ ID NO: 18 and SEQ ID NO: 20
SEQ ID NO: 18 and SEQ ID NO: 21
SEQ ID NO: 19 and SEQ ID NO: 20
SEQ ID NO: 19 and SEQ ID NO: 21

In some aspects, a vaccine formulation comprising one or more of SEQ ID NOS: 14-21 further comprises a polypeptide having an amino acid sequence comprising any of SEQ ID NOS: 1-13.

In certain embodiments, the vaccine formulation comprises at least three different polypeptides having an amino acid sequence comprising any of SEQ ID NOS: 14-21 or an immunogenic fragment thereof. In certain such embodiments, the vaccine formulation comprises three of (i)-(iii): (i) one of SEQ ID NOS: 14-17 or an immunogenic fragment thereof, (ii) one of SEQ ID NOS: 18-19 or an immunogenic fragment thereof; and (iii) one of SEQ ID NOS: 20-21 or an immunogenic fragment thereof. Examples of such combinations are listed below:
SEQ ID NO: 14, SEQ ID NO: 18, and SEQ ID NO: 20
SEQ ID NO: 14, SEQ ID NO: 18, and SEQ ID NO: 21
SEQ ID NO: 14, SEQ ID NO: 19, and SEQ ID NO: 20
SEQ ID NO: 14, SEQ ID NO: 19, and SEQ ID NO: 21
SEQ ID NO: 15, SEQ ID NO: 18, and SEQ ID NO: 20
SEQ ID NO: 15, SEQ ID NO: 18, and SEQ ID NO: 21
SEQ ID NO: 15, SEQ ID NO: 19, and SEQ ID NO: 20
SEQ ID NO: 15, SEQ ID NO: 19, and SEQ ID NO: 21
SEQ ID NO: 16, SEQ ID NO: 18, and SEQ ID NO: 20
SEQ ID NO: 16, SEQ ID NO: 18, and SEQ ID NO: 21
SEQ ID NO: 16, SEQ ID NO: 19, and SEQ ID NO: 20
SEQ ID NO: 16, SEQ ID NO: 19, and SEQ ID NO: 21
SEQ ID NO: 17, SEQ ID NO: 18, and SEQ ID NO: 20
SEQ ID NO: 17, SEQ ID NO: 18, and SEQ ID NO: 21
SEQ ID NO: 17, SEQ ID NO: 19, and SEQ ID NO: 20
SEQ ID NO: 17, SEQ ID NO: 19, and SEQ ID NO: 21

A polypeptide may comprise one or more immunogenic portions and one or more non-immunogenic portions. The immunogenic portions may be identified by various methods, including protein microarrays, ELISPOT/ELISA techniques, and/or specific assays on different deletion mutants (e.g., fragments) of the polypeptide in question. Immunogenic portions may also be identified by computer algorithms. Some such algorithms, like EpiMatrix (produced by EpiVax), use a computational matrix approach. Other computational tools for identifying antigenic epitopes include PEPVAC (Promiscuous EPitope-based VACcine, hosted by Dana Farber Cancer Institute on the world wide web at immunax.dfci.harvard.edu/PEPVAC), and MHCPred (which uses a partial least squares approach and is hosted by The Jenner Institute on the world wide web at www.jenner.ac.uk/MHCPred). An immunogenic fragment of a polypeptide described herein comprises at least one immunogenic portion, as measured experimentally or identified by algorithm. Peptides identified by the tools described above include the following:

| SP2108 Fragments (SEQ ID NOS 34-57, respectively, in order of appearance) | SP0148 Fragments (SEQ ID NOS 58-82, respectively, in order of appearance) | SP1634 Fragments (SEQ ID NOS 83-109, respectively, in order of appearance) | SP0882 Fragments (SEQ ID NOS 110-130, respectively, in order of appearance) | SP0314 Fragments (SEQ ID NOS 131-169, respectively, in order of appearance) |
|---|---|---|---|---|
| AIIDGPWKA | ALGLVAAGV | RLLDLAPQV | HLDNLVLKV | MLKDKIAFL |
| VMMAPYDRV | ELTGYEIEV | MLEIPAHQI | DLIAGRVHL | SLADYTYKV |
| SIAGINYAK | AVNNLSYTK | KNFFAHHPK | ILLPKDYEK | FLLGAFYL |
| VWDPAKNML | TYLPAEADI | KVILAGHSK | EYQDQIGCL | VLIDGLSQL |
| QPLPNISQM | RYNMAVNNL | SFDNLVSTL | YFHDGQNVF | ILASLGFLL |
| APYDRVGSL | DFQQIMVRL | YYDLPLNEL | NPDISRMIV | GLSQLLPVI |
| APAVIESLV | EHTDNPTIL | YFDLFFGTI | IPWSENLPD | FLLNHYMTV |
| FYYTYGLLA | APIAQNPNV | ALEYIHHLF | QFGGKGVEY | MLIPNVDRA |
| SKYAFAGE | LPSDQQPYV | LPLNELDIL | IGLEYQDQI | KLEEMAKQV |
| TEGAGNLI | YVYPLLAQG | IPQGSIIGM | VYFHDGQN | VLKRGVYTI |
| LADWTNFYY | QGLDNLKVI | DPELQKQFA | MEVVKPFI | KVIAGLLRK |
| SLVMYYNKD | KYLYAAPI | AVYTFDAPG | YLKMKEHKL | TLNYEHMNK |
| KEAGVKVTL | GELTGYEI | QSLTPEERE | KLSPDQRIF | NIGYFFFKK |
| KSTAVLGTV | NPNVLVVKK | AIYAASQI | RIFIYVGTE | KYTDVIEKF |
| GAKTDDTTK | KLSKQFFGD | LEIPAHQI | FIDETYRTK | KYDDSVSTI |
| SQKFVDFLV | GSPRFIYE | LLDLAPQVP | DTDRSYPVV | TFNQMIKEL |
| QAFKDAKVN | AVNNLSYTK | WQIEDKHFV | YIDSSLCYY | DYPETQSVF |
| AVIESLVMY | KIFDKIGVE | TLGRLTQLL | TQFIGLEYQ | TPRAINNTL |
| DAKTAANDA | MVRLSDGQF | LYFDLFFGT | KDTDRSYPV | APLLVNGEL |
| YGVATIPTL | YVYPLLAQG | SINDLASLK | LCYYHDLIA | YIDHTNVAY |
| KTAAIIDGP | VVQATTSAK | SINDLASLK | NVFNSKESF | KQNGDSYGY |
| KAYEKEAGV | TLEKLSKQF | YDLPLNEL | | FLLNHYMTV |
| AGNGAYVFG | VAAGVLAAC | QKVILAGHS | | FYLYNGDLS |
| AWVIPQAVK | LDNLKVIEL | GTDDSIIGW | | KSFAPLLV |
| | NMAVNNLSY | TYLSFDNLV | | DETVVRTV |
| | | FGTILDAGI | | YIDHTNVAY |
| | | NQITAVYTF | | MLKDKIAFL |
| | | | | KLRKIKTD |
| | | | | KLELFYETG |
| | | | | KIAFLGSNI |
| | | | | SVPRTSYLS |
| | | | | FGFGLSLFS |
| | | | | STIRSIEQV |
| | | | | FRKTTDNPF |
| | | | | TVVRTVRDS |
| | | | | STIRSIEQV |
| | | | | DGLSQLLPV |
| | | | | FGFGLSLFS |
| | | | | KLVDQGEGF |

| SP0024 Fragments (SEQ ID NOS 170-193, respectively, in order of appearance) | SP1072 Fragments (SEQ ID NOS 194-227, respectively, in order of appearance) | SP0641 Fragments (SEQ ID NOS 228-264, respectively, in order of appearance) |
|---|---|---|
| AIVTCMDSR | GIEVEKPLY | AAYAPNEVV |
| AQTFENEPF | AEAHLLYRM | AGDLRGKII |
| AYVALHGQL | ALLNQDNMR | DEIANEVWY |
| DDVIISGAI | APPERNYLY | DNYLIYGDL |
| FENEPFQEY | AQNSYIHIL | DQKEHPEKF |
| FMQANQAYV | AVASMGTAL | DSLTDRLKL |
| ISQQMGTR | AYLLTKTRI | EAKNKNKFV |
| KPKTRVAIV | DAAKFYHAI | EGQGRNRKL |
| LHGQLNLPL | DTALEELER | EIKGAGDLR |
| LHVAQALGL | EEYQGVPFI | EPIAEGQYF |
| LPLKPKTRV | EFLEKIAPL | EVSELKPHR |
| MGTREIVVL | EFQVLYDLL | GAFFDKSKI |
| MQLLIESPL | EHVEHLKRL | GDLKWDGLI |
| QANQAYVAL | ELSEVEMTR | GEVEKNLEV |
| QFMQANQAY | ESPLVLNDY | IHFESVEEM |

| | | |
|---|---|---|
| QLNLPLKPK | GEKTPSFNV | IMFIVGIFL |
| QQMGTREIV | GLCPFHGEK | IPGTLNKGI |
| REIVVLHHT | IGDMPVQIV | IRYQVFTFK |
| SPLIPDDVI | ITMPVTKQL | ISDKGGFNW |
| SRLHVAQAL | KALLNQDNM | IVSEEDFIL |
| TEDMIRSLV | KRLTKKLVL | KEIGVEEAI |
| VDVSDQDFL | LTKTRISPI | KIVVKDFAR |
| VSDQDFLPF | LVLVYDGDK | KKINFQPSL |
| VTEDMIRSL | MRAEAHLLY | KLKFVYIGK |
| | NGPEDLAYL | KVYYGNNYK |
| | QTEEVERAW | KYWQAIRAL |
| | SEIYLMEGF | LHIDNTRDF |
| | SPHQALYDM | MRFKKEDLK |
| | VDKQVIEEI | NESVVDNYL |
| | VEMTRNKAL | NEVWYAGAA |
| | VLYDLLGQY | NINDIVDGL |
| | VPFIEAVQI | QYLLKDNII |
| | WYQVLAQDL | SPRQQGAGL |
| | YLMEGFMDV | SRSKTLGGY |
| | | SSLKNTKVL |
| | | TAAVILAAY |
| | | WTELPAMGY |

Thus, in some aspects, this application provides an immunogenic fragment of an antigen described herein. The fragments, in some instances, are close in size to the full-length polypeptide or the polypeptide of Table 1 or 2. For example, they may lack at most one, two, three, four, five, ten, or twenty amino acids from one or both termini. In certain embodiments, the polypeptide is 100-500 amino acids in length, or 150-450, or 200-400, or 250-250 amino acids in length. In some embodiments, the polypeptide is 100-200, 150-250, 200-300, 250-350, 300-400, 350-450, or 400-500 amino acids in length. The fragments described above or sub-fragments thereof (e.g., fragments of 8-50, 8-30, or 8-20 amino acid residues) preferably have one of the biological activities described below, such as increasing the amount of IL-17 released by at least 1.5 fold or 2 fold or more (e.g., either as an absolute measure or relative to an immunologically inactive protein such as ovalbumin). A fragment may be used as the polypeptide in the vaccines described herein or may be fused to another protein, protein fragment or a polypeptide.

In some embodiments, the fragment is a truncated fragment of any of SEQ ID NOS: 1-13 having from 1-5, 1-10, or 1-20 amino acid residues removed from the N-terminus, C-terminus, or both. In some such embodiments, the same number of residues is removed from the N-terminus and the C-terminus, while in other embodiments, a different number of residues is removed from the N-terminus compared to the C-terminus.

In certain aspects, this application provides immunogenic polypeptides with at least 90%, 95%, 97%, 98%, 99%, or 99.5% identity to a polypeptide of Table 1 or 2. The present disclosure also provides a vaccine formulation comprising a pharmaceutically acceptable carrier and one or more polypeptides having an amino acid sequence comprising a sequence at least 90%, 95%, 98%, or 99% identical to any of SEQ ID NOS: 1-11 or an immunogenic fragment thereof, and optionally further comprising a polypeptide having an amino acid sequence comprising a sequence at least 90%, 95%, 98%, or 99% identical to either of SEQ ID NOS: 12 or 13 or an immunogenic fragment thereof. In certain embodiments, the vaccine formulation comprises at least two different polypeptides having an amino acid sequence comprising a sequence at least 90%, 95%, 98%, or 99% identical to any of SEQ ID NOS: 1-13 or an immunogenic fragment thereof, wherein at least one of said polypeptides has an amino acid sequence comprising a sequence at least 90%, 95%, 98%, or 99% identical to one of SEQ ID NOS: 1-10 or an immunogenic fragment thereof.

In some embodiments, one or more, e.g. two, three, four, or more polypeptides from Table 1 or 2 or immunogenic fragments or variants thereof are provided in a mixture. In some embodiments, two, three, four, or more polypeptides from Table 1 or 2 or immunogenic fragments or variants thereof are covalently bound to each other, e.g. as a fusion protein.

In some embodiments, the vaccine formulation contains substantially no other S. pneumoniae polypeptides other than polypeptides having an amino acid sequence comprising any of SEQ ID NOS: 1-13. In some embodiments, the vaccine formulation contains substantially no other S. pneumoniae polypeptides other than polypeptides of Table 1. In some embodiments, the vaccine formulation contains substantially no other S. pneumoniae polypeptides other than polypeptides of Tables 1 or 2.

In certain embodiments, vaccine formulations or immunogenic compositions contain substantially no other S. pneumoniae polypeptides other than polypeptides having an amino acid sequence comprising any of SEQ ID NO: 1-13. In certain such embodiments, vaccine formulations or immunogenic compositions contain substantially no other S. pneumoniae polypeptides other than polypeptides having an amino acid sequence consisting of any of SEQ ID NO: 1-13. In some embodiments, vaccine formulations or immunogenic compositions contain substantially no other S. pneumoniae polypeptides other than polypeptides having an amino acid sequence comprising (or consisting of) any of the amino acid sequences of the polypeptides of Tables 1 and 2. Substantially, in this context, refers to less than 50%, less than 40%, less than 30%, less than 20%, less than 10%, less than 5%, less than 3%, less than 2, or even less than 1% of the other S. pneumoniae polypeptides.

In certain embodiments, the vaccine composition induces a $T_H17$ cell response at least 1.5-fold than that induced by a control irrelevant antigen (such as the HSV-2 protein ICP47 with the gene name US12) after contacting $T_H17$ cells. In some embodiments, the vaccine formulation inhibits infection by S. pneumoniae in an uninfected subject. In some embodiments, the vaccine formulation inhibits S. pneumoniae colonization in an individual. In some embodiments, the vaccine formulation inhibits S. pneumoniae symptoms.

In certain embodiments, this application provides nucleic acids encoding one or more of the polypeptides described above, such as DNA, RNA, or an analog thereof. The underlying DNA sequences for the polypeptides described above may be modified in ways that do not affect the sequence of the protein product, and such sequences are included in the invention. For instance, the DNA sequence may be codon-optimized to improve expression in a host such as *E. coli*, an insect cell line (e.g., using the baculovirus expression system), or a mammalian (e.g., human or Chinese Hamster Ovary) cell line.

In certain embodiments, this application provides nucleic acids (such as DNA. RNA, or an analog thereof) that are at least 70%, 80%, 90%, 95%, 97%, 98%, 99%, or 100% identical to a gene in Table 1 or 2, or a variant or portion of said gene. In certain embodiments, the nucleic acid is 600-2000, 800-1800, 1000-1600, 1200-1400 nucleotides in length. In some embodiments, the nucleic acid is 600-1600, 800-1800, or 1000-2000 nucleotides in length. The nucleic acids may be used, for example, for recombinant production of the polypeptides of Tables 1 and 2, or immunogenic fragments thereof.

In some embodiments, the vaccine or immunogenic composition may comprise fusion proteins and/or fusion DNA constructs. The polypeptides described herein may be used without modification. In certain embodiments, when smaller related polypeptides are used, such as fragments or the like, and their molecular weight is less than about 5000 daltons, e.g., 1500 to 5000 daltons, modification may be useful in eliciting the desired immune response. For example, the smaller polypeptides can be conjugated to an appropriate immunogenic carrier such as tetanus toxoid, pneumolysin keyhole limpet hemocyanin or the like. In certain embodiments, the vaccine formulation comprises at least one lipidated polypeptide. Conjugation may be direct or indirect (e.g., via a linker). In other embodiments, a construct may comprise a gene or protein from Table 1 or 2 or an immunogenic fragment or variant thereof and a tag. A tag may be N-terminal or C-terminal. For instance, tags may be added to the nucleic acid or polypeptide to facilitate purification, detection, solubility, or confer other desirable characteristics on the protein or nucleic acid. For instance, a purification tag may be a peptide, oligopeptide, or polypeptide that may be used in affinity purification. Examples include His, GST, TAP, FLAG, myc, HA, MBP, VSV-G, thioredoxin, V5, avidin, streptavidin, BCCP, Calmodulin, Nus, S tags, lipoprotein D, and β galactosidase. Particular exemplary His tags include HHHHHH (SEQ ID NO: 32) and MSYYHHHHH (SEQ ID NO: 33). In other embodiments, the polypeptide is free of tags such as protein purification tags, and is purified by a method not relying on affinity for a purification tag. In some embodiments, the fused portion is short. This, in some instances, the fusion protein comprises no more than 1, 2, 3, 4, 5, 10, or 20 additional amino acids on one or both termini of the polypeptide of Table 1 or 2.

B. Immunogenic Compositions

The present disclosure also provides pharmaceutical compositions containing immunogenic polypeptides or polynucleotides encoding these immunogenic polypeptides together with a pharmaceutical carrier. Antigens from *S. pneumoniae* were identified by screening immune cells from mice infected with *S. pneumonia*, or from healthy human donors. The human donors had presumably been exposed to *S. pneumoniae* at some point during their lifetimes, because *S. pneumoniae* is a very common disease and colonizing pathogen. Briefly, a library of *S. pneumoniae* antigens was expressed in bacteria and mixed with antigen presenting cells (APCs). The APCs, in turn, presented *S. pneumoniae*-derived polypeptides to lymphocytes that had been isolated from mice or from human donors. Lymphocyte responses were assayed for reactivity to *S. pneumoniae*. Human donors, as well as mice immunized with *S. pneumoniae*, produced lymphocytes specific to *S. pneumoniae* antigens. Thus, the present disclosure contemplates compositions of the *S. pneumoniae* antigens that elicit a strong immune response in immunized or infected mice or humans for counteracting infection by *S. pneumoniae*.

Tables 1 and 2 list the protein sequence and corresponding nucleotide sequence for *S. pneumoniae* antigens identified according to the screening methods described herein. The antigens were identified in screens of mouse and human T cells. In the screens of mouse T cells, the identified antigens were subjected to at least two rounds of screening: a genome-wide round to identify pools of 4 antigens that elicited an immune response, followed by a deconvolution round to individually test and identify single antigens that elicited an immune response from a pool identified in the genome-wide round. In contrast, in the screens of human T cells, two different sets of antigen pools were created, such that a polypeptide was combined with different polypeptides between the first and second pools. Consequently, it is possible to determine which polypeptides are antigens by identifying which polypeptides are in positive pools in both the first and second sets. Table 1 lists antigens (and variants thereof) that were identified by one of the above screening methods, and were subsequently subjected to further testing in the mouse model described in Examples 5-8. Thus, compositions according to this disclosure may include one or two or more of the genes listed in Table 1 or 2, or the corresponding gene products.

An immunogenic composition may also comprise portions of said *Streptococcus* polypeptides, for example deletion mutants, truncation mutants, oligonucleotides, and peptide fragments. In some embodiments, the portions of said polypeptides are immunogenic. The immunogenicity of a portion of a protein is readily determined using the same assays that are used to determine the immunogenicity of the full-length protein. In some embodiments, the portion of the polypeptide has substantially the same immunogenicity as the full-length proteins. In some embodiments, the immunogenicity is no more than 10%, 20%, 30%, 40%, or 50% less than that of the full-length protein (e.g., polypeptides of Tables 1 and 2). The peptide fragments may be, for example, linear, circular, or branched.

Some embodiments of the vaccine formulations and immunogenic compositions described herein include an immunogenic polypeptide (e.g., a polypeptide of Table 1 or 2) that contains a membrane translocating sequence (MTS), to facilitate introduction of the polypeptide into the mammalian cell and subsequent stimulation of the cell-mediated immune response. Exemplary membrane translocating sequences include hydrophobic region in the signal sequence of Kaposi fibroblast growth factor, the MTS of α-synuclein, β-synuclein, or γ-synuclein, the third helix of the Antennapedia homeodomain, SN50, integrin β3 h-region, HIV Tat, pAntp, PR-39, abaecin, apidaecin, Bac5, Bac7, *P. berghei* CS protein, and those MTSs described in U.S. Pat. Nos. 6,248,558, 6,432,680 and 6,248,558.

In certain embodiments, an antigen (e.g., a polypeptide of Table 1 or 2) is covalently bound to another molecule. This may, for example, increase the half-life, solubility, bioavailability, or immunogenicity of the antigen. Molecules that may be covalently bound to the antigen include a carbohydrate, biotin, poly(ethylene glycol) (PEG), polysialic acid, N-propionylated polysialic acid, nucleic acids, polysaccharides, and PLGA. There are many different types of PEG, ranging from molecular weights of below 300 g/mol to over 10,000,000 g/mol. PEG chains can be linear, branched, or with comb or star geometries. In some embodiments, the naturally produced form of a protein is covalently bound to a moeity that stimulates the immune system. An example of such a moeity is a lipid moeity. In some instances, lipid moieties are recognized by a Toll-like receptor (TLR) such as TLR2, and activate the innate immune system.

C. Antibodies Specific to the Proteins of Tables 1 and 2

Another aspect disclosed herein is an antibody preparation generated against an antigenic composition (e.g., one of the proteins listed in Table 1 or 2 or an immunogenic fragment thereof). For instance, this disclosure provides combinations of two, three, four, or five antibodies each recognizing a different protein of Table 1 or 2. Any of a variety of antibodies are included. Such antibodies include, e.g., polyclonal, monoclonal, recombinant, humanized or partially humanized, single chain, Fab, and fragments thereof, etc. The antibodies can be of any isotype, e.g., IgG, various IgG isotypes such as IgG1, IgG2, IgG2a, IgG2b, IgG3, IgG4, etc.; and they can be from any animal species that produces antibodies, including goat, rabbit, mouse, chicken or the like. In some embodiments, Fab molecules are expressed and assembled in a genetically transformed host like *E. coli*. A lambda vector system is available thus to express a population of Fab's with a potential diversity equal to or exceeding that of subject generating the predecessor antibody. See Huse et al. (1989), Science 246, 1275-81.

D. Components of a Vaccine or Immunogenic Composition Comprising *S. pneumoniae* Antigens or Antibodies Recognizing the Same In certain embodiments, the vaccine or immunogenic composition comprises an antigen and one or more of the following: an adjuvant, stabilizer, buffer, surfactant, controlled release component, salt, preservative, and an antibody specific to said antigen.

1. Adjuvants

The vaccine formulations and immunogenic compositions described herein may include an adjuvant. Adjuvants can be broadly separated into two classes, based on their principal mechanisms of action: vaccine delivery systems and immunostimulatory adjuvants (see, e.g., Singh et al., *Curr. HIV Res.* 1:309-20, 2003). Vaccine delivery systems are often particulate formulations, e.g., emulsions, microparticles, immune-stimulating complexes (ISCOMs), which may be, for example, particles and/or matrices, and liposomes. In contrast, immunostimulatory adjuvants are sometimes derived from pathogens and can represent pathogen associated molecular patterns (PAMP), e.g., lipopolysaccharides (LPS), monophosphoryl lipid (MPL), or CpG-containing DNA, which activate cells of the innate immune system.

Alternatively, adjuvants may be classified as organic and inorganic. Inorganic adjuvants include alum salts such as aluminum phosphate, amorphous aluminum hydroxyphosphate sulfate, and aluminum hydroxide, which are commonly used in human vaccines. Organic adjuvants comprise organic molecules including macromolecules. An example of an organic adjuvant is cholera toxin.

Adjuvants may also be classified by the response they induce. In some embodiments, the adjuvant induces the activation of $T_H1$ cells or $T_H2$ cells. In other embodiments, the adjuvant induces the activation of B cells. In yet other embodiments, the adjuvant induces the activation of antigen-presenting cells. These categories are not mutually exclusive; in some cases, an adjuvant activates more than one type of cell.

In certain embodiments, the adjuvant induces the activation of $T_H17$ cells. It may promote the $T_H17$ cells to secrete IL-17. In some embodiments, an adjuvant that induces the activation of $T_H17$ cells is one that produces at least a 2-fold, and in some cases a 10-fold, experimental sample to control ratio in the following assay. In the assay, an experimenter compares the IL-17 levels secreted by two populations of cells: (1) cells treated with the adjuvant and a polypeptide known to induce $T_H17$ activation, and (2) cells treated with the adjuvant and an irrelevant (control) polypeptide. An adjuvant that induces the activation of $T_H17$ cells may cause the cells of population (1) to produce more than 2-fold, or more than 10-fold more IL-17 than the cells of population (2). IL-17 may be measured, for example, by ELISA or Western blot. Certain toxins, such as cholera toxin and labile toxin (produced by enterotoxigenic *E. coli*, or ETEC), activate a $T_H17$ response. Thus, in some embodiments, the adjuvant is a toxin. Cholera toxin was successfully used in the mouse model to induce protective immunity in conjunction with certain polypeptides from Table 1 (see Examples 5-8). One form of labile toxin is produced by Intercell. Mutant derivates of labile toxin that are active as adjuvants but significantly less toxic can be used as well. Exemplary detoxified mutant derivatives of labile toxin include mutants lacking ADP-ribosyltransferase activity. Particular detoxified mutant derivatives of labile toxin include LTK7 (Douce et al., "Mutants of *Escherichia coli* heat-labile toxin lacking ADP-ribosyltransferase activity act as nontoxic, mucosal adjuvants" *PNAS* Vol. 92, pp. 1644-1648, February 1995) and LTK63 (Williams et al., "Innate Imprinting by the Modified Heat-Labile Toxin of *Escherichia coli* (LTK63) Provides Generic Protection against Lung Infectious Disease" The Journal of Immunology, 2004, 173: 7435-7443), LT-G192 (Douce et al. "Genetically detoxified mutants of heat-labile toxin from *Escherichia coli* are able to act as oral adjuvants" Infect Immun. 1999 September; 67(9):4400-6), and LTR72 ("Mucosal adjuvanticity and immunogenicity of LTR72, a novel mutant of *Escherichia coli* heat-labile enterotoxin with partial knockout of ADP-ribosyltransferase activity." J Exp Med. 1998 Apr. 6;187(7):1123-32).

In some embodiments, the adjuvant comprises a VLP (virus-like particle). One such adjuvant platform, Alphavirus replicons, induces the activation of $T_H17$ cells using alphavirus and is produced by Alphavax. In certain embodiments of the Alphavirus replicon system, alphavirus may be engineered to express an antigen of interest, a cytokine of interest (for example, IL-17 or a cytokine that stimulates IL-17 production), or both, and may be produced in a helper cell line. More detailed information may be found in U.S. Pat. Nos. 5,643,576 and 6,783,939. In some embodiments, a vaccine formulation is administered to a patient in combination with a nucleic acid encoding a cytokine.

Certain classes of adjuvants activate toll-like receptors (TLRs) in order to activate a $T_H 17$ response. TLRs are well known proteins that may be found on leukocyte membranes, and recognize foreign antigens (including microbial antigens). Administering a known TLR ligand together with an antigen of interest (for instance, as a fusion protein) can promote the development of an immune response specific to the antigen of interest. One exemplary adjuvant that activates TLRs comprises Monophosphoryl Lipid A (MPL). Traditionally, MPL has been produced as a detoxified lipopolysaccharide (LPS) endotoxin obtained from gram negative bacteria, such as *S. minnesota*. In particular, sequential acid and base hydrolysis of LPS produces an immunoactive lipid A fraction (which is MPL), and lacks the saccharide groups and all but one of the phosphates present in LPS. A number of synthetic TLR agonists (in particular, TLR4 agonists) are disclosed in Evans J T et al. "Enhancement of antigen-specific immunity via the TLR4 ligands MPL adjuvant and Ribi.529." Expert Rev Vaccines 2003 April; 2(2):219-29. Like MPL adjuvants, these synthetic compounds activate the innate immune system via TLR. Another type of TLR agonist is a synthetic phospholipid dimer, for example E6020 (Ishizaka S T et al. "E6020: a synthetic Toll-like receptor 4 agonist as a vaccine adjuvant." Expert Rev. Vaccines. 2007 October; 6(5):773-84.). Various TLR agonists (including TLR4 agonists) have been produced and/or sold by, for example, the Infectious Disease Research Institute (IRDI), Corixa, Esai, Avanti Polar Lipids. Inc., and Sigma Aldrich. Another exemplary adjuvant that activates TLRs comprises a mixture of MPL, Trehalose Dicoynomycolate (TDM), and dioctadecyldimethylammonium bromide (DDA). Another TLR-activating adjuvant is R848 (resiquimod).

In some embodiments, the adjuvant is or comprises a saponin. Typically, the saponin is a triterpene glycoside, such as those isolated from the bark of the *Quillaja saponaria* tree. A saponin extract from a biological source can be further fractionated (e.g., by chromatography) to isolate the portions of the extract with the best adjuvant activity and with acceptable toxicity. Typical fractions of extract from *Quillaja saponaria* tree used as adjuvants are known as fractions A and C.

A particular form of saponins that may be used in vaccine formulations described herein is immunostimulating complexes (ISCOMs). ISCOMs are an art-recognized class of adjuvants, that generally comprise *Quillaja* saponin fractions and lipids (e.g., cholesterol and phospholipids such as phosphatidyl choline). In certain embodiments, an ISCOM is assembled together with a polypeptide or nucleic acid of interest. However, different saponin fractions may be used in different ratios. In addition, the different saponin fractions may either exist together in the same particles or have substantially only one fraction per particle (such that the indicated ratio of fractions A and C are generated by mixing together particles with the different fractions). In this context, "substantially" refers to less than 20%, 15%, 10%, 5%, 4%, 3%, 2% or even 1%. Such adjuvants may comprise fraction A and fraction C mixed into a ratio of 70-95 A:30-5 C, such as 70 A:30 C to 75 A:5 C, 75 A:5 C to 80 A:20 C, 80 A:20 C to 85 A:15 C, 85 A:15 C to 90 A:10 C, 90 A:10 C to 95 A:5 C, or 95 A:5 C to 99 A:1 C.

In certain embodiments, combinations of adjuvants are used. Three exemplary combinations of adjuvants are MPL and alum, E6020 and alum, and MPL and an ISCOM.

Adjuvants may be covalently bound to antigens. In some embodiments, the adjuvant may comprise a protein which induces inflammatory responses through activation of antigen-presenting cells (APCs). In some embodiments, one or more of these proteins can be recombinantly fused with an antigen of choice, such that the resultant fusion molecule promotes dendritic cell maturation, activates dendritic cells to produce cytokines and chemokines, and ultimately, enhances presentation of the antigen to T cells and initiation of T cell responses (see Wu et al., Cancer Res 2005; 65(11), pp 4947-4954). In certain embodiments, a polypeptide described herein is presented in the context of the trivalent *S. pneumoniae* Pneumococcal surface adhesin A: pneumolysin derivative carrying three amino acid substitutions (W433F, D385N, and C428G) which render the molecule nontoxic but do not interfere with TLR4-mediated inflammatory properties-cell wall polysaccharide (PsaA:PdT-CPs) conjugate system described in Lu et al. ("Protection against Pneumococcal colonization and fatal pneumonia by a trivalent conjugate of a fusion protein with the cell wall polysaccharide." *Infect Immun.* 2009 May; 77(5):2076-83). The conjugate system is "a fusion protein of PsaA with the pneumolysin nontoxic derivative PdT and then coupled CPs to the fusion protein". In some embodiments, one or more polypeptides described herein is used in place of PsaA in the trivalent conjugate. The trivalent conjugate system typically includes alum and is usually administered parenterally. Other exemplary adjuvants that may be covalently bound to antigens comprise polysaccharides, pneumolysin, synthetic peptides, lipopeptides, and nucleic acids.

Typically, the same adjuvant or mixture of adjuvants is present in each dose of a vaccine. Optionally, however, an adjuvant may be administered with the first dose of vaccine and not with subsequent doses (i.e., booster shots). Alternatively, a strong adjuvant may be administered with the first dose of vaccine and a weaker adjuvant or lower dose of the strong adjuvant may be administered with subsequent doses. The adjuvant can be administered before the administration of the antigen, concurrent with the administration of the antigen or after the administration of the antigen to a subject (sometimes within 1, 2, 6, or 12 hours, and sometimes within 1, 2, or 5 days). Certain adjuvants are appropriate for human patients, non-human animals, or both.

2. Additional Components of a Vaccine or Immunogenic Composition

In addition to the antigens and the adjuvants described above, a vaccine formulation or immunogenic composition may include one or more additional components.

In certain embodiments, the vaccine formulation or immunogenic composition may include one or more stabilizers such as sugars (such as sucrose, glucose, or fructose), phosphate (such as sodium phosphate dibasic, potassium phosphate monobasic, dibasic potassium phosphate, or monosodium phosphate), glutamate (such as monosodium L-glutamate), gelatin (such as processed gelatin, hydrolyzed gelatin, or porcine gelatin), amino acids (such as arginine, asparagine, histidine, L-histidine, alanine, valine, leucine, isoleucine, serine, threonine, lysine, phenylalanine, tyrosine, and the alkyl esters thereof), inosine, or sodium borate.

In certain embodiments, the vaccine formulation or immunogenic composition includes one or more buffers such as a mixture of sodium bicarbonate and ascorbic acid. In some embodiments, the vaccine formulation may be administered in saline, such as phosphate buffered saline (PBS), or distilled water.

In certain embodiments, the vaccine formulation or immunogenic composition includes one or more surfactants such as polysorbate 80 (TWEEN® 80), Polyethylene glycol tert-octylphenyl ether t-Octylphenoxypolyethoxyethanol 4-(1,1,3,3 Tetramethylbutyl)phenyl-polyethylene glycol (TRITON® X-100); Polyoxyethylenesorbitan monolaurate Polyethylene glycol sorbitan monolaurate (TWEEN® 20); and 4-(1,1,3,3-Tetramethylbutyl)phenol polymer with formaldehyde and oxirane (TYLOXAPOL®). A surfactant can be ionic or nonionic.

In certain embodiments, the vaccine formulation or immunogenic composition includes one or more salts such as sodium chloride, ammonium chloride, calcium chloride, or potassium chloride.

In certain embodiments, a preservative is included in the vaccine or immunogenic composition. In other embodiments, no preservative is used. A preservative is most often used in multi-dose vaccine vials, and is less often needed in single-dose vaccine vials. In certain embodiments, the preservative is 2-phenoxyethanol, methyl and propyl parabens, benzyl alcohol, and/or sorbic acid.

In certain embodiments, the vaccine formulation or immunogenic composition is a controlled release formulation.

E. DNA Vaccines

In certain aspects, the vaccine comprises one of the nucleic acids disclosed herein or a nucleic acid corresponding to one of the polypeptides described herein. When a nucleic acid vaccine is administered to a patient, the corresponding gene product (such as a desired antigen) is produced in the patient's body. In some embodiments, nucleic acid vaccine vectors that include optimized recombinant polynucleotides can be delivered to a mammal (including humans) to induce a therapeutic or prophylactic immune response. The nucleic acid may be, for example, DNA, RNA, or a synthetic nucleic acid. The nucleic acid may be single stranded or double stranded.

Nucleic acid vaccine vectors (e.g., adenoviruses, liposomes, papillomaviruses, retroviruses, etc.) can be administered directly to the mammal for transduction of cells in vivo. The nucleic acid vaccines can be formulated as pharmaceutical compositions for administration in any suitable manner, including parenteral administration.

In determining the effective amount of the vector to be administered in the treatment or prophylaxis of an infection or other condition, the physician evaluates vector toxicities, progression of the disease, and the production of anti-vector antibodies, if any. Often, the dose equivalent of a naked nucleic acid from a vector is from about 1 μg to 1 mg for a typical 70 kilogram patient, and doses of vectors used to deliver the nucleic acid are calculated to yield an equivalent amount of therapeutic nucleic acid. Administration can be accomplished via single or divided doses. The toxicity and therapeutic efficacy of the nucleic acid vaccine vectors can be determined using standard pharmaceutical procedures in cell cultures or experimental animals.

A nucleic acid vaccine can contain DNA, RNA, a modified nucleic acid, or a combination thereof. In some embodiments, the vaccine comprises one or more cloning or expression vectors; for instance, the vaccine may comprise a plurality of expression vectors each capable of autonomous expression of a nucleotide coding region in a mammalian cell to produce at least one immunogenic polypeptide. An expression vector often includes a eukaryotic promoter sequence, such as the nucleotide sequence of a strong eukaryotic promoter, operably linked to one or more coding regions. The compositions and methods herein may involve the use of any particular eukaryotic promoter, and a wide variety are known; such as a CMV or RSV promoter. The promoter can be heterologous with respect to the host cell. The promoter used may be a constitutive promoter.

A vector useful in the present compositions and methods can be circular or linear, single-stranded or double stranded and can be a plasmid, cosmid, or episome. In a suitable embodiment, each nucleotide coding region is on a separate vector; however, it is to be understood that one or more coding regions can be present on a single vector, and these coding regions can be under the control of a single or multiple promoters.

Numerous plasmids may be used for the production of nucleic acid vaccines. Suitable embodiments of the nucleic acid vaccine employ constructs using the plasmids VR1012 (Vical Inc., San Diego Calif.), pCMVI.UBF3/2 (S. Johnston. University of Texas) or pcDNA3.1 (InVitrogen Corporation, Carlsbad, Calif.) as the vector. In addition, the vector construct can contain immunostimulatory sequences (ISS), such as unmethylated dCpG motifs, that stimulate the animal's immune system. The nucleic acid vaccine can also encode a fusion product containing the immunogenic polypeptide. Plasmid DNA can also be delivered using attenuated bacteria as delivery system, a method that is suitable for DNA vaccines that are administered orally. Bacteria are transformed with an independently replicating plasmid, which becomes released into the host cell cytoplasm following the death of the attenuated bacterium in the host cell.

An alternative approach to delivering the nucleic acid to an animal involves the use of a viral or bacterial vector. Examples of suitable viral vectors include adenovirus, polio virus, pox viruses such as vaccinia, canary pox, and fowl pox, herpes viruses, including catfish herpes virus, adenovirus-associated vector, and retroviruses. Exemplary bacterial vectors include attenuated forms of *Salmonella, Shigella, Edwardsiella ictaluri, Yersinia ruckerii*, and *Listeria monocytogenes*. In some embodiments, the nucleic acid is a vector, such as a plasmid, that is capable of autologous expression of the nucleotide sequence encoding the immunogenic polypeptide.

F. Use of Vaccines

The *S. pneumoniae* vaccines described herein may be used for prophylactic and/or therapeutic treatment of *S. pneumoniae*. Accordingly, this application provides a method for treating a subject suffering from or susceptible to *S. pneumoniae* infection, comprising administering an effective amount of any of the vaccine formulations described herein. In some aspects, the method inhibits *S. pneumoniae* colonization in an individual. In some aspects, the method inhibits *S. pneumoniae* symptoms. The subject receiving the vaccination may be a male or a female, and may be a child or adult. In some embodiments, the subject being treated is a human. In other embodiments, the subject is a non-human animal.

1. Prophylactic Use

In prophylactic embodiments, the vaccine is administered to a subject to induce an immune response that can help protect against the establishment of *S. pneumoniae*, for example by protecting against colonization, the first and necessary step in disease. Thus, in some aspects, the method inhibits infection by *S. pneumoniae* in a noncolonized or uninfected subject. In another aspect, the method may reduce the duration of colonization in an individual that is already colonized.

In some embodiments, the vaccine compositions of the invention confer protective immunity, allowing a vaccinated individual to exhibit delayed onset of symptoms or reduced severity of symptoms, as the result of his or her exposure to the vaccine. In certain embodiments, the reduction in severity of symptoms is at least 25%, 40%, 50%, 60%, 70%, 80% or even 90%. In particular embodiments, vaccinated individuals may display no symptoms upon contact with *S. pneumoniae*, do not become colonized by *S. pneumoniae*, or both. Protective immunity is typically achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes, that result in sIGA production by B lymphocytes on mucosa-lined tissues of the body. Humoral immunity is typically the result of IgG antibodies and IgM antibodies in serum. Cellular immunity can be achieved through cytotoxic T lymphocytes or through delayed-type hypersensitivity that involves macrophages and T lymphocytes, as well as other mechanisms involving T cells without a requirement for antibodies. In particular, cellular immunity may be mediated by $T_H1$ or $T_H17$ cells.

Essentially any individual has a certain risk of becoming infected with *S. pneumoniae*. However, certain sub-populations have an increased risk of infection. In some embodiments, a vaccine formulation as described herein (e.g., a composition comprising one or more polypeptides from Table 1 or 2, or nucleic acids encoding the polypeptides, or antibodies reactive with the polypeptides) is administered to patients that are immunocompromised.

An immunocompromising condition arising from a medical treatment is likely to expose the individual in question to a higher risk of infection with *S. pneumoniae*. It is possible to treat an infection prophylactically in an individual having the immunocompromised condition before or during treatments known to compromise immune function. By prophylactically treating with an antigenic composition (e.g., two or more antigens from Table 1 or 2, or nucleic acids encoding the antigens), or with antibodies reactive to two or more antigens from Table 1 or 2, before or during a treatment known to compromise immune function, it is possible to prevent a subsequent *S. pneumoniae* infection or to reduce the risk of the individual contracting an infection due to the immunocompromised condition. Should the individual contract an *S. pneumoniae* infection e.g., following a treatment leading to an immunocompromised condition it is also possible to treat the infection by administering to the individual an antigen composition.

The following groups are at increased risk of pneumococcal disease or its complications, and therefore it is advantageous for subjects falling into one or more of these groups to receive a vaccine formulation described herein: children, especially those from 1 month to 5 years old or 2 months to 2 years old; children who are at least 2 years of age with asplenia, splenic dysfunction or sickle-cell disease; children who are at least 2 years of age with nephrotic syndrome, chronic cerebrospinal fluid leak, HIV infection or other conditions associated with immunosuppression.

In another embodiment, at least one dose of the pneumococcal antigen composition is given to adults in the following groups at increased risk of pneumococcal disease or its complications: all persons 65 years of age; adults with asplenia, splenic dysfunction or sickle-cell disease; adults with the following conditions: chronic cardiorespiratory disease, cirrhosis, alcoholism, chronic renal disease, nephrotic syndrome, diabetes mellitus, chronic cerebrospinal fluid leak, HIV infection, AIDS and other conditions associated with immunosuppression (Hodgkin's disease, lymphoma, multiple myeloma, immunosuppression for organ transplantation), individuals with cochlear implants; individuals with long-term health problems such as heart disease and lung disease, as well as individuals who are taking any drug or treatment that lowers the body's resistance to infection, such as long-term steroids, certain cancer drugs, radiation therapy; Alaskan natives and certain Native American populations.

2. Therapeutic Use

In therapeutic applications, the vaccine may be administered to a patient suffering from *S. pneumoniae* infection, in an amount sufficient to treat the patient. Treating the patient, in this case, refers to reducing symptoms, bacterial load, or both of *S. pneumoniae* in an infected individual. In some embodiments, treating the patient refers to reducing the duration of symptoms or reducing the intensity of symptoms. In some embodiments, the vaccine reduces transmissibility of *S. pneumoniae* from the vaccinated patient. In certain embodiments, the reductions described above are at least 25%, 30%, 40%, 50%, 60%, 70%, 80% or even 90%.

In therapeutic embodiments, the vaccine is administered to an individual post-infection. The vaccine may be administered shortly after infection, e.g. before symptoms manifest, or may be administered during or after manifestation of symptoms.

A therapeutic *S. pneumoniae* vaccine can reduce the intensity and/or duration symptoms of the various indications of *S. pneumoniae* infection. A *S. pneumoniae* infection can take many forms. In some cases, an infected patient develops pneumonia, acute sinusitis, otitis media (ear infection), meningitis, bacteremia, sepsis, osteomyelitis, septic arthritis, endocarditis, peritonitis, pericarditis, cellulitis, or brain abscess.

3. Assaying Vaccination Efficacy

The efficacy of vaccination with the vaccines disclosed herein may be determined in a number of ways, in addition to the clinical outcomes described above. First, one may assay IL-17 levels (particularly IL-17A) by stimulating T cells derived from the subject after vaccination. The IL-17 levels may be compared to IL-17 levels in the same subject before vaccination. Increased IL-17 (e.g., IL-17A) levels, such as a 1.5 fold, 2-fold, 5-fold, 10-fold, 20-fold, 50-fold or 100-fold or more increase, would indicate an increased response to the vaccine. Alternatively (or in combination), one may assay neutrophils in the presence of T cells or antibodies from the patient for pneumococcal killing. Increased pneumococcal killing, such as a 1.5 fold, 2-fold, 5-fold, 10-fold, 20-fold, 50-fold or 100-fold or more increase, would indicate an increased response to the vaccine. In addition, one may measure $T_H17$ cell activation, where increased $T_H17$ cell activation, such as a 1.5 fold, 2-fold, 5-fold, 10-fold, 20-fold, 50-fold or 100-fold or more increase, correlates with an increased response to the vaccine. One may also measure levels of an antibody specific to the vaccine, where increased levels of the specific antibody, such as a 1.5 fold, 2-fold, 5-fold, 10-fold, 20-fold, 50-fold or 100-fold or more increase, are correlated with increased vaccine efficacy. In certain embodiments, two or more of these assays are used. For example, one may measure IL-17 levels and the levels of vaccine-specific antibody. Alternatively, one may follow epidemiological markers such as incidence of, severity of, or duration of pneumococcal infection in vaccinated individuals compared to unvaccinated individuals.

Vaccine efficacy may also be assayed in various model systems such as the mouse model. For instance, BALB/c or C57BL/6 strains of mice may be used. After administering the test vaccine to a subject (as a single dose or multiple doses), the experimenter administers a challenge dose of *S. pneumoniae*. In some cases, the challenge dose is sufficient to cause *S. pneumoniae* colonization (especially nasal colonization) in an unvaccinated animal, and in some cases the challenge dose is sufficient to cause a high rate of lethality in unvaccinated animals. One can then measure the reduction in colonization or the reduction in lethality in vaccinated animals. Examples 5 and 6 show the efficacy of polypeptides of Table 1 in inhibiting *S. pneumoniae* nasal colonization in the mouse model.

G. Use of Immunogenic Compositions

1. Defense Against *S. pneumoniae* Infection

The immunogenic compositions of the present disclosure are designed to elicit an immune response against *S. pneumoniae*. Compositions described herein (e.g., ones comprising one or more polypeptides of Table 1 or 2, or nucleic acids encoding the polypeptides) may stimulate an antibody response or a cell-mediated immune response, or both, in the mammal to which it is administered. In some embodiments, the composition stimulates a $T_H1$-biased CD4+ T cell response, a $T_H17$-biased CD4+ T cell response, or a CD8+ T cell response; in the case of a single component composition, the composition may stimulate an antibody response, a $T_H1$-biased CD4+ T cell response, $T_H17$-biased CD4+ T cell response, and/or a CD8+ T cell response.

In certain embodiments, the composition (e.g., one comprising one or more polypeptides of Table 1 or 2, or nucleic acids encoding the polypeptides, or antibodies reactive with the peptides) includes a cytokine or nucleotide coding region encoding a cytokine such as IL-17, to provide additional stimulation to the immune system of the mammal. In certain embodiments, the composition comprises a cytokine such as IL-17.

While not wishing to be bound by theory, in some embodiments a $T_H17$ cell response is beneficial in mounting an immune response to the compositions disclosed herein, e.g., ones comprising one or more polypeptides of Table 1 or 2. In certain embodiments, an active $T_H17$ response is beneficial in clearing a pneumococcal infection. For instance, mice lacking the IL-17A receptor show decreased whole cell vaccine-based protection from a pneumococcal challenge (Lu et al., "Interleukin-17A mediates acquired immunity to pneumococcal colonization." PLoS Pathog. 2008 Sep. 19; 4(9)). Furthermore, the same authors showed that the response level of IL-17A was increased in mice treated with a whole-cell vaccine.

Thus, herein is provided a method of increasing IL-17 production by administering the compositions described herein (e.g., ones comprising one or more polypeptides of Table 1 or 2) to a subject. Furthermore, this application provides a method of activating $T_H7$ cells by administering said compositions to a subject. In certain embodiments, increased IL-17A levels result in increased pneumococcal killing by neutrophils or neutrophil-like cells, for instance by inducing recruitment and activation of neutrophils of neutrophil-like cells. In certain embodiments, this pneumococcal killing is independent of antibodies and complement. However, specific antibody production and complement activation may be useful additional mechanisms that contribute to clearing of a pneumococcal infection.

Immunogenic compositions containing immunogenic polypeptides or polynucleotides encoding immunogenic polypeptides together with a pharmaceutical carrier are also provided.

In some instances, the immunogenic composition comprises one or more nucleic acids encoding one or more polypeptides of SEQ ID NOS: 1-13, such as one or more nucleic acids selected from SEQ ID Nos. 24-31. In some embodiments these nucleic acids are expressed in the immunized individual, producing the encoded S. pneumoniae antigens, and the S. pneumoniae antigens so produced can produce an immunostimulatory effect in the immunized individual.

Such a nucleic acid-containing immunostimulatory composition may comprise, for example, an origin of replication, and a promoter that drives expression of one or more nucleic acids encoding one or more polypeptides of SEQ ID NOS: 1-13. Such a composition may also comprise a bacterial plasmid vector into which is inserted a promoter (sometimes a strong viral promoter), one or more nucleic acids encoding one or more polypeptides of SEQ ID NOS: 1-13, and a polyadenylation/transcriptional termination sequence. In some instances, the nucleic acid is DNA.

H. Diagnostic Uses

This application provides, inter alia, a rapid, inexpensive, sensitive, and specific method for detection of S. pneumoniae in patients. In this respect it should be useful to all hospitals and physicians examining and treating patients with or at risk for S. pneumoniae infection. Detection kits can be simple enough to be set up in any local hospital laboratory, and the antibodies and antigen-binding portions thereof can readily be made available to all hospitals treating patients with or at risk for S. pneumoniae infection. As used herein, "patient" refers to an individual (such as a human) that either has an S. pneumoniae infection or has the potential to contract an S. pneumoniae infection. A patient may be an individual (such as a human) that has an S. pneumoniae infection, has the potential to contract an S. pneumoniae infection, who has recovered from S. pneumoniae infection, and/or an individual whose infection status is unknown.

In some embodiments, one may perform a diagnostic assay using two or more antibodies, each of which binds one of the antigens of Table 1 and 2 to detect S. pneumoniae in an individual. The instant disclosure also provides a method of phenotyping biological samples from patients suspected of having a S. pneumoniae infection: (a) obtaining a biological sample from a patient; (b) contacting the sample with two or more S. pneumoniae-specific antibodies or antigen-binding portions thereof under conditions that allow for binding of the antibody or antigen-binding portion to an epitope of S. pneumoniae; where binding indicates the presence of S. pneumoniae in the sample. In some embodiments, the binding to the biological sample is compared to binding of the same antibody to a negative control tissue, wherein if the biological sample shows the presence of S. pneumoniae as compared to the negative control tissue, the patient is identified as likely having a S. pneumoniae infection. In some cases, binding of one antibody indicates the presence of S. pneumoniae; in other cases, the binding of two or more antibodies indicates the presence of S. pneumoniae. The aforementioned test may be appropriately adjusted to detect other bacterial infections, for instance by using an antibody immunoreactive a homolog (from another bacterial species) of one of the proteins described in Table 1. In some embodiments, the antibodies raised against a S. pneumoniae protein in Table 1 or 2 will also bind the homolog in another Streptococcus species, especially if the homologs have a high percentage sequence identity.

Alternatively, one may use an antigen of Table 1 or 2 to detect anti-S. pneumoniae antibodies in an individual. The instant disclosure also provides a method of phenotyping biological samples from patients suspected of having a S. pneumoniae infection: (a) obtaining a biological sample from a patient; (b) contacting the sample with two or more S. pneumoniae-specific antigens selected from Table 1 or 2 or portions thereof under conditions that allow for binding of the antigen (or portion thereof) to any host antibodies present in the sample; where binding indicates the presence of anti-S. pneumoniae antibodies in the sample. In some embodiments, the binding to the biological sample is compared to binding of the same antigen to a negative control tissue, wherein if the biological sample shows the presence of anti-S. pneumoniae antibodies as compared to the negative control tissue, the patient is identified as likely either (1) having a S. pneumoniae infection, or (2) having had a S. pneumoniae infection in the past. In some cases, detecting one antibody indicates a current or past infection with S.

*pneumoniae*; in other cases, detecting two or more antibodies indicates a current or past infection with *S. pneumoniae*. The aforementioned test may be appropriately adjusted to detect other bacterial infections, for instance by using a homolog (from another bacterial species (e.g., a *Streptococcal* species) of the proteins described in Table 1.

In some embodiments, the immune cell response of a mammalian cell may be quantified ex vivo. A method for such quantification comprises administering the compositions herein disclosed to a mammalian T cell ex vivo, and quantifying the change in cytokine production of the mammalian T cell in response to the composition. In these methods, the cytokine may be, for example, IL-17.

The binding of an *S. pneumoniae* antibody to an antigen (e.g., a polypeptide of Table 1 or 2) may be measured using any appropriate method. Such methods include ELISA (enzyme-linked immunosorbent assay), Western blotting, competition assay, and spot-blot. The detection step may be, for instance, chemiluminescent, fluorescent, or colorimetric. One suitable method for measuring antibody-protein binding is the Luminex xMAP system, where peptides are bound to a dye-containing microsphere. Certain systems, including the xMAP system, are amenable to measuring several different markers in multiplex, and could be used to measure levels of antibodies at once. In some embodiments, other systems are used to assay a plurality of markers in multiplex. For example, profiling may be performed using any of the following systems: antigen microarrays, bead microarrays, nanobarcodes particle technology, arrayed proteins from cDNA expression libraries, protein in situ array, protein arrays of living transformants, universal protein array, lab-on-a-chip microfluidics, and peptides on pins. Another type of clinical assay is a chemiluminescent assay to detect antibody binding. In some such assays, including the VITROS Eci anti-HCV assay, antibodies are bound to a solid-phase support made up of microparticles in liquid suspension, and a surface fluorometer is used to quantify the enzymatic generation of a fluorescent product.

In some embodiments, if the biological sample shows the presence of *S. pneumoniae* (e.g., by detecting one or more polypeptide of Table 1 or 2 or an antibody that binds one of said polypeptides), one may administer a therapeutically effective amount of the compositions and therapies described herein to the patient. The biological sample may comprise, for example, blood, semen, urine, vaginal fluid, mucus, saliva, feces, urine, cerebrospinal fluid, or a tissue sample. In some embodiments, the biological sample is an organ intended for transplantation. In certain embodiments, before the detection step, the biological sample is subject to culture conditions that promote the growth of *S. pneumoniae*.

The diagnostic tests herein (e.g., those that detect a polypeptide of Table 1 or 2 or an antibody that binds one of said polypeptides) may be used to detect *S. pneumoniae* in a variety of samples, including samples taken from patients and samples obtained from other sources. For example, the diagnostic tests may be used to detect *S. pneumoniae* in food, drink, or ingredients for food and drink; on objects such as medical instruments, medical devices such as cochlear implants and pacemakers, shoes, clothing, furniture including hospital furniture, and drapes including hospital drapes; or in samples taken from the environment such as plant samples. In some embodiments, the tests herein may be performed on samples taken from animals such as agricultural animals (cows, pigs, chickens, goats, horses and the like), companion animals (dogs, cats, birds, and the like), or wild animals. In certain embodiments, the tests herein may be performed on samples taken from cell cultures such as cultures of human cells that produce a therapeutic protein, cultures of bacteria intended to produce a useful biological molecule, or cultures of cells grown for research purposes.

This disclosure also provides a method of determining the location of a *S. pneumoniae* infection in a patient comprising: (a) administering a pharmaceutical composition comprising a labeled *S. pneumoniae* antibody or antigen-binding portion thereof to the patient, and (b) detecting the label, wherein binding indicates a *S. pneumoniae* infection in a particular location in the patient. Such a diagnostic may also comprise comparing the levels of binding in the patient to a control. In certain embodiments, the method further comprises, if the patient has a *S. pneumoniae* infection, treating the infection by administering a therapeutically effective amount of a *S. pneumoniae*-binding antibody or antigen-binding portion thereof to the patient. In certain embodiments, the method further comprises, if the patient has a *S. pneumoniae* infection, treating the infection by administering a therapeutically effective amount of a *S. pneumoniae* protein of Table 1, or immunogenic portion thereof, to the patient. The method may further comprise determining the location and/or volume of the *S. pneumoniae* in the patient. This method may be used to evaluate the spread of *S. pneumoniae* in the patient and determine whether a localized therapy is appropriate.

In some embodiments, the anti-*S. pneumoniae* antibodies described herein may be used to make a prognosis of the course of infection. In some embodiments, the anti-*S. pneumoniae* antibodies herein may be detected in a sample taken from a patient. If antibodies are present at normal levels, it would indicate that the patient has raised an immune response against anti-*S. pneumoniae*. If antibodies are absent, or present at reduced levels, it would indicate that the patient is failing to raise a sufficient response against anti-*S. pneumoniae*, and a more aggressive treatment would be recommended. In some embodiments, antibodies present at reduced levels refers to antibodies that are present at less than 50%, 20%, 10%, 5%, 2%, or 1% the level of antibodies typical in a patient with a normal immune system. Antibodies may be detected by affinity for any of the antigens described herein (e.g., those in Table 1 and/or 2), for example using ELISA.

In some embodiments, detection of specific *S. pneumoniae* antigens (e.g., those in Table 1 and/or 2) may be used to predict the progress and symptoms of *S. pneumoniae* infection in a patient. It will be understood by one of skill in the art that the methods herein are not limited to detection of *S. pneumoniae*. Other embodiments include the detection of related bacteria including bacteria with proteins homologous to the proteins described in Table 1 or 2. Such related bacteria include, for example, other strains of *Streptococcus*.

I. Doses and Routes of Administration

1. Dosage Forms, Amounts, and Timing

The amount of antigen in each vaccine or immunogenic composition dose is selected as an effective amount, which induces a prophylactic or therapeutic response, as described above, in either a single dose or over multiple doses. Preferably, the dose is without significant, adverse side effects in typical vaccinees. Such amount will vary depending upon which specific antigen is employed. Generally, it is expected that a dose will comprise 1-1000 µg of protein, in some instances 2-100 µg, for instance 4-40 µg. In some aspects, the vaccine formulation comprises 1-1000 pig of the polypeptide and 1-250 µg of the adjuvant. In some embodiments, the appropriate amount of antigen to be delivered will depend on the age, weight, and health (e.g. immunocompromised status) of a subject. When present, typically an adjuvant will be present in amounts from 1 μg-250 μg per dose, for example 50-150 μg, 75-125 μg or 100 μg.

In some embodiments, only one dose of the vaccine is administered to achieve the results described above. In other embodiments, following an initial vaccination, subjects receive one or more boost vaccinations, for a total of two, three, four or five vaccinations. Advantageously, the number is three or fewer. A boost vaccination may be administered, for example, about 1 month, 2 months, 4 months, 6 months, or 12 months after the initial vaccination, such that one vaccination regimen involves administration at 0, 0.5-2 and 4-8 months. It may be advantageous to administer split doses of vaccines which may be administered by the same or different routes.

The vaccines and immunogenic compositions described herein may take on a variety of dosage forms. In certain embodiments, the composition is provided in solid or powdered (e.g., lyophilized) form; it also may be provided in solution form. In certain embodiments, a dosage form is provided as a dose of lyophilized composition and at least one separate sterile container of diluent.

In some embodiments, the composition will be administered in a dose escalation manner, such that successive administrations of the composition contain a higher concentration of composition than previous administrations. In some embodiments, the composition will be administered in a manner such that successive administrations of the composition contain a lower concentration of composition than previous administrations.

In therapeutic applications, compositions are administered to a patient suffering from a disease in an amount sufficient to treat the patient. Therapeutic applications of a composition described herein include reducing transmissibility, slowing disease progression, reducing bacterial viability or replication, or inhibiting the expression of proteins required for toxicity, such as by 90%, 80%, 70%, 60%, 50%, 40%, 30%, 20% or 10% of the levels at which they would occur in individuals who are not treated with the composition.

In prophylactic embodiments, compositions are administered to a human or other mammal to induce an immune response that can inhibit the establishment of an infectious disease or other condition. In some embodiments, a composition may partially block the bacterium from establishing an infection.

In some embodiments, the compositions are administered in combination with antibiotics. This co-administration is particularly appropriate when the pharmaceutical composition is administered to a patient who has recently been exposed (or ia suspected of having been recently exposed) to *S. pneumoniae*. Many antibiotics are used to treat pneumococcal infections, including penicillin, amoxicillin, amoxicillin/clavulanate, cefuroxime, cefotaxime, ceftriaxone, and vancomycin. The appropriate antibiotic may be selected based on the type and severity of the infection, as well as any known antibiotic resistance of the infection (Jacobs M R "Drug-resistant *Streptococcus pneumoniae*: rational antibiotic choices" Am J Med. 1999 May 3; 106(5A):19S-25S).

2. Routes of Administration

The vaccine formulations and pharmaceutical compositions herein can be delivered by administration to an individual, typically by systemic administration (e.g., intravenous, intraperitoneal, intramuscular, intradermal subcutaneous, subdermal, transdermal, intracranial, intranasal, mucosal, anal, vaginal, oral, buccal route or they can be inhaled) or they can be administered by topical application.

In some embodiments, the route of administration is intramuscular. In other embodiments, the route of administration is subcutaneous. In yet other embodiments, the route of administration is mucosal. In certain embodiments, the route of administration is transdermal or intradermal Certain routes of administration are particularly appropriate for vaccine formulations and immunogenic compositions comprising specified adjuvants. In particular, transdermal administration is one suitable route of administration for *S. pneumoniae* vaccines comprising toxins (e.g. cholera toxin or labile toxin); in other embodiments, the administration is intranasal.

Vaccines formulated with Alphavirus replicons may be administered, for example, by the intramuscular or the subcutaneous route. Vaccines comprising Monophosphory Lipid A (MPL), Trehalose Dicoynomycolate (TDM), and dioctadecyldimethylammonium bromide (DDA) are suitable (inter alia) for intramuscular and subcutaneous administration. A vaccine comprising resiquimod may be administered topically or subcutaneously, for example.

3. Formulations

The vaccine formulation or immunogenic composition may be suitable for administration to a human patient, and vaccine or immunogenic composition preparation may conform to USFDA guidelines. In some embodiments, the vaccine formulation or immunogenic composition is suitable for administration to a non-human animal. In some embodiments, the vaccine or immunogenic composition is substantially free of either endotoxins or exotoxins. Endotoxins may include pyrogens, such as lipopolysaccharide (LPS) molecules. The vaccine or immunogenic composition may also be substantially free of inactive protein fragments which may cause a fever or other side effects. In some embodiments, the composition contains less than 1%, less than 0.1%, less than 0.01%, less than 0.001%, or less than 0.0001% of endotoxins, exotoxins, and/or inactive protein fragments. In some embodiments, the vaccine or immunogenic composition has lower levels of pyrogens than industrial water, tap water, or distilled water. Other vaccine or immunogenic composition components may be purified using methods known in the art, such as ion-exchange chromatography, ultrafiltration, or distillation. In other embodiments, the pyrogens may be inactivated or destroyed prior to administration to a patient. Raw materials for vaccines, such as water, buffers, salts and other chemicals may also be screened and depyrogenated. All materials in the vaccine may be sterile, and each lot of the vaccine may be tested for sterility. Thus, in certain embodiments the endotoxin levels in the vaccine fall below the levels set by the USFDA, for example 0.2 endotoxin (EU)/kg of product for an intrathecal injectable composition; 5 EU/kg of product for a non-intrathecal injectable composition, and 0.25-0.5 EU/mL for sterile water.

In certain embodiments, the preparation comprises less than 50%, 20%, 10%, or 5% (by dry weight) contaminating protein. In certain embodiments, the desired molecule is present in the substantial absence of other biological macromolecules, such as other proteins (particularly other proteins which may substantially mask, diminish, confuse or alter the characteristics of the component proteins either as purified preparations or in their function in the subject reconstituted mixture). In certain embodiments, at least 80%, 90%, 95%, 99%, or 99.8% (by dry weight) of biological macromolecules of the same type present (but water, buffers, and other small molecules, especially molecules having a molecular weight of less than 5000, can be present). In some embodiments, the vaccine or immunogenic composition comprising purified subunit proteins contains less than 5%, 2%, 1%, 0.5%, 0.2%, 0.1% of protein from host cells in which the subunit proteins were expressed, relative to the amount of purified subunit. In some embodiments, the desired polypeptides are substantially free of nucleic acids and/or carbohydrates. For instance, in some embodiments, the vaccine or immunogenic composition contains less than 5%, less than 2%, less than 1%, less than 0.5%, less than 0.2%, or less than 0.1% host cell DNA and/or RNA. In certain embodiments, at least 80%, 90%, 95%, 99%, or 99.8% (by dry weight) of biological macromolecules of the same type are present in the preparation (but water, buffers, and other small molecules, especially molecules having a molecular weight of less than 5000, can be present).

It is preferred that the vaccine or immunogenic composition has low or no toxicity, within a reasonable risk-benefit ratio. In certain embodiments, the vaccine or immunogenic composition comprises ingredients at concentrations that are less than $LD_{50}$ measurements for the animal being vaccinated. $LD_{50}$ measurements may be obtained in mice or other experimental model systems, and extrapolated to humans and other animals. Methods for estimating the $LD_{50}$ of compounds in humans and other animals are well-known in the art. A vaccine formulation or immunogenic composition, and any component within it, might have an $LD_{50}$ value in rats of greater than 100 g/kg, greater than 50 g/kg, greater than 20 g/kg, greater than 10 g/kg, greater than 5 g/kg, greater than 2 g/kg, greater than 1 g/kg, greater than 500 mg/kg, greater than 200 mg/kg, greater than 100 mg/kg, greater than 50 mg/kg, greater than 20 mg/kg, or greater than 10 mg/kg. A vaccine formulation or immunogenic composition that comprises a toxin such as botulinum toxin (which can be used as an adjuvant) should contain significantly less than the $LD_{50}$ of botulinum toxin.

The formulations suitable for introduction of the vaccine formulations or pharmaceutical composition vary according to route of administration. Formulations suitable for parenteral administration, such as, for example, by intraarticular (in the joints), intravenous, intramuscular, intradermal, intraperitoneal, intranasal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampoules and vials.

Injection solutions and suspensions can be prepared from sterile powders, granules, and tablets of the kind previously described. In the case of adoptive transfer of therapeutic T cells, the cells can be administered intravenously or parenterally.

Formulations suitable for oral administration can consist of (a) liquid solutions, such as an effective amount of the polypeptides or packaged nucleic acids suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. The pharmaceutical compositions can be encapsulated, e.g., in liposomes, or in a formulation that provides for slow release of the active ingredient.

The antigens, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like. Aerosol formulations can be delivered orally or nasally.

Suitable formulations for vaginal or rectal administration include, for example, suppositories, which consist of the polypeptides or packaged nucleic acids with a suppository base. Suitable suppository bases include natural or synthetic triglycerides or paraffin hydrocarbons. In addition, it is also possible to use gelatin rectal capsules which consist of a combination of the polypeptides or packaged nucleic acids with a base, including, for example, liquid triglycerides, polyethylene glycols, and paraffin hydrocarbons.

J. Preparation and Storage of Vaccine Formulations and Immunogenic Compositions

The *S. pneumoniae* vaccines and immunogenic compositions described herein may be produced using a variety of techniques. For example, a polypeptide may be produced using recombinant DNA technology in a suitable host cell. A suitable host cell may be bacterial, yeast, mammalian, or other type of cell. The host cell may be modified to express an exogenous copy of one of the relevant polypeptide genes. Typically, the gene is operably linked to appropriate regulatory sequences such as a strong promoter and a polyadenylation sequence. In some embodiments, the promoter is inducible or repressible. Other regulatory sequences may provide for secretion or excretion of the polypeptide of interest or retention of the polypeptide of interest in the cytoplasm or in the membrane, depending on how one wishes to purify the polypeptide. The gene may be present on an extrachromosomal plasmid, or may be integrated into the host genome. One of skill in the art will recognize that it is not necessary to use a nucleic acid 100% identical to the naturally-occurring sequence. Rather, some alterations to these sequences are tolerated and may be desirable. For instance, the nucleic acid may be altered to take advantage of the degeneracy of the genetic code such that the encoded polypeptide remains the same. In some embodiments, the gene is codon-optimized to improve expression in a particular host. The nucleic acid may be produced, for example, by PCR or by chemical synthesis.

Once a recombinant cell line has been produced, a polypeptide may be isolated from it. The isolation may be accomplished, for example, by affinity purification techniques or by physical separation techniques (e.g., a size column).

In a further aspect of the present disclosure, there is provided a method of manufacture comprising mixing one or more polypeptides or an immunogenic fragment or variant thereof with a carrier and/or an adjuvant.

In some embodiments, antigens for inclusion the vaccine formulations and immunogenic compositions may be produced in cell culture. One method comprises providing one or more expression vectors and cloning nucleotides encoding one or more polypeptides selected from polypeptides having an amino acid sequence of Table 1 or Table 2, then expressing and isolating the polypeptides.

The immunogenic polypeptides described herein, and nucleic acid compositions that express the polypeptides, can be packaged in packs, dispenser devices, and kits for administering nucleic acid compositions to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition, such as those disclosed herein.

V. EXAMPLES

Example 1

Antigen Identification and Pooled Murine Screens

Each open reading frame predicted in the S. pneumoniae TIGR4 genome was cloned into an expression vector comprising a tag that is able to be presented by the major histocompatibility complex (MHC). Each construct was then expressed in E. coli, and full-length expression validated by a surrogate assay that identifies the tag in the context of MHC. The screen is described in more detail in International Application WO 2010/002993. In order to facilitate screening the large library, the library was pooled such that four induced library clones were present in each well. In order to screen T cells from mice immunized against S. pneumoniae, an aliquot of the pooled library was added to peritoneal-derived macrophages. The macrophages were allowed to bind the tagged S. pneumoniae antigens via the MHC. After 2 hr at 37° C., the macrophages were washed with PBS. The macrophages were then fixed with 1% paraformaldehyde for 15 min and washed extensively with PBS. $10^5$ T cells were added to each well in 200 µL of RP-10 media. The T cells had previously been isolated from mice that had been immunized 2 times with killed S. pneumoniae bacteria with cholera toxin adjuvant. The assay plates were incubated for 72 hrs at 37° C. The amount of IL-17 in the supernatant of each well was determined through the use of an IL-17 ELISA assay. The threshold for a positive result was set at two standard deviations above the mean of all samples.

Example 2

Deconvolution of the Positive Murine Pools

A secondary screen was used to determine which antigen(s) out of the four clones in each well induced the positive response observed in the pooled screen described in Example 1. All the clones in each positive pool were pulsed individually onto peritoneal macrophages in duplicate wells. T cells isolated from immunized mice from the same genetic background as the initial screen were used to screen the pulsed macrophages using the IL-17 assay described in Example 1. Individual antigens that induced an average response in the duplicate wells greater than two standard deviations above the mean of negative control samples were considered positive responses. The library plasmids present in these positive clones were sequenced to confirm the identity of the antigen. The antigens SP_1574, SP_1655, SP_2106, SP_0148, SP_1473, SP_0605, SP_1177, SP_0335, SP_0906, SP_1828, SP_2157, SP_1229, SP_1128, SP_1836, SP_1865, SP_0904, SP_0882, SP_0765, SP_1634, SP_0418, SP_1923, SP_1313, SP_0775, SP_0314, SP_0912, SP_0159, SP_0910, SP_2148, SP_1412, SP_0372, SP_1304, SP_2002, SP_0612, SP_1988, SP_0484, SP_0847, SP_1527, SP_0542, SP_0441, SP_0350, SP_0014, SP_1965, SP_0117, and SP_2108 were confirmed using this method.

Example 3

Antigen Identification and Pooled Human Screens

CD4+ T cells and CD14+ monocytes were isolated from peripheral blood acquired from human donors. The monocytes were differentiated into dendritic cells by culturing them in GM-CSF and IL-4 containing media, essentially as described in Tedder T F and Jansen P J (1997 "Isolation and generation of human dendritic cells." *Current Protocols in Immunology Supp* 23: 7.32.1-7.32.16). After five days in culture, the dendritic cells were seeded into 384 well plates. The CD4+ T cells were expanded in culture to ensure sufficient quantities.

Each open reading frame predicted in the S. pneumoniae TIGR4 genome was cloned into an expression vector comprising a tag that is able to be presented by the major histocompatibility complex (MHC). Each construct was then expressed in E. coli, and full-length expression validated by a surrogate assay that identifies the tag in the context of MHC. In order to facilitate screening the large library, the library was pooled such that four induced library clones were present in each well. In order to screen the human T cells, an aliquot of the pooled library was added to the seeded dendritic cells in 384-well plates. After 2 hr at 37° C., the dendritic cells were fixed with 1% paraformaldehyde for 15 min and washed extensively with phosphate buffer and lysine buffer. 40,000 of the CD4+ T cells in 70 µL of RP-10 media were added to each well of a 384-well plate. The assay plates were incubated for 3 days at 37° C. The amount of IL-17 in the supernatant of each well was determined through the use of an IL-17 ELISA assay. In different iterations of the screen, the threshold for a positive result was set at two standard deviations above the mean of all samples, two standard deviations above the mean of negative controls, or 1.78 times the median absolution deviation of the data set. Positive pools were then deconvoluted as described in Example 4.

Example 4

Deconvolution of the Positive Human Pools

For all antigens, deconvolution was performed by comparing the results of two pool screens. In this method, two different sets of pools were prepared, so that a polypeptide was with three different polypeptides between the first and second pools. Consequently, it is possible to determine which polypeptides are antigens by identifying which polypeptides are in positive pools in both the first and second sets. In this deconvolution method, a pool was identified as positive if it was at least 1.78 times the median absolution deviation of the data set.

An antigen was identified as a positive hit if it was positive in at least two repeated secondary screens. The antigens SP2108, SP0641, SP1393, SP0024, SP0641.1, SP1072, SP1384 and SP2032 were identified using the above approach.

Example 5

SP2108, SP0148 and SP1634 Polypeptides

Figure 2:
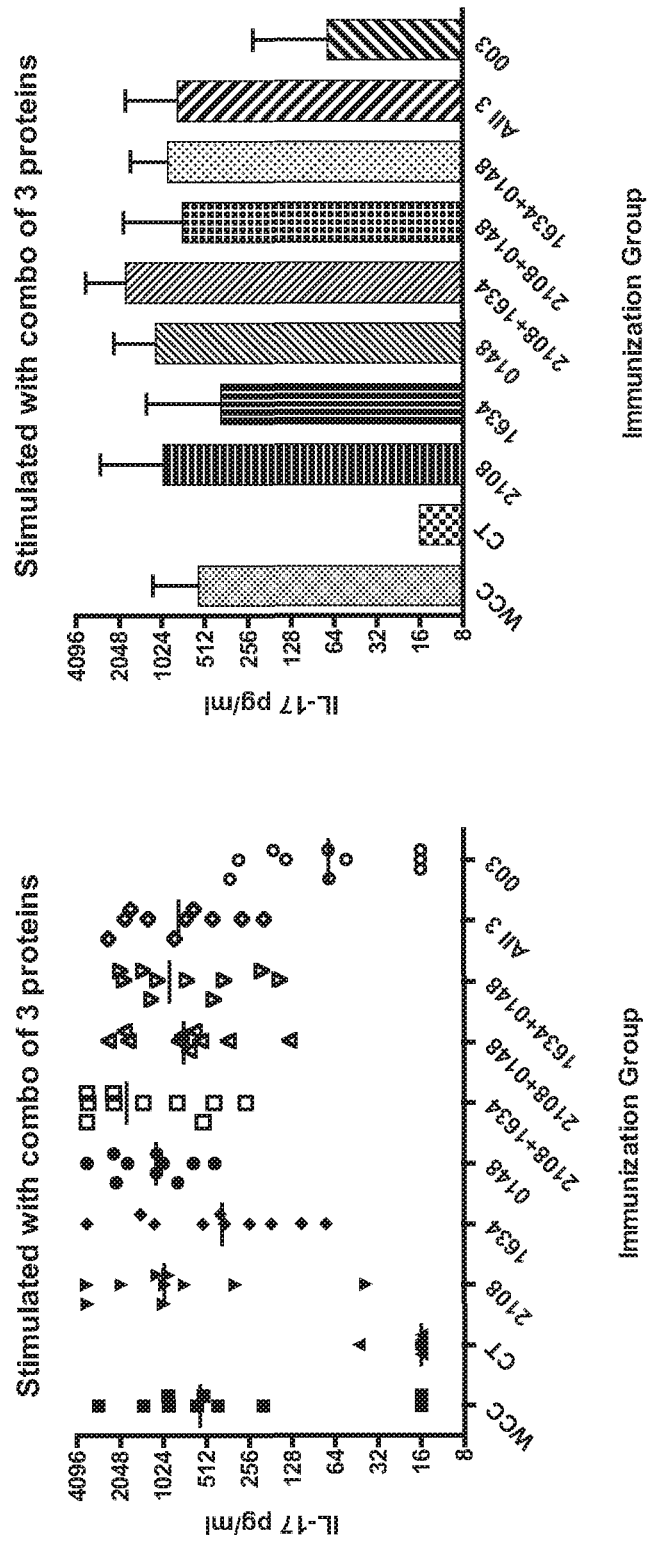
FIG. 2 shows the concentration of IL-17 generated by blood samples from mice that were immunized with the indicated protein(s) and cholera toxin, then stimulated with a combination of three proteins (SP2108, SP0148, and SP1634), as described in Example 5.
Figure 3:
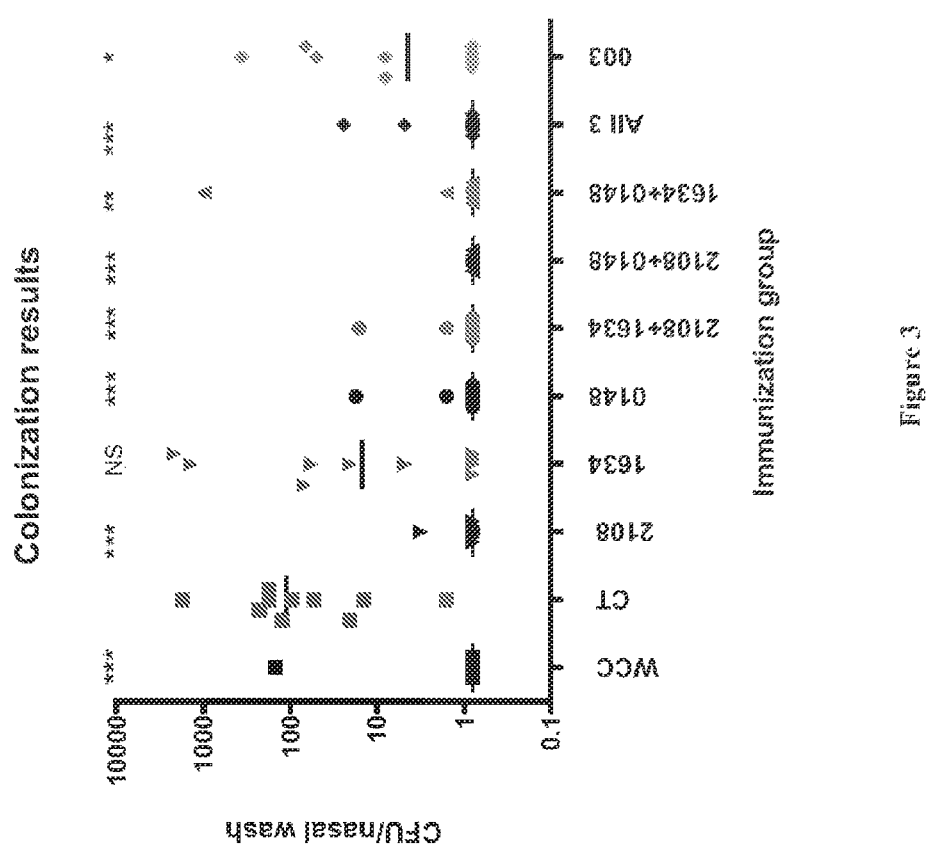
FIG. 3 shows the number of *S. pneumoniae* colonies obtained from a nasal wash in mice that were immunized with the indicated protein(s) and cholera toxin, then challenged with intranasal administration of *S. pneumoniae*, as described in Example 5. 003 represents a control irrelevant antigen.

The SP2108 polypeptide (SEQ ID NO: 9), SP0148 polypeptide (SEQ ID NO: 7) and SP1634 polypeptide (see Table 2) were formulated as vaccine compositions using 4 µg of the polypeptide in combination with 1 µg cholera toxin. For combinations, 4 µg of each polypeptide was used. The compositions were administered intranasally to C57BU/6 mice three times, one week apart. The subjects were then allowed to rest for 3 weeks, and bled at that time for immunogenicity. For this assay, heparinized whole blood was collected from the retrograde orbital sinus. The total PBMC were stimulated with either killed whole cells (WCC) or a combination of the three polypeptides in round bottomed tubes for three days. The supernatants were then harvested and evaluated by ELISA for IL-17 levels. Cholera toxin alone (CT) or an unrelated antigen from HSV (003) were used as negative controls. Results are shown in FIGS. 1 and 2. The subjects were allowed to rest an additional 2 weeks, at which time they were challenged with intranasal administration of S. pneumoniae. The subjects were sacrificed a week later, and the number of colony-forming units (CFU) was counted from nasal washes. Results are shown in FIG. 3.

Example 6

SP0882 and SP0314 Polypeptides

Figure 4:
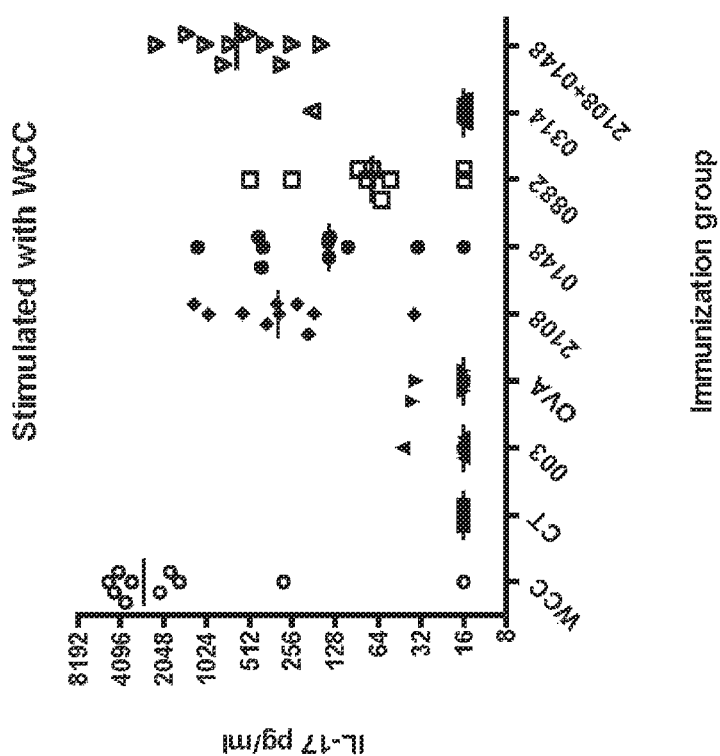
FIG. 4 shows the concentration of IL-17 generated by blood samples from mice that were immunized with the indicated protein(s) and cholera toxin, then stimulated with killed, unencapsulated whole cell *S. pneumoniae*, as described in Example 6.
Figure 5:
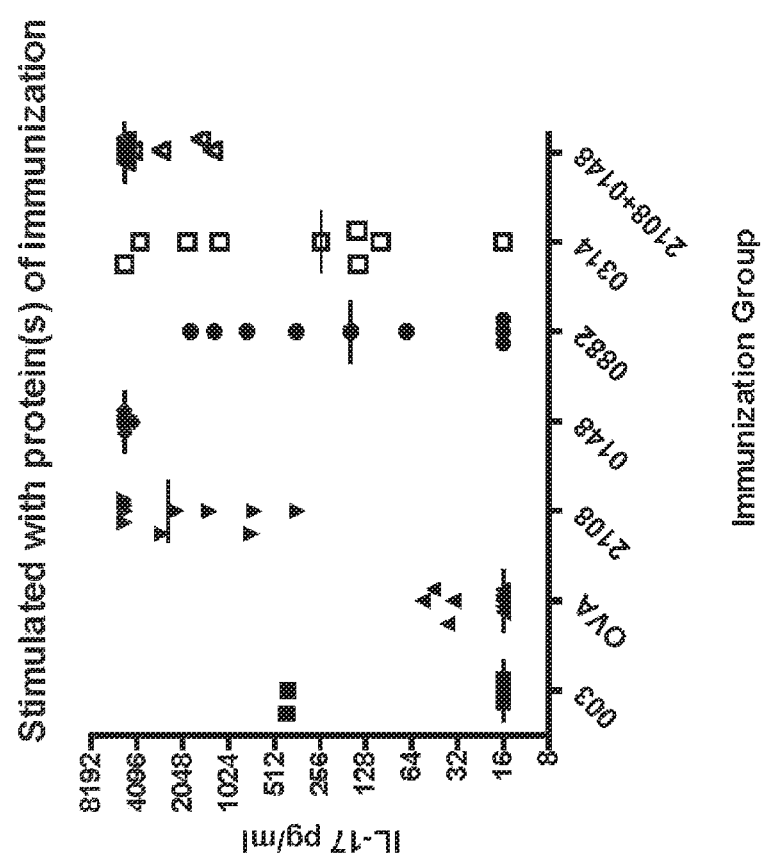
FIG. 5 shows the concentration of IL-17 generated by blood samples from mice that were immunized with the indicated protein(s) and cholera toxin, then stimulated by the indicated proteins and combination, as described in Example 5.
Figure 6:
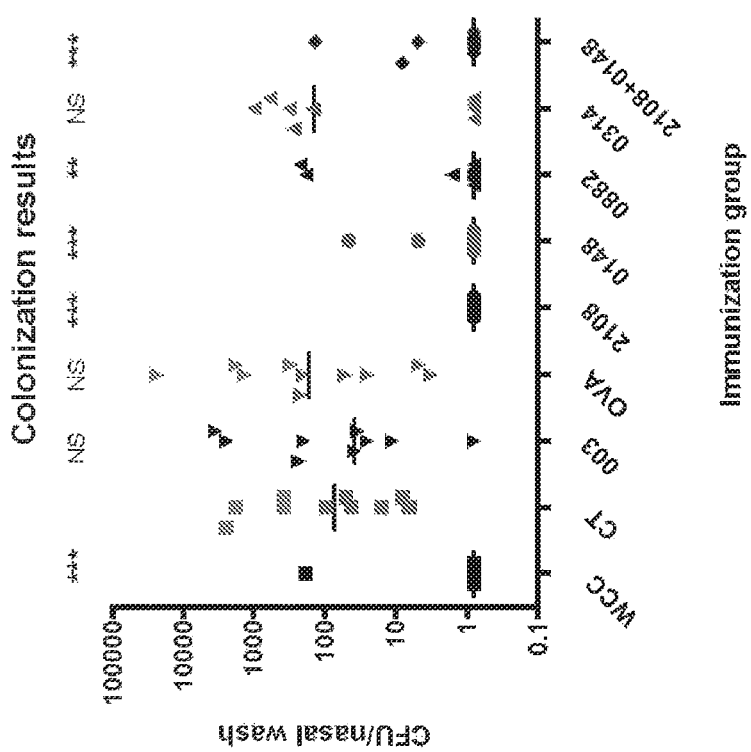
FIG. 6 shows the number of *S. pneumoniae* colonies obtained from a nasal wash in mice that were immunized with the indicated protein(s) and cholera toxin, then challenged with intranasal administration of *S. pneumoniae*, as described in Example 6. The HSV-2 protein ICP47 with the gene name US12 (NP_044543.1, NC_001798.1; shown in the figure as 003) and ovalbumin (OVA) represent control antigens.

This example used the same protocols as Example 5, except that only two doses of the vaccine composition were administered. In these experiments, the SP0882 polypeptide (SEQ ID NO: 2) and SP0314 polypeptides (see Table 2) were used in conjunction with the three polypeptides tested in Example 5. Results of the immunogenicity assay are shown in FIGS. 4 and 5. Results of the colonization assay are shown in FIG. 6.

Example 7

SP1072, SP0641N, and SP0024 Polypeptides

Figure 7:
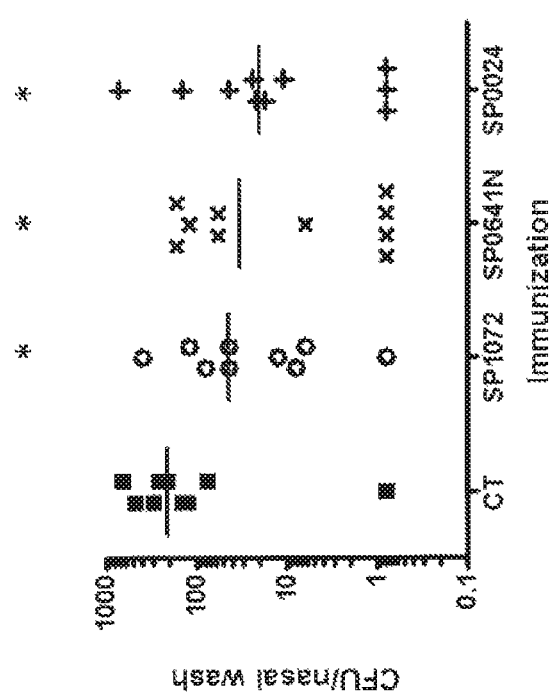
FIG. 7 shows the number of *S. pneumoniae* colonies obtained from a nasal wash in mice that were immunized with the indicated protein(s) and cholera toxin, then challenged with intranasal administration of *S. pneumoniae*, as described in Example 7.

This example used a protocol similar to that of Example 5, except that two doses of the vaccine composition were administered, one week apart. Four weeks after the last immunization, the mice were challenged intranasally with live type 6B S. pneumoniae. One week later the bacterial burden was assessed in each mouse by plating a nasal lavage on selective media and counting CFU. The CFU isolated from each mouse is plotted for each immunized cohort. The results are shown in FIG. 7. Statistically significant results are indicated in the figure (*=p=value<0.05).

Example 8

SP0148, SP0314, SP0882, and SP2108 Polypeptides Tested in the BALB/c Mouse

Figure 8:
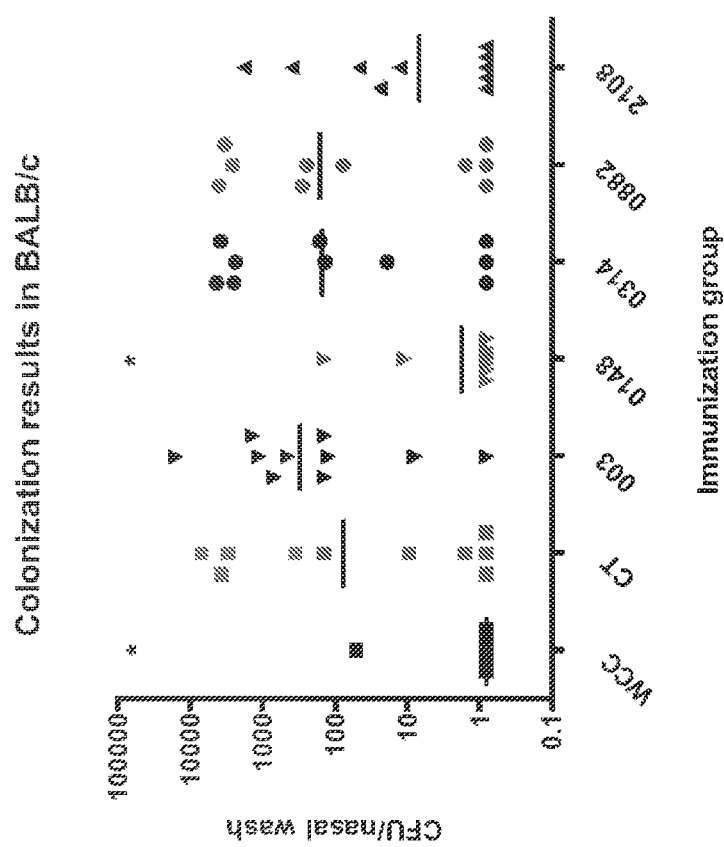
FIG. 8 shows the number of *S. pneumoniae* colonies obtained from a nasal wash in BALB/c mice that were immunized with the indicated protein(s) and cholera toxin, then challenged with intranasal administration of *S. pneumoniae*, as described in Example 8.

To determine whether similar immune responses were seen across different mouse genotypes, several polypeptides were administered to BALB/c mice. Using a protocol similar to that of Example 5, the mice were immunized, challenged with S. pneumoniae, and the number of CFU was recorded. The results of this experiment are shown in FIG. 8.

---

SEQUENCES
Potypeptide Sequences

SEQ ID NO: 1
SP0024
>gi|14971488|gb|AAK74215.1| conserved hypothetical protein Streptococcus pneumoniae TIGR4
MSYFEQFMQANQAYVALHGQLNLPLKPKTRVAIVTCMDSRLHVAQALGLA

LGDAHILRNAGGRVTEDMIRSLVISQQQMGTREIVVLHHTDCGAQTFENE

PFQEYLKEELGVDVSDQDFLPFQDIEESVREDMQLLIESPLIPDDVIISG

AIYNVDTGSMTVVEL

SEQ ID NO: 2
SP0882
>gi|14972356|gb|AAK75009.1| conserved hypothetical protein (Streptococcus pneumoniae TIGR4)
MNQSYFYLKMKEHKLKVPYTGKERRVRILLPKDYEKDTDRSYPVVYFHDG

QNVFNSKESFIGHSWKIIPAIKRNPDISRMIVVAIDNDGMGRMNEYAAWK

FQESPIPGQQFGGKGVEYAEFVMEVVKPFIDETYRTKADCQHTAMIGSSL

GGNITQFIGLEYQDQIGCLGVFSSANWLHQEAFNRYFECQKLSPDQRIFI

YVGTEEADDTDKTLMDGNIKQAYIDSSLCYYHDLIAGGVHLDNLVLKQSG

AIHSEIPWSENLPDCLRFFAEKW

SEQ ID NO: 3
SP0882N
MNQSYFYLKMKEHKLKVPYTGKERRVRILLPKDYEKDTDRSPYVVYFHDG

QNVFNSKESFIGHSWKIIPAIKRNPDISRMIVVAIDNDGMGRMNEYAAWK

RQESPIPGQQFGGKGVEYAEFVMEVVKPFI

SEQ ID NO: 4
SP0882 with exogenous leader
MSSKFMKSAAVLGTATLASLLLVACMNQSYFYLKMKEHKLKVPYTGKERR

VRILLPKDYEKDTDRSYPVVYFHDGQNVFNSKESFIGHSWKIIPAIKRNP

DISRMIVVAIDNDGMGRMNEYAAWKFQESPIPGQQFGGKGVEYAEFVMEV

VKPF

---

We claim:

1. A vaccine formulation comprising:
   (i) a pharmaceutically acceptable carrier,
   (ii) an effective amount of an adjuvant,
   (iii) a first polypeptide comprising an amino acid sequence at least 95% identical to SEQ ID 6 or SEQ ID 7, and
   (iv) a second polypeptide comprising an amino acid sequence at least 95% identical to SEQ ID 9 or SEQ ID 10.

2. The vaccine formulation of claim 1, which comprises a polypeptide having an amino acid sequence comprising SEQ ID NO: 9.

3. The vaccine formulation of claim 1, which comprises a polypeptide having an amino acid sequence comprising SEQ ID NO: 10.

4. The vaccine formulation of claim 1, wherein the polypeptide is conjugated to an immunogenic carrier.

5. The vaccine formulation of claim 1, which comprises at least one lipidated polypeptide.

6. The vaccine formulation of claim 1, wherein the adjuvant is an agonist of toll-like receptors (TLRs).

7. The vaccine formulation of claim 1, wherein the adjuvant is alum.

8. The vaccine formulation of claim 1, wherein the vaccine formulation inhibits infection by *Streptococcus pneumoniae* in an uninfected subject.

9. The vaccine formulation of claim 1, wherein the vaccine formulation inhibits *Streptococcus pneumoniae* colonization in an individual.

10. The vaccine formulation of claim 1, wherein the vaccine formulation inhibits *Streptococcus pneumoniae* symptoms.

11. A method for treating a subject suffering from or susceptible to *Streptococcus pneumoniae* infection, comprising administering an effective amount of a vaccine formulation according to claim 1.

12. The method of claim 11, wherein the method inhibits infection by *Streptococcus pneumoniae* in an uninfected subject.

13. The method of claim 11, wherein the method inhibits *Streptococcus pneumoniae* colonization in an individual.

14. The method of claim 11, wherein the method inhibits *Streptococcus pneumoniae* symptoms.

15. The method of claim 11, wherein the method treats a subject with one dose.

16. The method of claim 11, wherein the method treats a subject within three doses.

17. The method of claim 11, wherein the subject is a human.

18. The vaccine formulation of claim 1, which comprises a polypeptide having an amino acid sequence comprising SEQ ID NO: 6.

19. The vaccine formulation of claim 1, which comprises a polypeptide having an amino acid sequence comprising SEQ ID NO: 7.

20. A pharmaceutical composition comprising:
(i) a pharmaceutically acceptable carrier,
(ii) an effective amount of an adjuvant,
(iii) a first polypeptide comprising an amino acid sequence at least 95% identical to SEQ ID 6 or SEQ ID 7, and
(iv) a second polypeptide comprising an amino acid sequence at least 95% identical to SEQ ID 9 or SEQ ID 10.

21. The pharmaceutical composition of claim 20, which comprises a polypeptide having an amino acid sequence comprising SEQ ID NO: 6.

22. The pharmaceutical composition of claim 20, which comprises a polypeptide having an amino acid sequence comprising SEQ ID NO: 7.

23. The pharmaceutical composition of claim 20, which comprises a polypeptide having an amino acid sequence comprising SEQ ID NO: 9.

24. The pharmaceutical composition of claim 20, which comprises a polypeptide having an amino acid sequence comprising SEQ ID NO: 10.

25. The pharmaceutical composition of claim 20, which comprises a polypeptide having an amino acid sequence consisting of SEQ ID NO: 6.

26. The pharmaceutical composition of claim 20, which comprises a polypeptide having an amino acid sequence consisting of SEQ ID NO: 7.

27. The pharmaceutical composition of claim 20, which comprises a polypeptide having an amino acid sequence consisting of SEQ ID NO: 9.

28. The pharmaceutical composition of claim 20, which comprises a polypeptide having an amino acid sequence consisting of SEQ ID NO: 10.

29. The pharmaceutical composition of claim 20, wherein the polypeptide is conjugated to an immunogenic carrier.

30. The pharmaceutical composition of claim 20, which comprises at least one lipidated polypeptide.

31. The vaccine formulation of claim 1, which comprises a polypeptide having an amino acid sequence consisting of SEQ ID NO: 6.

32. The vaccine formulation of claim 1, which comprises a polypeptide having an amino acid sequence consisting of SEQ ID NO: 7.

33. The vaccine formulation of claim 1, which comprises a polypeptide having an amino acid sequence consisting of SEQ ID NO: 9.

34. The vaccine formulation of claim 1, which comprises a polypeptide having an amino acid sequence consisting of SEQ ID NO: 10.

* * * * *